(12) United States Patent
Ranga

(10) Patent No.: US 9,439,922 B2
(45) Date of Patent: Sep. 13, 2016

(54) TAT DNA SEQUENCES, GENE CONSTRUCTS, VACCINE AND PROCESSES THEREOF

(75) Inventor: Udaykumar Ranga, Karnataka (IN)

(73) Assignee: JAWAHARLAL NEHRU CENTRE FOR ADVANCED SCIENTIFIC RESEARCH, Bangalore (IN)

( * ) Notice: Subject to any disclaimer, the term of this patent is extended or adjusted under 35 U.S.C. 154(b) by 546 days.

(21) Appl. No.: 12/988,341

(22) PCT Filed: May 14, 2009

(86) PCT No.: PCT/IN2009/000284
§ 371 (c)(1),
(2), (4) Date: Jan. 20, 2011

(87) PCT Pub. No.: WO2009/139004
PCT Pub. Date: Nov. 19, 2009

(65) Prior Publication Data
US 2011/0165191 A1    Jul. 7, 2011

(30) Foreign Application Priority Data
May 14, 2008 (IN) .................. 01174/CHE/2008

(51) Int. Cl.
| | |
|---|---|
| C07H 21/04 | (2006.01) |
| C07K 14/435 | (2006.01) |
| C12Q 1/68 | (2006.01) |
| C07H 21/00 | (2006.01) |
| C07K 14/47 | (2006.01) |
| A61K 31/7088 | (2006.01) |
| A61K 39/21 | (2006.01) |
| C07K 14/005 | (2006.01) |
| A61K 39/12 | (2006.01) |
| A61K 39/00 | (2006.01) |

(52) U.S. Cl.
CPC ........... *A61K 31/7088* (2013.01); *A61K 39/12* (2013.01); *A61K 39/21* (2013.01); *C07K 14/005* (2013.01); *A61K 2039/543* (2013.01); *A61K 2039/545* (2013.01); *A61K 2039/6031* (2013.01); *A61K 2039/6037* (2013.01); *A61K 2039/6075* (2013.01); *C07K 2319/00* (2013.01); *C12N 2740/15022* (2013.01); *C12N 2740/16122* (2013.01); *C12N 2740/16322* (2013.01); *C12N 2740/16334* (2013.01)

(58) Field of Classification Search
CPC .......... A61K 39/21; A61K 2039/543; C07K 14/005; C12N 2740/16122
USPC ......................................... 424/208
See application file for complete search history.

(56) References Cited

U.S. PATENT DOCUMENTS

| | | | |
|---|---|---|---|
| 6,440,741 | B2 | 8/2002 | Fisher et al. |
| 6,686,333 | B1 | 2/2004 | Kashanchi et al. |
| 7,811,573 | B2 | 10/2010 | Ensoli |
| 2004/0005330 | A1 | 1/2004 | Rappaport et al. |
| 2004/0224407 | A1 | 11/2004 | Fisher et al. |
| 2005/0032039 | A1* | 2/2005 | Sastry et al. ............. 435/5 |

FOREIGN PATENT DOCUMENTS

| | | | |
|---|---|---|---|
| EP | 1 279 404 A1 | | 1/2003 |
| WO | WO9927958 | * | 6/1999 |
| WO | 00/55310 A1 | | 9/2000 |
| WO | WO0078969 | * | 12/2000 |
| WO | 03/046172 A2 | | 6/2003 |
| WO | 03/054006 A2 | | 7/2003 |

OTHER PUBLICATIONS

Rees et al., Bicistronic vector for the creation of stable mammalian cell lines that predisposes all antibiotic-resistant cells to express recombinant protein, 1996, BioTechniques, 20(1):102-104.*
Borkow, Mouse models for HIV-1 infection, 2005, IUBMB Life, 57(12):819-823.*
Boberg, et al. "Murine models for HIV vaccination and challenge", Expert Rev. Vaccines 7(1), (2008), pp. 117-130.

* cited by examiner

*Primary Examiner* — Janet L Andres
*Assistant Examiner* — Barry A Chestnut
(74) *Attorney, Agent, or Firm* — James R. Crawford; Norton Rose Fulbright US LLP

(57) ABSTRACT

The present invention relates to non toxic, immunogenic viral Tat DNA sequences comprising wherein the Tat Sequence is rendered non toxic and immunogenic by insertion of T-Helper Epitope into the Cysteine-rich domain, or Basic domain or Core domain of said Tat DNA sequence, optionally along with insertion of a synthetic Intron between C-terminal region and Exon II region of the Tat DNA Sequence. The present invention also relates to elongation factor promoter constructs and process thereof. Also the present invention relates to a process of obtaining the non toxic and immunogenic Tat DNA sequence and vaccine and a method thereof.

15 Claims, 17 Drawing Sheets

Figure 1:
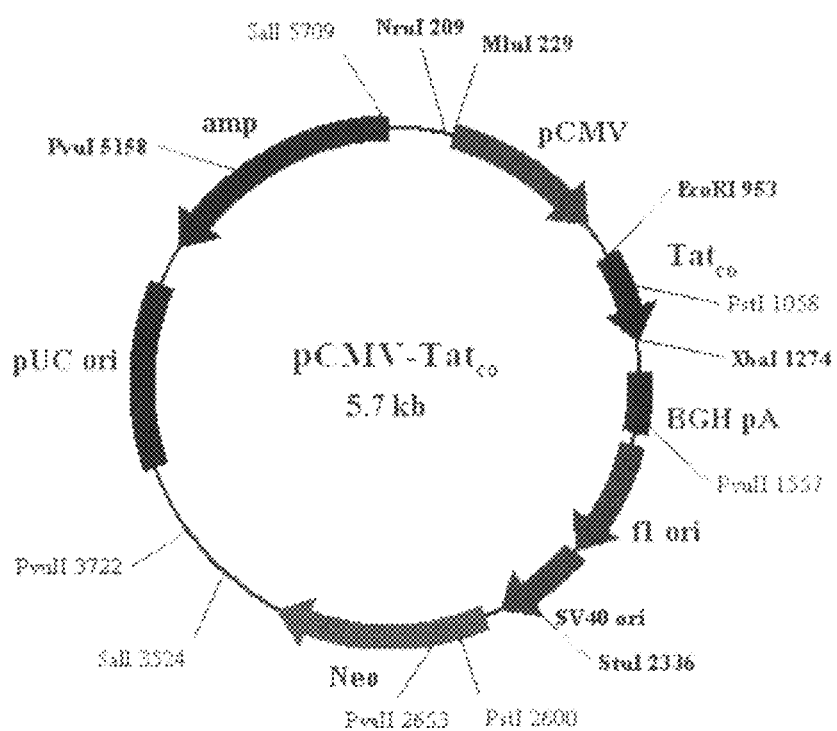

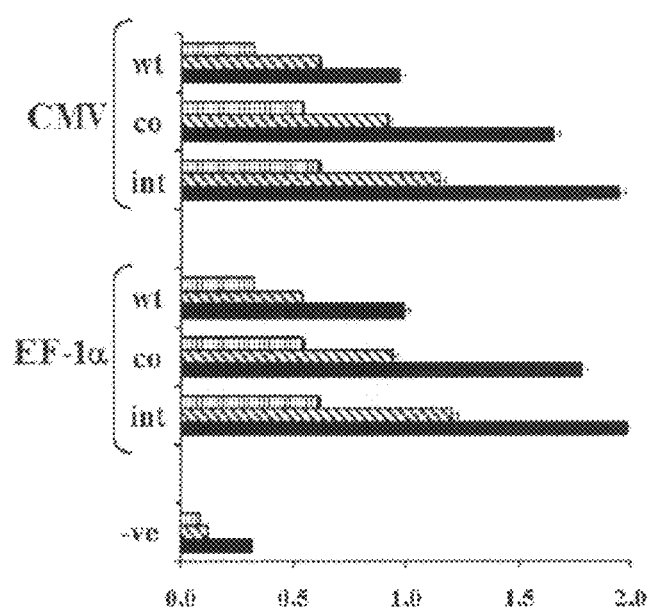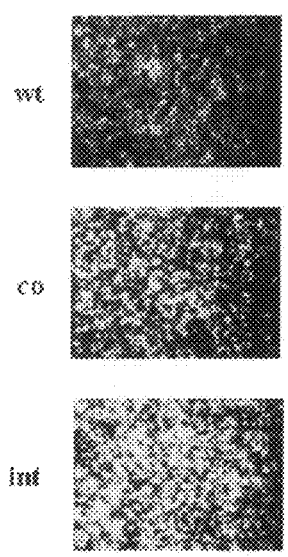
FIG. 7

(A) IFNγ ELISPOT
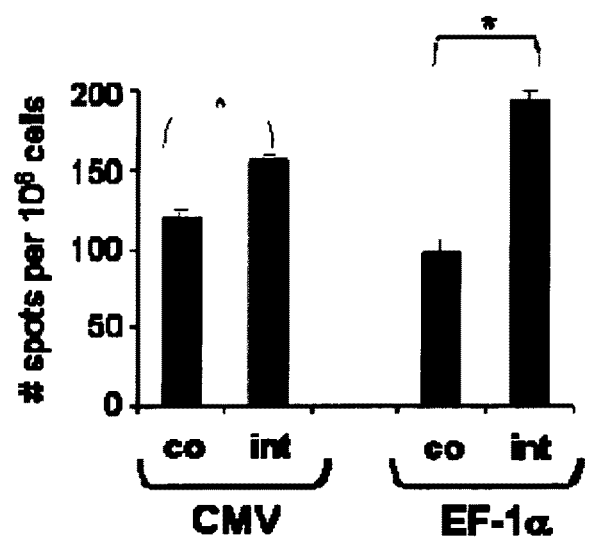
(B) Lymphoproliferation assay
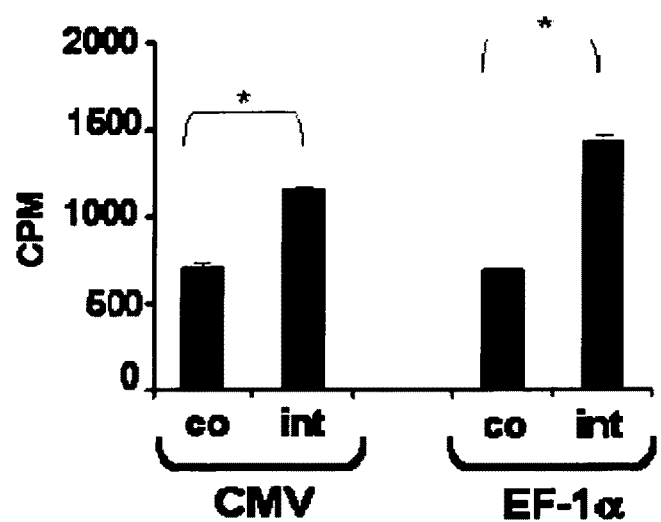
FIG. 8

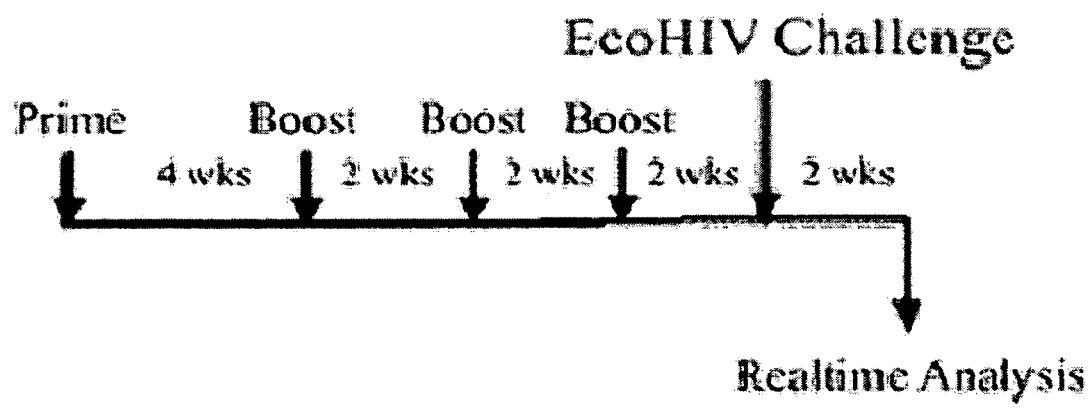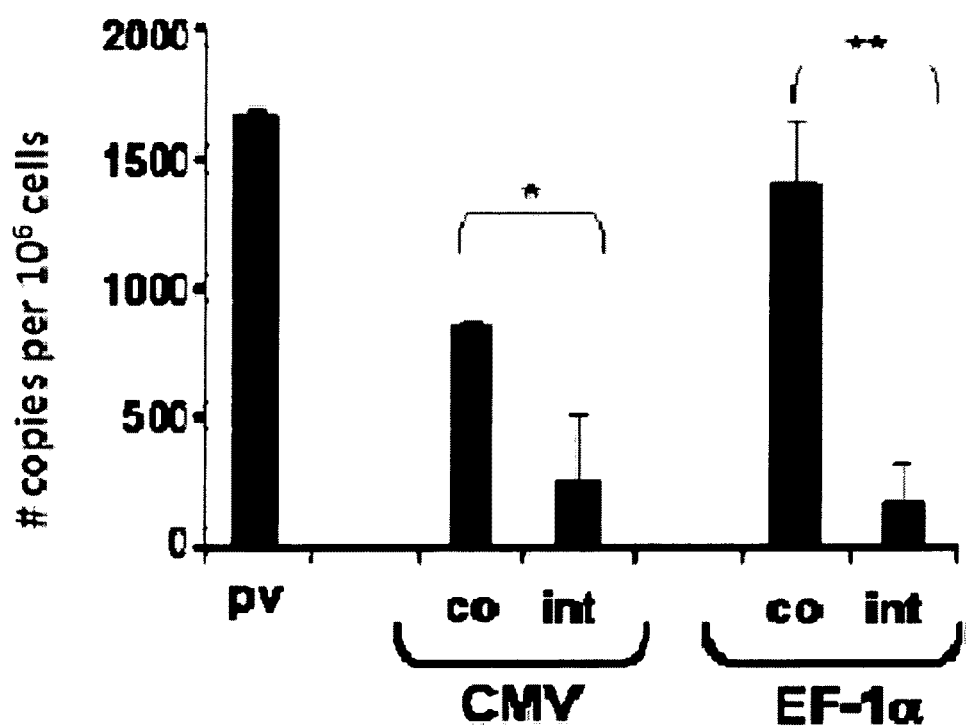
FIG. 9

(A) GFP analysis
(B) Western blot analysis
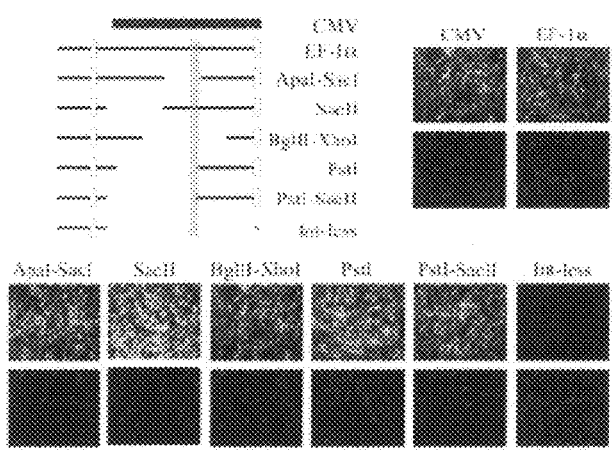
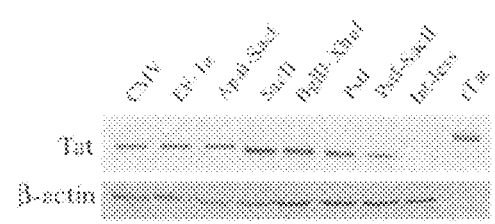
FIG. 12

TAT DNA SEQUENCES, GENE CONSTRUCTS, VACCINE AND PROCESSES THEREOF

RELATED APPLICATIONS

This application is a §371 application from PCT/IN2009/000284 filed May 14, 2009, which claims priority from Indian Patent Application No. 01174/CHE/2008 filed May 14, 2008, each of which is herein incorporated by reference in its entirety.

FIELD OF THE INVENTION

The present invention relates to non toxic, immunogenic viral Tat DNA sequences comprising wherein the Tat Sequence is rendered non toxic and immunogenic by insertion of T-Helper Epitope into the Cysteine-rich domain, or Basic domain or Core domain of said Tat DNA sequence, optionally along with insertion of a synthetic Intron between C-terminal region and Exon II region of the Tat DNA Sequence. The present invention also relates to elongation factor promoter constructs and process thereof. Also the present invention relates to a process of obtaining the non toxic and immunogenic Tat DNA sequence and vaccine and a method thereof.

BACKGROUND AND PRIOR ART OF THE INVENTION

Most of the major laboratories working on the Tat vaccine have failed to pay attention to basics. (1) They over looked the fact that to control viral infection, Tat must be presented to the immune system as a DNA vaccine, not as a protein or toxoid. (2) These workers also underestimated the importance of immune-modulation of Tat to make it immunodominant. (3) Importantly, some workers disregarded the need to modulate Tat to reduce or alleviate its toxic properties and used native Tat in their vaccines. While others realized the importance of attenuating Tat but adapted an erroneous strategy of chemically modifying Tat to convert it into less toxic form of a Tat toxoid. Tat toxoid is known to differ from the native Tat in the quality of immune responses it would induce in immunizations.

HIV Vaccine Design Traditionally been Dominated by Structural Proteins Like Env:

HIV vaccine development traditionally depended on structural proteins like env, gag and regulatory protein Nef all of which are immunodominant. Antibody response to env is certainly critical to prevent or reduce the rate of infection at the entry level. Recent studies have demonstrated the importance of cell-mediated immune responses to gag in restricting viral proliferation in vivo (Kiepiela et al., 2007; Novitsky et al., 2003; Novitsky et al., 2006). In contrast, evidence is also available that gag vaccines failed to induce protective immune response (Saini et al., 2007; Putkonen et al., 1998). In a head-to-head comparison of Tat vs gag immune responses in a primate model, immune responses to Tat but not gag provided protection against viral challenge (Stittelaar et al., 2002). Inclusion of an antigen like Nef in vaccine design could be risky given that Nef is an accessory protein (not an essential protein unlike env, gag or Tat), the presence of which is not critical for the survival of the virus and the virus could efficiently develop resistance against Nef. Although env vaccines conferred protection against autologous viral strains, antigenic variation is a challenge for vaccine design (Osmanov et al., 1996). Further, most of the clinical trials using env and other structural antigens did not provide protective efficacy (Veljkovic et al., 2003; Kaiser, 2008; Bubnoff, 2007; Steinbrook, 2007).

A Need for Multi-Component HIV Vaccine:

In this backdrop, inclusion multiple antigens in HIV vaccine design and optimizing each individual antigen for efficient immune response is essential. A need for developing multi-component vaccines is being increasingly realized, to induce broader immune responses against the viral infection, by incorporating multiple viral antigens (Ho and Huang, 2002). Extensive work from various laboratories has identified the viral structural proteins, gag and pol, and viral regulatory proteins Nef, Tat and Rev, as potential candidates for vaccine development (Calarota et al., 1999; Evans et al., 1999; Putkonen et al., 1998). Of these non-env candidates, Tat occupies a special place for several reasons.

Significance of Tat for HIV Vaccine Development:

First of all, the functional importance of this viral antigen to the infectivity of the virus (Gallo, 1999; Jeang et al., 1999; Rubartelli et al., 1998; Rusnati and Presta, 2002), and the existence of an inverse correlation between immune responses to Tat and disease progression (Allen et al., 2000; Re et al., 1995; Re et al., 2001; Reiss et al., 1990; Zagury et al., 1998b; van Baalen et al., 1997) make Tat an important candidate vaccine. Several studies showed that immune responses to Tat, humoral or cellular, appear to have protected against disease progression or viral load (Richardson et al., 2003; Re et al., 2001; Zagury et al., 1998b; van Baalen et al., 1997; Re et al., 1996; Rodman et al., 1992; Reiss et al., 1990; Wieland et al., 1990) although a few studies demonstrated absence of such effect (Senkaali et al., 2008). Tat is expressed early in the viral life cycle and is functionally important for its infectivity and pathogenicity (Jeang et al., 1999). In addition to regulating viral gene expression, Tat modulates expression of various genes of the host. Further, Tat is secreted extracellularly and the extracellular Tat governs viral latency and contributes to disease progression (Noonan and Albini, 2000). Inducing cellular as well as humoral immune responses against Tat is critical owing to its early expression in the viral life cycle and to its extracellular secretion (Goldstein, 1996; Rusnati and Presta, 2002). Lastly, as a consequence of its pleiotropic biologic functions, a variety of functional assays are available for Tat, to study the inhibitory effect of immune components on its biological functions.

The Cysteine-Rich Domain and Basic Domains of Tat Regulate Important Biological Functions of Tat:

The Tat protein of HIV-1 is a small polypeptide of 101 amino acid residues encoded by two exons. Like many transcription factors, Tat is structurally flexible (Dyson and Wright, 2005) and as a result, its crystal structure could not be determined by X-ray crystallography. Structural prediction of Tat by NMR spectroscopy suggests lack of obvious secondary structures in Tat (Peloponese, Jr. et al., 2000; Gregoire et al., 2001; Shojania and O'neil, 2006). Depending on the nature of amino acid distribution, five conserved functional domains have been identified in Tat exon-1 (Jeang et al., 1999). These include (1) the proline-rich N-terminal region consisting of residues 1-21 is predicted to assume an α-helical structure, (2) the cysteine-rich domain (CRD) consisting of residues 22-37 and makes an intra-molecular disulphide bond, (3) the core domain consisting of the residues 38-48 makes the third domain, (4) the basic domain consists of the residues 49-57 and (5) the C-terminal region consisting of the residues 58-72 is rich in glutamine. The CRD and the core domain together constitute the activation domain that regulates viral promoter transactivation (Jeang et al., 1999). In addition, CRD regulates many more functions including lymphocyte chemotaxis (Albini et al., 1998) and triggering cellular apoptosis (Mishra et al., 2007). The basic domain (BD), rich in arginines regulates several important biological functions of Tat. These functions include nuclear localization of Tat, crossing membranes while entering or exiting the cell, binding to the uridine-rich bulge motif in the HIV TAR mRNA, and for dimerization of Tat.

Optimization of Vaccine Performance by Incorporating Diverse Molecular Strategies:

A wide range of molecular strategies have been employed to enhance performance of different types of vaccines. The strategies encompass an indeed wide array of strategies to improve protein expression, transcript stabilization, antigen processing and presentation, antigen delivery, coadministration of immune modulatory factors, recruiting innate immune components and many more. Reviewing all these components is beyond the scope of this section. Engineering the pan antigen DR epitope (PADRE), a universal HLA DR binding peptide (Alexander et al., 1994b), or other T-helper epitopes into antigens is one of the molecular strategies extensively used by many groups to enhance antigen-specific immune responses (Alexander et al., 1998). Given that peptide antigens are less immunogenic, PADRE epitope has been widely used to enhance immunogenicity of this form of vaccines (Beebe et al., 2007; Decroix et al., 2002; Fitzmaurice et al., 1996; Hsu et al., 1999; Olszewska et al., 2000), including that of HIV-1 env (Belyakov et al., 1998). Use of T-helper epitope into protein vaccines is less common although some examples are available (Greenstein et al., 1992; Rosa et al., 2004). Carbohydrate vaccines, derived from pathogenic organisms, that are least immunogenic intrinsically too shown to become immunogenic after conjugating such substrates to PADRE epitope (Alexander et al., 2004; Belot et al., 2005). Use of PADRE for mucosal vaccines has been documented (Decroix et al., 2002; Belyakov et al., 1998). A large quantum of effort has been directed against diverse type of cancers by generating cancer-specific peptides or antigens that are molecularly linked to T-helper epitopes (Beebe et al., 2007; Mansour et al., 2007; Stevenson et al., 2004b; van Bergen et al., 2000). T-helper epitopes have been engineered into DNA vaccines to augment their performance against viral infections (Hsu et al., 1999; Gao et al., 2004; Hung et al., 2007; Kim et al., 2007), including HIV-1 (Gorse et al., 2008; Newman et al., 2002). Polyclonal antisera with high antibody titers were raised in experimental animals against more than a hundred different antigens when these antigens were expressed as chimeras of PADRE epitope suggesting generic and wide application of T-help recruitment to a broad range of antigens (Chambers and Johnston, 2003). Recruitment of T-help through PADRE T-helper epitope has also been documented against parasite infections (Rosa et al., 2004), and even auto-immune disorders like Alzheimer's (Agadjanyan et al., 2005) or experimental autoimmune encephalitis (Uyttenhove et al., 2004).

Limitations of the Existing Tat Vaccines:

Despite all its merits, initial attempts of Tat vaccine met with limited success to the extent that there were doubts as per the rationale of Tat as a candidate vaccine. The primary reason why Tat vaccine did not yield expected results is because all the previous strategies ignored the basics while designing vaccines. Several technical challenges must be addressed before expecting Tat to function as a preventive or therapeutic vaccine. Some of the important limitations of the Tat vaccines can be broadly classified into three categories which have been described briefly below (a) poor immune response to Tat, (b) safety concerns since Tat is a toxin and an immunomodulator and (c) restricted antigen presentation as a protein.

(a) Tat is Non-Immunodominant:

Tat is a small nuclear protein that lacks potential T-helper epitopes. Although T-helper epitopes have been mapped in Tat (Blazevic et al., 1993; Ramakrishna et al., 2004; Ranki et al., 1997; Silvera et al., 2002), in natural infection, several lines of evidence suggest that these T-helper epitopes may not be strong enough. Only a fraction, 10-15% (data from JNCASR laboratory), of the seropositive subjects make anti-Tat humoral immune response (Krone et al., 1988; Reiss et al., 1990; Wieland et al., 1990). Of these subjects, only a minority show isotope switching to IgG indicating lack of efficient T-help (Venkatesh P K et al, manuscript in preparation). Likewise, cell-mediated immune responses to Tat were also shown to be scarce in natural infection (Borrow et al., 1994; Goulder et al., 2001; Lieberman et al., 1997; Masemola et al., 2004; Lamhamedi-Chemadi et al., 1992). The non-immunodominant nature of Tat must be an intrinsic property of Tat given that in experimental immunization too strong immune responses are not seen in primate (Putkonen et al., 1998; Belliard et al., 2005; Pauza et al., 2000) or human (Calarota et al., 1999; Hejdeman et al., 2004) studies. Non-availability of sufficient quantity of Tat in extra-cellular milieu could also be a contributory factor for non-immunodominant nature of Tat in natural infection. Although Tat is believed to be secreted extracellularly (eTat), the data in support of this hypothesis are scanty and wanting.

The foregoing suggests that molecular strategies are required to enhance immune responses induced by Tat for this antigen ever to become a candidate vaccine. Nearly all the previous attempts ignored this critical issue and used Tat as a protein, toxoid or DNA without means to enhance immune response.

(b) Tat being a Toxin Raises Safety Concerns:

As an extracellular viral factor, eTat is believed to possess pleiotropic effects on host cells and host immune system to enhance viral pathogenesis and infectivity. Some of these properties of eTat could have serious consequences especially in immune-compromised subjects (Huigen et al., 2004).

i. Latent virus activation: eTat could activate latent viruses thus contributing to spreading of the viral infection.
  ii. Apoptosis of the lymphocytes: eTat could program uninfected T-lymphocytes (Li et al., 1995), B-cells (Huang et al., 1997) and monocytes, to commit to apoptosis thus increasing the chances immune-suppression in HIV infected subjects. Tat can also inhibit NK cell function contributing to NK cell dysfunction (Zocchi et al., 1998)
  iii. Coreceptor upregulation: Tat can upregulate expression of coreceptors CCR5 and CXCR4 on target T-cells thus increasing the chances of viral infection (Huang et al., 1998). Likewise, Tat can modulate expression of a broad range of host genes with serious consequences for the host (Giacca, 2004).
  iv. Neuropathogenesis: Direct exposure of neurons and astrocytes to Tat is known to enhance cell death leading to neurologic consequences including enhanced dementia (Nath et al., 1998; Mishra et al., 2007).
  v. Perturbing cytokine homeostasis: Tat can induce cells of diverse phenotype to secrete cytokines and/or chemokines thereby actively perturbing the cytokine homeostasis in the body and consequently contributing to overall immune-suppression (Lafrenie et al., 1997; Nath et al., 1999).

vi. Immunosuppression: Tat activates TNF-α secretion from macrophages leading to immune-suppression (Zagury et al., 1998a) or through TGF-β (Reinhold et al., 1999). Tat could directly inhibit T-cell proliferation (Zagury et al., 1998a; Viscidi et al., 1989). Coexpression of Tat inhibited immune responses to env through the mediation of IL-10 activation (Gupta et al., 2008). In contrast, coexpression of Tat was shown to broaden immune recognition of HIV-1 gag and env demonstrating adjuvant properties (Gavioli et al., 2008). Although Tat is also known to be an immunoactivator (Fanales-Belasio et al., 2002; Gavioli et al., 2004), the conditions that regulate the fine balance between these contradictory functions of Tat are not well understood.

Tat Vaccine Controversy:

The recent controversy around the Tat vaccine developed by Dr. Barbara Ensoli's group in Italy revolves essentially around these safety concerns of Tat (Cohen, 2007) and Controversy Over European Framework Programme AIDS Vaccines (ISIS Press Release Dec. 10, 2007) (http://www.i-sis.org.uk/ControversyAIDSvaccines.php). The vaccine developed by this group consists of the functional Tat protein that could have potential hazards associated for human use (Ensoli et al., 2006). No strategies have been employed to answer the question of safety of this Tat vaccine candidate.

Tat Toxoid and Other Inactive Forms of Tat:

Attempts have been made to formulate Tat protein as a toxoid by chemical treatment (Gringeri et al., 1998; Le Buanec and Bizzini, 2000). Tat toxoid was shown to be safe and also generated moderate immune responses in humans (Gringeri et al., 1998; Gringeri et al., 1999; Noonan et al., 2003; Moreau et al., 2004) and in primates (Pauza et al., 2000; Richardson et al., 2002; Silvera et al., 2002). Although several studies demonstrated immunogenicity of Tat toxoid, often comparable to the Tat protein, evidence also exists that Tat toxoid may generate qualitatively different immune response as compared to the native antigen (Tikhonov et al., 2003; Yang et al., 2003). However, native, but not oxidized, Tat promoted maturation of monocyte-derived dendritic cells and efficient antigen presentation from them suggesting that functional Tat could be a superior vaccine candidate than the attenuated forms (Fanales-Belasio et al., 2002). Additionally, native Tat protein also modulated the subunit composition of the immunoprotasomes leading to augmented antigen processing (Gavioli et al., 2004; Remoli et al., 2006). Tat mutants inactive for transactivation have been tested in mice but no progress reported beyond this animal model (Caselli et al., 1999; Mayol et al., 2007). Oxidized Tat was proposed to be a safe format for vaccination (Cohen et al., 1999).

(c) Tat as a Protein or Toxoid May not Access the MHC Class-I Compartment Efficiently:

Tat predominantly is an intra-cellular protein although experimental evidence suggests its secretion into the body fluids (Chang et al., 1997). Further, Tat is not exposed on the surface of the virus. Cell-mediate immune responses to Tat, therefore, should be the predominant component to restrict viral expansion in vivo although antibodies do play a significant role. Majority of the previous strategies used Tat as a recombinant protein or toxoid in primate immunization studies (Cafaro et al., 1999; Ensoli and Cafaro, 2000; Pauza et al., 2000; Richardson et al., 2002; Silvera et al., 2002; Tikhonov et al., 2003) or human clinical trial (Ensoli et al., 2006). As proteins, these antigens are less likely to access the MHC-I compartment to stimulate efficient anti-viral cell-mediated immune response. Although Tat protein is known to be cross-presented to MHC-I compartment (Kim et al., 1997), it not likely to be a predominant pathway of antigen presentation. The absence of strong cellular immune responses in the previously reported studies underlies the importance of targeting Tat to MHC-I compartment for vaccine development. Recombinant viruses efficiently introduce encoded antigens into MHC-I pathway, immune intervention, however, could interfere with immune responses (de et al., 2008; Willis et al., 2006). Further, preexisting immune response to the viral vector is a significant problem that limits recombinant vector-mediated antigen delivery (Bangari and Mittal, 2006). DNA vaccine, therefore, is an ideal medium for antigen delivery given that this form of vaccination can stimulate strong immune responses akin to viral vectors. DNA vaccines, however, have several technical challenges that must be addressed before they could be used as a reliable medium of immunization (Dean et al., 2005).

This project proposal enlists several potentially important molecular and immunologic features to address several critical challenges of the Tat vaccine as discussed above.

OBJECTIVE OF THE INVENTION

The main objective of the present invention is to obtain non toxic, immunogenic viral Tat DNA sequences comprising N-terminal region, Cysteine rich domain (CRD), Core domain, Basic domain (BD), C-terminal region and Exon II region, wherein the Tat Sequence is rendered non toxic and immunogenic by insertion of T-Helper Epitope into the Cysteine-rich domain, or Basic domain or Core domain of said Tat DNA sequence, optionally along with insertion of a synthetic Intron between C-terminal region and Exon II region of the Tat DNA Sequence.

Another objective of the present invention is to obtain an intron sequence.

Yet another objective of the present invention is to obtain a process to obtain a non toxic, immunogenic viral Tat DNA sequence.

Still another objective of the present invention is to obtain an expression vector having a non toxic, immunogenic viral Tat DNA sequence.

Still another objective of the present invention is to obtain a vaccine comprising non toxic, immunogenic viral Tat DNA sequence in phosphate buffer saline.

Still another objective of the present invention is to obtain a method of obtaining a vaccine comprising non toxic, immunogenic viral Tat DNA sequence.

Still another objective of the present invention is to obtain a kit having a vaccine comprising non toxic, immunogenic viral Tat DNA sequence.

STATEMENT OF THE INVENTION

Accordingly, the present invention relates to a viral Tat DNA sequence comprising N-terminal region, Cysteine rich domain (CRD), Core domain, Basic domain (BD), C-terminal region and Exon II region, wherein the Cysteine rich domain (CRD) is disrupted by insertion of Pan HLA-DR Binding epitope (PADRE) as represented by Sequence Id No 1, or by $Pol_{711}$ epitope as represented by Sequence Id No. 2; a viral Tat DNA sequence comprising N-terminal region, Cysteine rich domain (CRD), Core domain, Basic domain (BD), C-terminal region and Exon II region, wherein the Basic Domain (BD) is disrupted by insertion of Pan HLA-DR Binding epitope (PADRE) as represented by Sequence Id No 3, or by $Pol_{711}$ epitope as represented by Sequence Id No. 4; a viral Tat DNA sequence comprising N-terminal region, Cysteine rich domain (CRD), Core domain, Basic domain (BD), C-terminal region and Exon II region, wherein the Cysteine rich domain (CRD) is disrupted by insertion of Pan HLA-DR Binding epitope (PADRE) and Basic Domain (BD) is disrupted by insertion of $Pol_{711}$ as represented by Sequence Id No 5; a viral Tat DNA sequence comprising N-terminal region, Cysteine rich domain (CRD), Core domain, Basic domain (BD), C-terminal region and Exon II region, wherein the Cysteine rich domain (CRD) is disrupted by insertion of $Pol_{711}$ epitope and Basic Domain (BD) is disrupted by insertion of Pan HLA-DR Binding epitope (PADRE) as represented by Sequence Id No 6; a viral Tat DNA sequence comprising N-terminal region, Cysteine rich domain (CRD), Core domain, Basic domain (BD), C-terminal region and Exon II region, wherein a synthetic Intron is inserted between C-terminal region and Exon II region of the Tat DNA sequence as represented by Sequence Id No. 7; an Intron sequence as represented by Sequence Id No. 8; a viral Tat DNA sequence comprising N-terminal region, Cysteine rich domain (CRD), Core domain, Basic domain (BD), C-terminal region and Exon II region, wherein synthetic Intron of Sequence Id No. 8 is inserted between C-terminal region and Exon II region of sequences selected from a group comprising Sequence Id Nos 1 or 2 or 3 or 4 or 5 or 6; a non toxic, immunogenic viral Tat DNA sequence comprising N-terminal region, Cysteine rich domain (CRD), Core domain, Basic domain (BD), C-terminal region and Exon II region, wherein the Tat Sequence is rendered non toxic and immunogenic by insertion of T-Helper Epitope into the Cysteine-rich domain, or Basic domain or Core domain of said Tat DNA sequence, optionally along with insertion of a synthetic Intron between C-terminal region and Exon II region of the Tat DNA Sequence; a process to obtain a non toxic, immunogenic viral Tat DNA sequence, wherein the Tat DNA Sequence is rendered non toxic and immunogenic by insertion of T-Helper Epitope into Cysteine-rich domain, or Basic domain or Core domain of said Tat DNA sequence, optionally along with insertion of a synthetic intron between C-terminal and Exon 2 of the Tat DNA Sequence, said method comprising steps of: a) amplifying full length Tat DNA to obtain PCR products with inserted T-Helper epitope into CRD, BD or Core domain of the amplified Tat DNA, optionally along with synthetic Intron between the C-terminal region and Exon II region of the Tat DNA sequence, b) cloning of PCR products with insertions of step (a) into a mammalian expression cassettes or plasmid vectors, and c) insertion of expression cassettes or plasmid vectors of step (b) into a suitable host for expression to obtain said Tat DNA sequence; an expression vector having a non toxic, immunogenic viral Tat DNA sequence comprising N-terminal region, Cysteine rich domain (CRD), Core domain, Basic domain (BD), C-terminal region and Exon II region, wherein the Tat Sequence is engineered by insertion of T-Helper Epitope into the Cysteine-rich domain, or Basic domain or Core domain of said Tat DNA sequence, optionally along with insertion of a synthetic Intron between C-terminal region and Exon II region of the Tat DNA Sequence, wherein said expression vector comprises ubiquitous cellular promoters including EF-1α, β-Actin, EGR1, eIF4A1, FerH, FerL, GAPDH, GRP78, GRP94, HSP70, β-Kin, PGK-1, ROSA, Ubiquitin B, ubiquitin C and many others, preferably EF-1α promoter or any combination thereof; an Elongation factor-1alpha (EF-1α) cellular promoter gene construct as represented in Sequence Id No. 9 or 10 or 11 or 12 or 13 or 14, wherein different fragments within Intron1 of the original full length promoter sequence is deleted to obtain said promoter gene constructs; a process to obtain an Elongation factor-1alpha (EF-1α) cellular promoter gene construct as represented in Sequence Id No. 9 or 10 or 11 or 12 or 13 or 14, wherein different fragments within Intron1 of the original full length promoter sequence is deleted to obtain said promoter gene constructs, said method comprising step of using Restriction Digestion to delete different fragments within Intron 1 to obtain said gene constructs; a vaccine comprising non toxic, immunogenic viral Tat DNA sequence in phosphate buffer saline, wherein said Tat DNA comprise N-terminal region, Cysteine rich domain (CRD), Core domain, Basic domain (BD), C-terminal region and Exon II region, wherein the Tat Sequence is rendered non toxic and immunogenic by insertion of T-Helper Epitope into the Cysteine-rich domain, or Basic domain or Core domain of said Tat DNA sequence, optionally along with insertion of a synthetic Intron between C-terminal region and Exon II region of the Tat DNA Sequence; a method of obtaining a vaccine comprising non toxic, immunogenic viral Tat DNA sequence comprising of N-terminal region, Cysteine rich domain (CRD), Core domain, Basic domain (BD), C-terminal region and Exon II region, wherein the Tat Sequence is rendered non toxic and immunogenic by insertion of T-Helper Epitope into the Cysteine-rich domain, or Basic domain or Core domain of said Tat DNA sequence, optionally along with insertion of a synthetic Intron between C-terminal region and Exon II region of the Tat DNA Sequence, said method comprising step of dissolving said viral Tat DNA into phosphate buffer saline to obtain the vaccine; and a kit having a vaccine comprising non toxic, immunogenic viral Tat DNA sequence in phosphate buffer saline, wherein said Tat DNA comprise N-terminal region, Cysteine rich domain (CRD), Core domain, Basic domain (BD), C-terminal region and Exon II region, wherein the Tat Sequence is rendered non toxic and immunogenic by insertion of T-Helper Epitope into the Cysteine-rich domain, or Basic domain or Core domain of said Tat DNA sequence, optionally along with insertion of a synthetic Intron between C-terminal region and Exon II region of the Tat DNA Sequence.

BRIEF DESCRIPTION OF ACCOMPANYING DRAWINGS

FIG. 1: pCMV-$Tat_{co}$ (full-length, natural codons, CMV promoter) vector construct.

Figure 2:
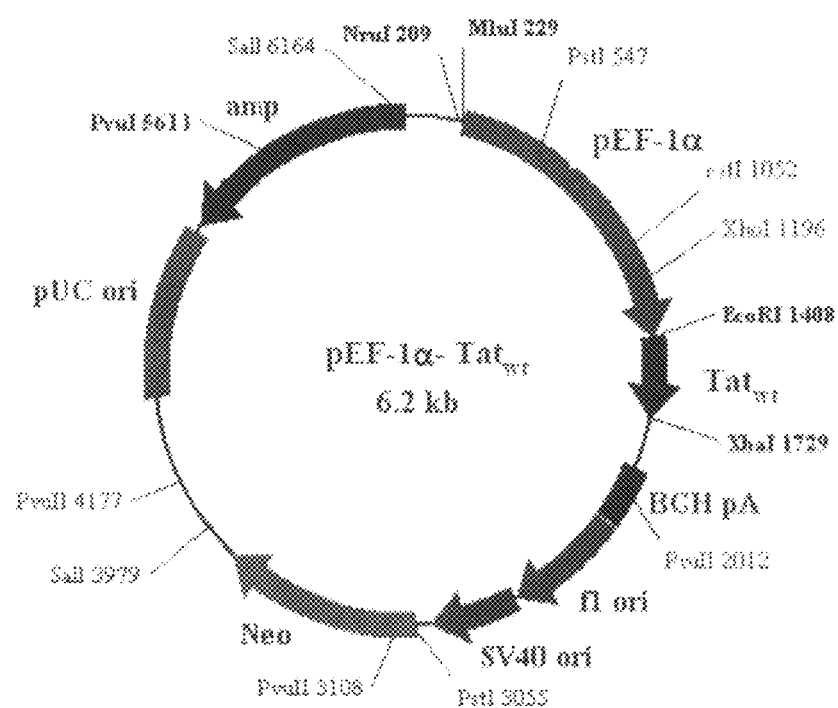

FIG. 2: pEF-1α-$Tat_{wt}$ (full-length, natural codons, EF-1α promoter) vector construct.

Figure 3:
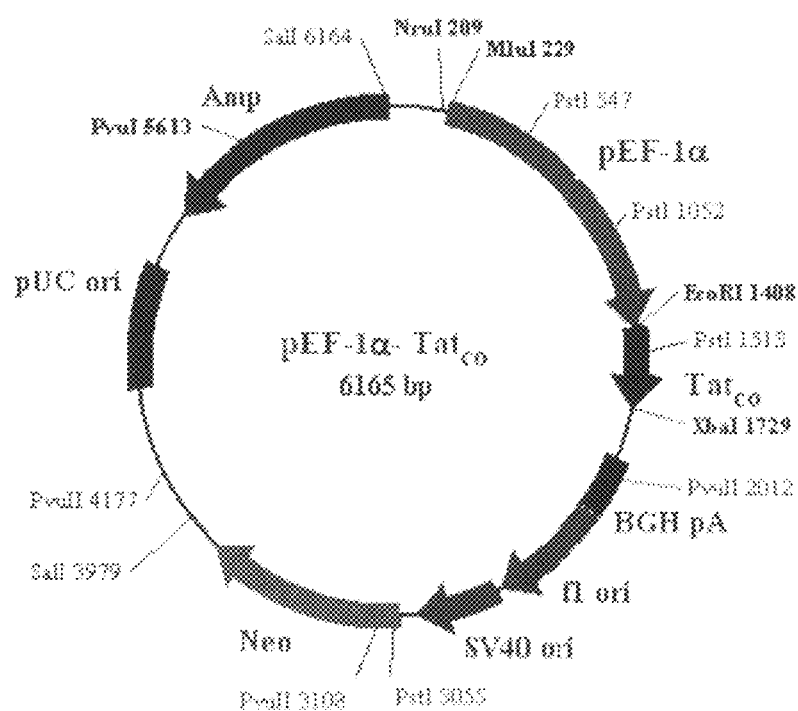

FIG. 3: pEF-1α-$Tat_{co}$ (full-length, optimized codons, EF-1α promoter) vector construct.

Figure 4:
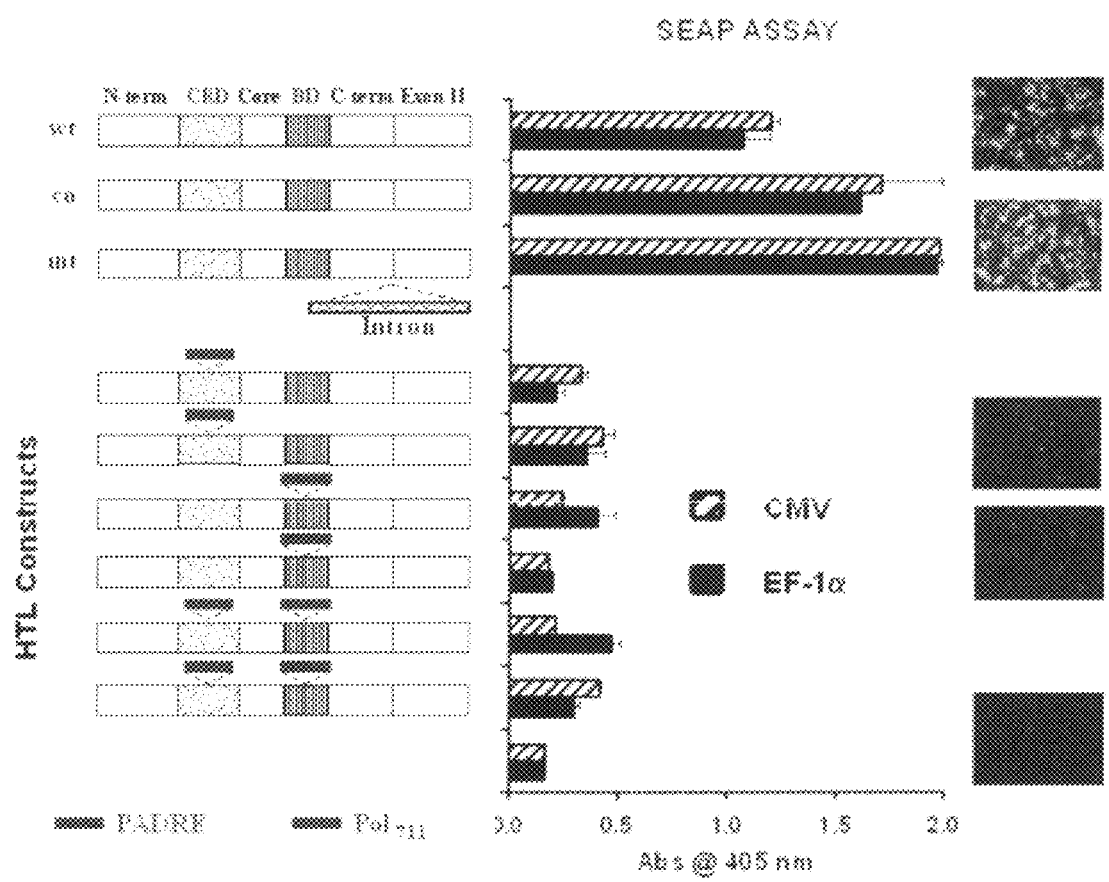

FIG. 4: Various HTL constructs and their respective expression results obtained with Transactivation assay.

Figure 5:
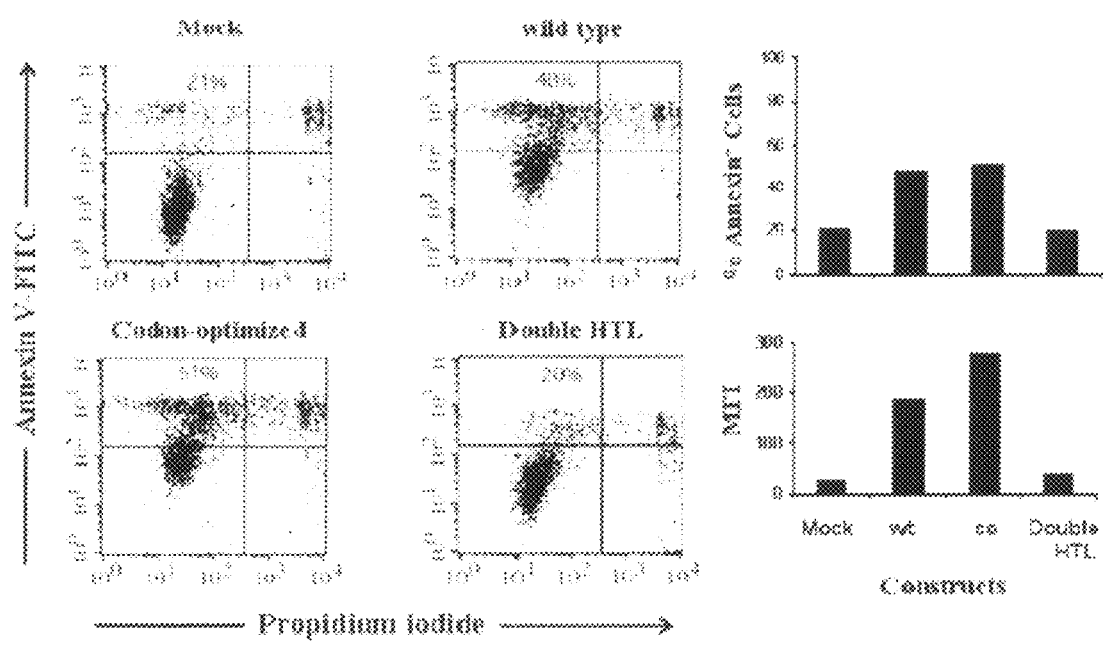

FIG. 5: Results obtained from Apoptosis assay

Figure 6:
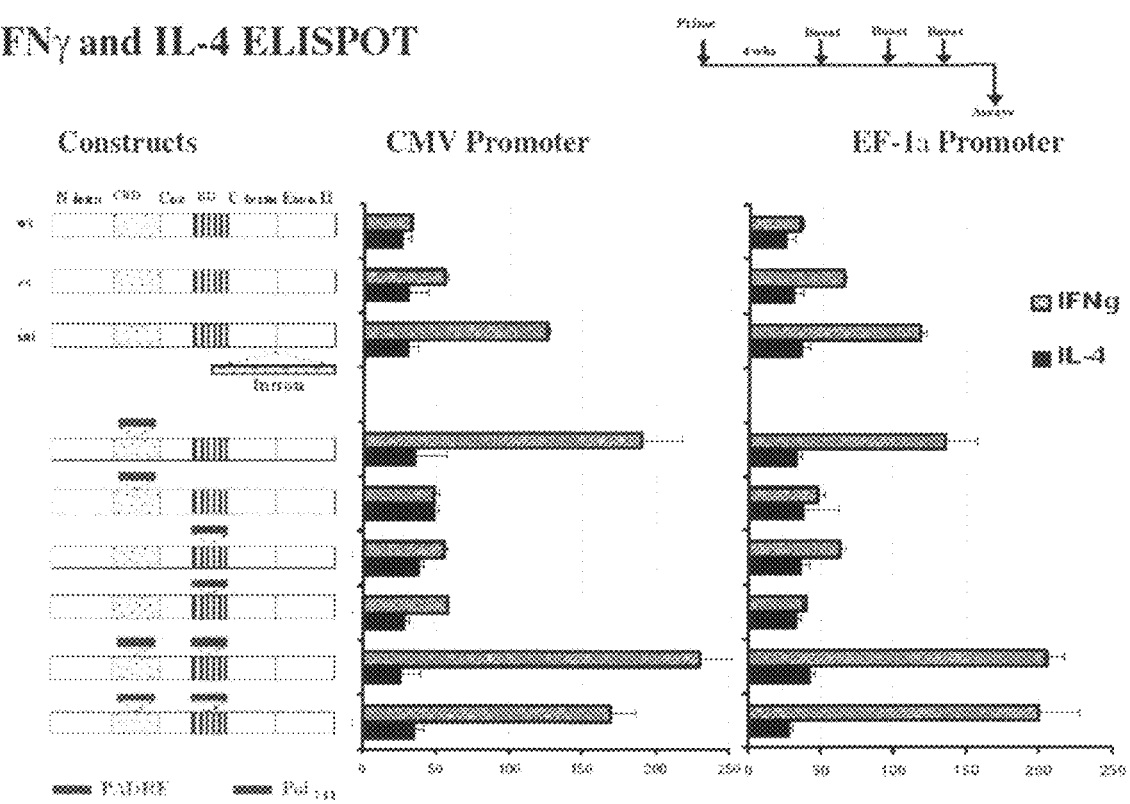

FIG. 6: Gene constructs and promoters used, along with their results obtained from ELISPOT assay.

FIG. 7: Results obtained from SEAP assay and GFP analysis for Intron engineering.

FIG. 8: Results obtained from ELISPOT assay and Lymphoproliferation assay for Intron engineering.

FIG. 9: Viral Load results obtained for Intron engineered Tat in mice.

Figure 10:
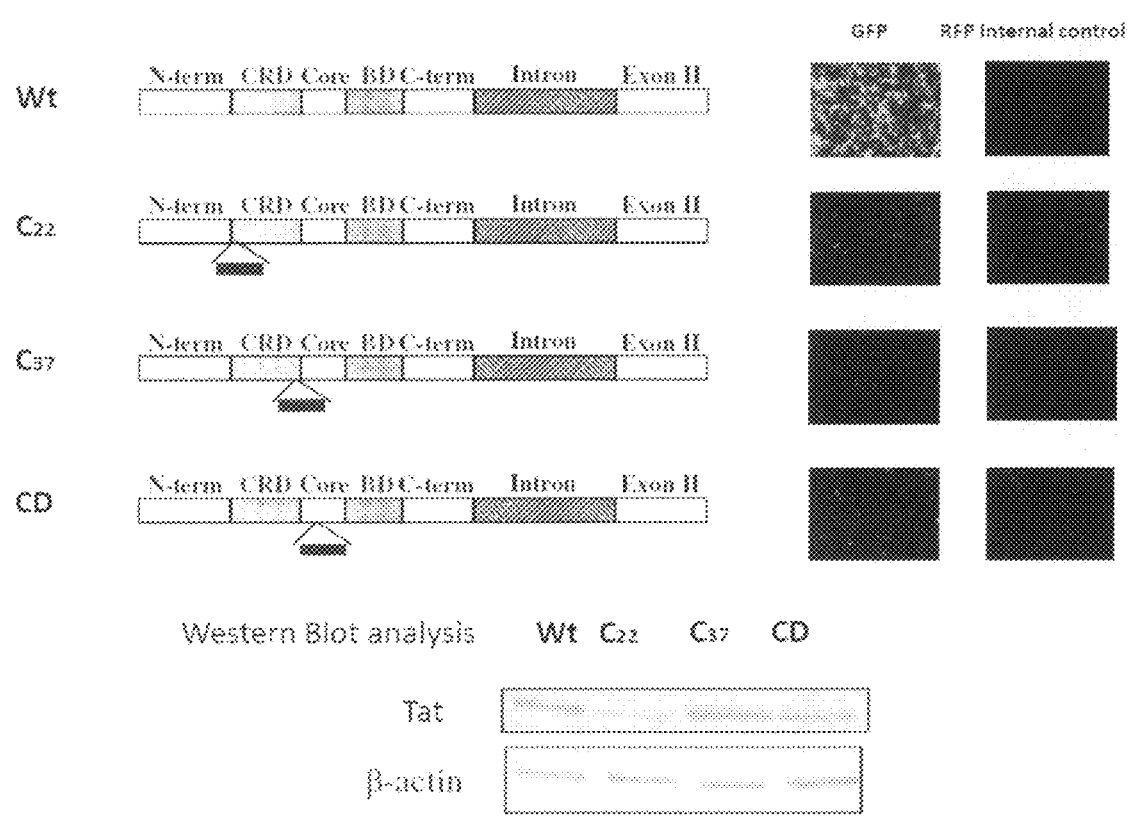

FIG. 10: Gene constructs and results obtained for Intron and HTL engineered together in Tat.

Figure 11:
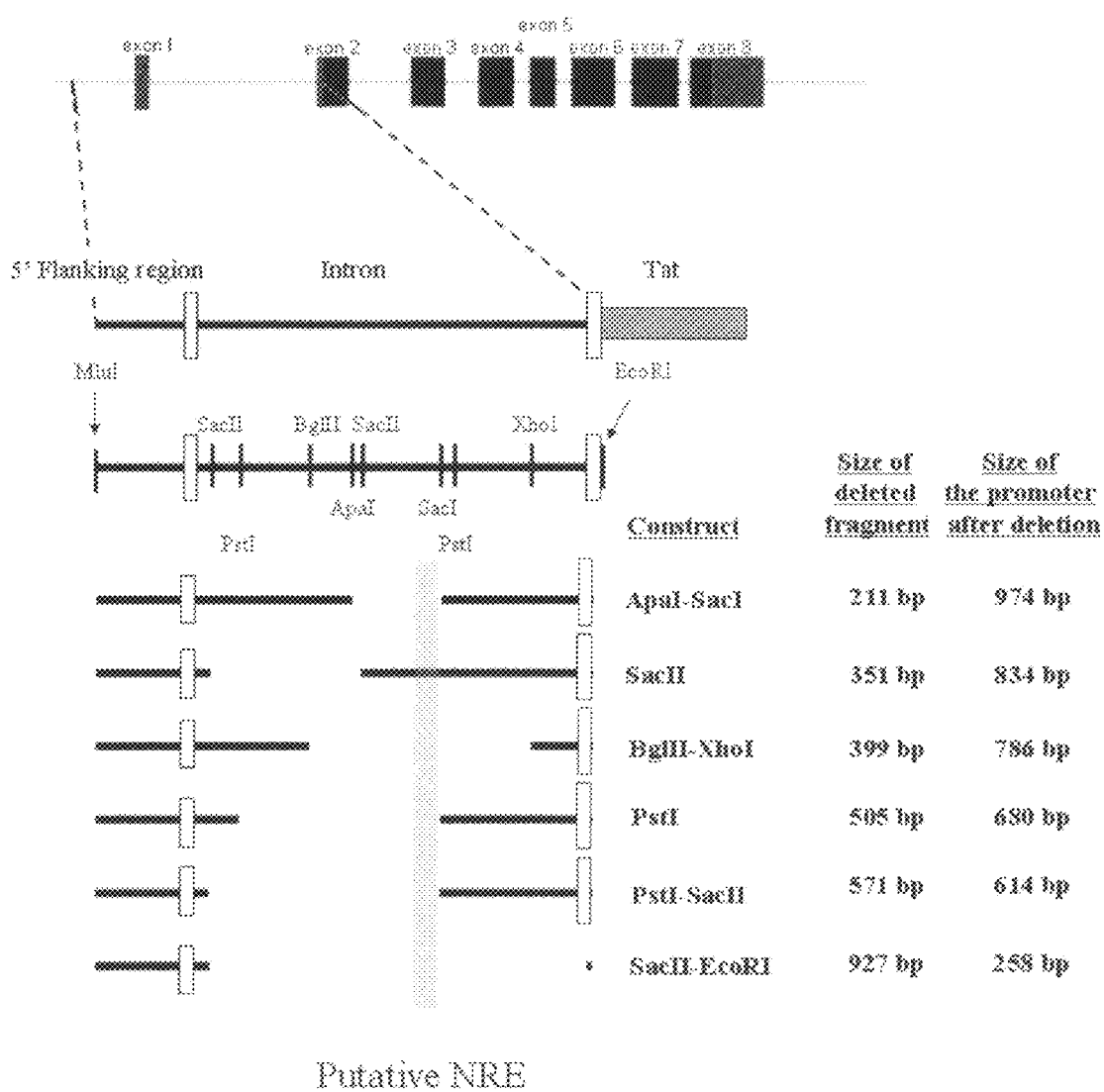

FIG. 11: Schematic representation of the EF-1α promoter deletion constructs.

Figure 11A:
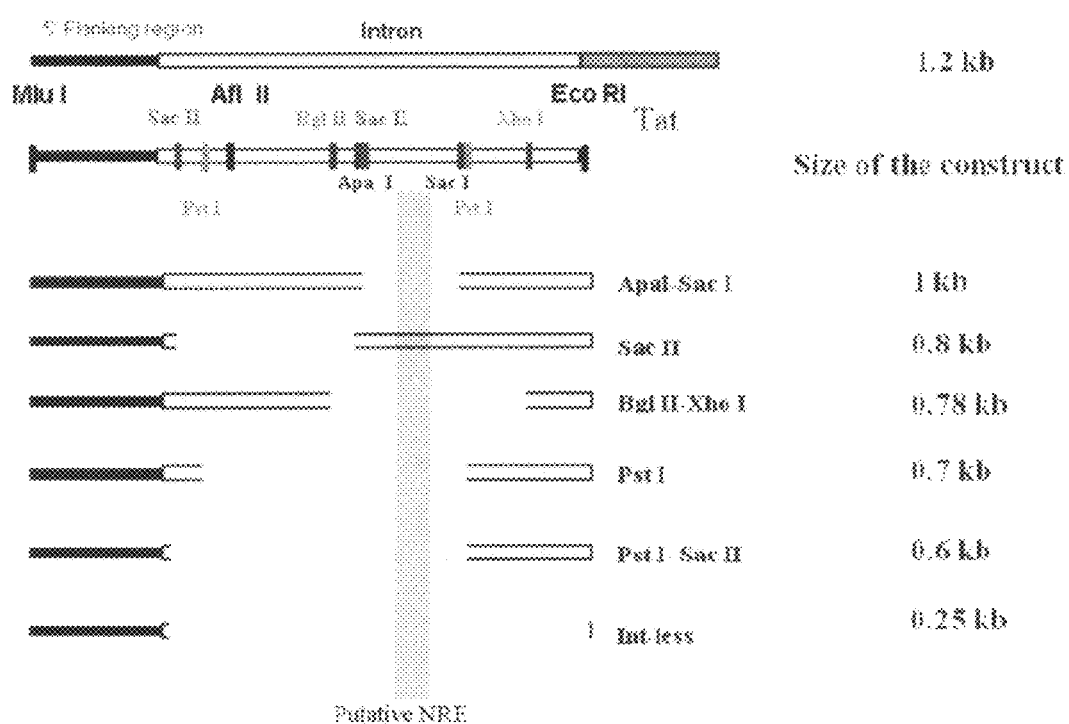

FIG. 11a: The EF-1α promoter deletion constructs and identification of putative NRE regions.

FIG. 12: Results obtained from GFP analysis and Western Blot analysis for the gene expression by EF-1α variant promoters.

Figure 13:
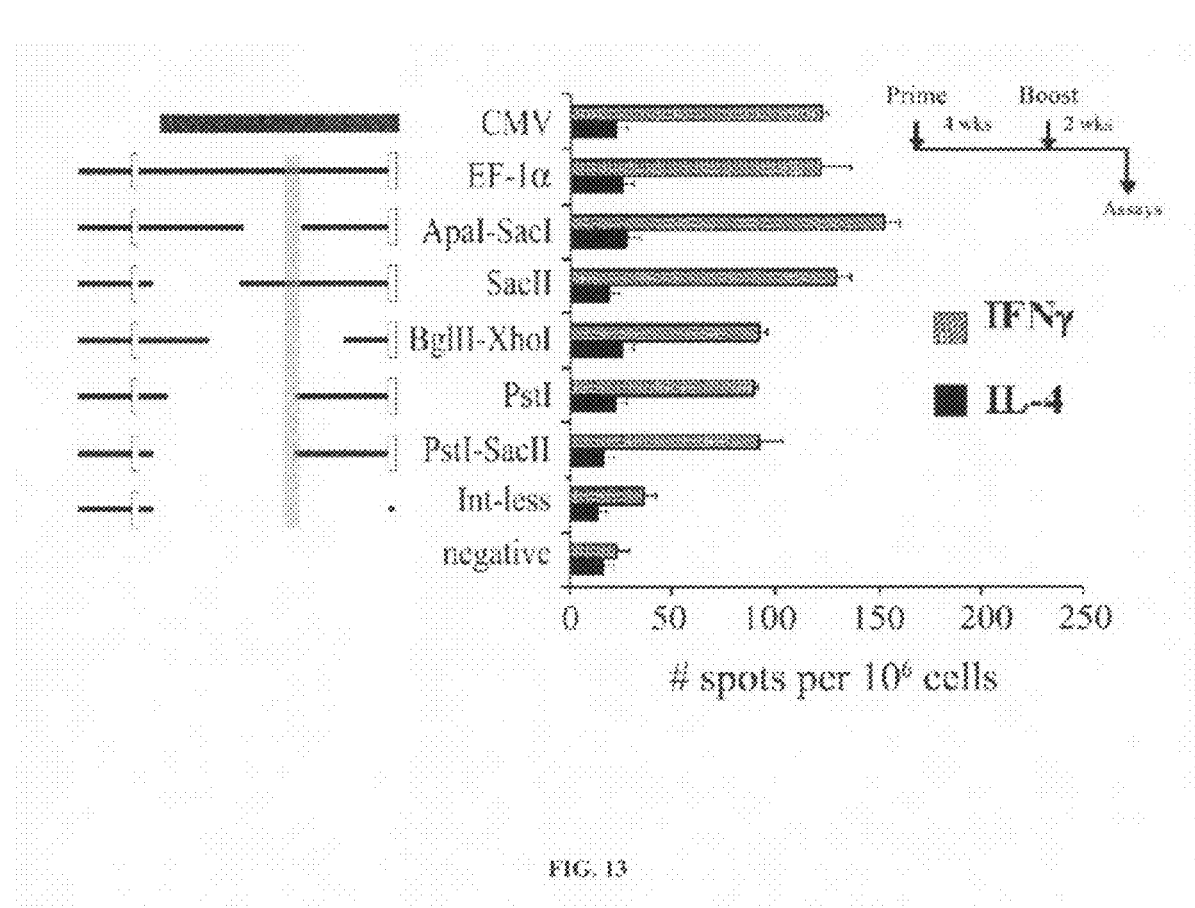

FIG. 13: EF-1α promoter deletion constructs and results obtained for induction of high quality immune response.

Figure 14:
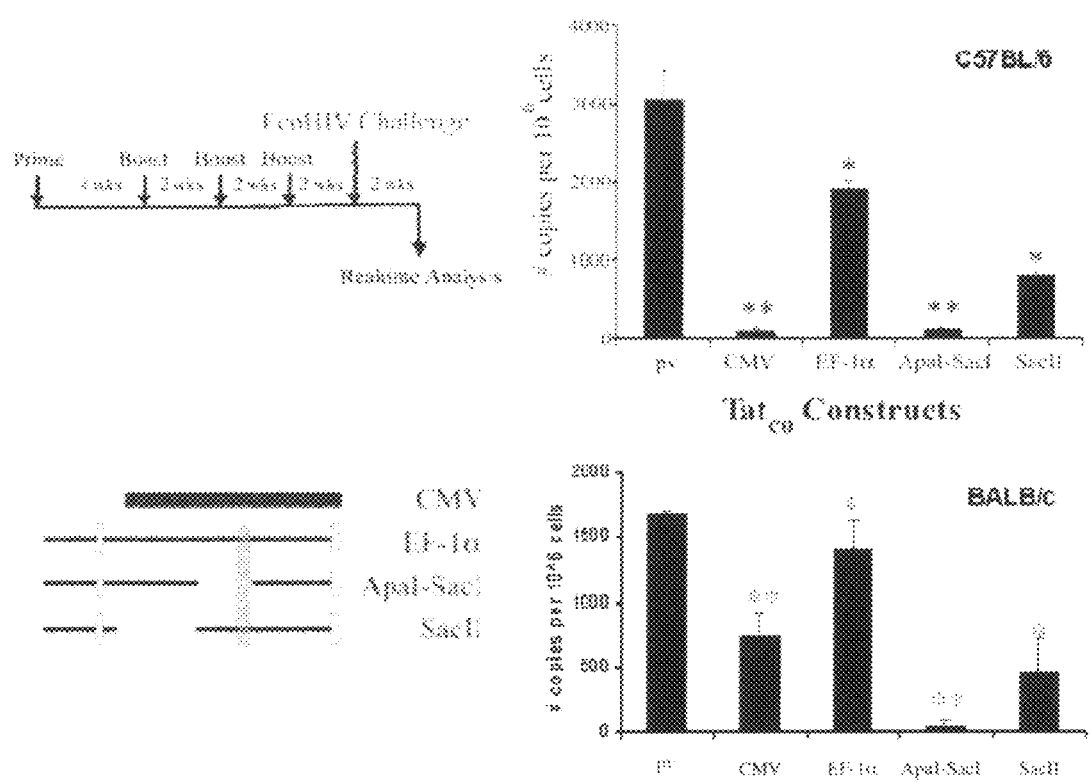
Figure 18:
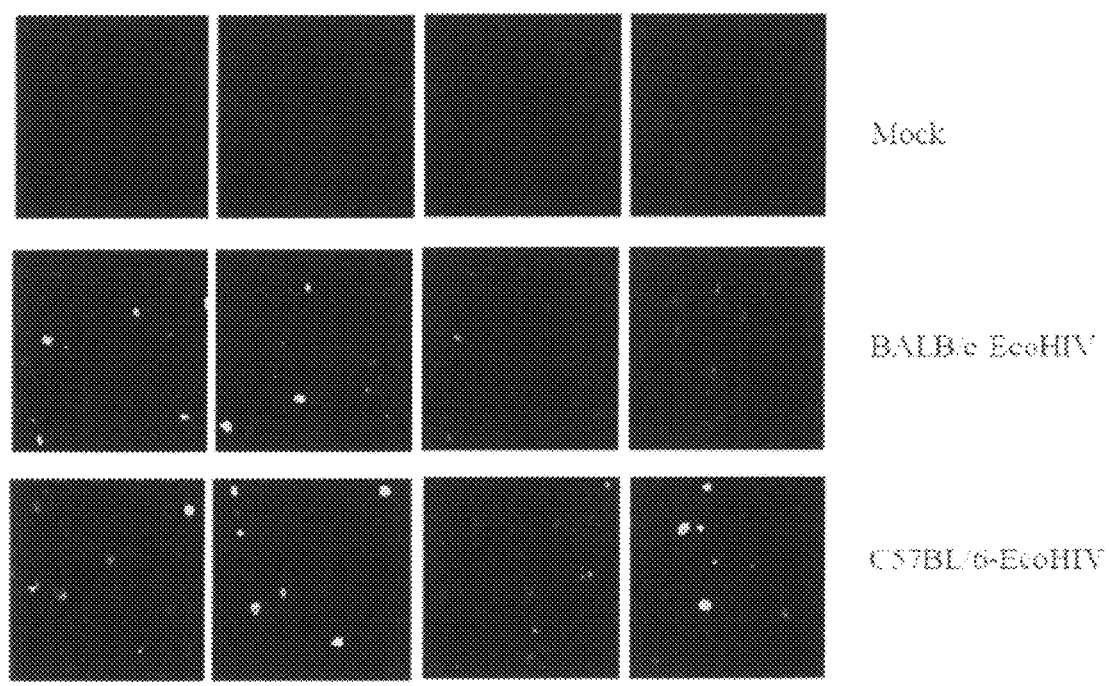

FIG. 14: Results obtained for Tat immunization and controlling of viral load by EF-1α variant promoter constructs.

FIG. 15: Direct immunofluorescence of mouse splenocytes for intracellular p24.

Figure 16:
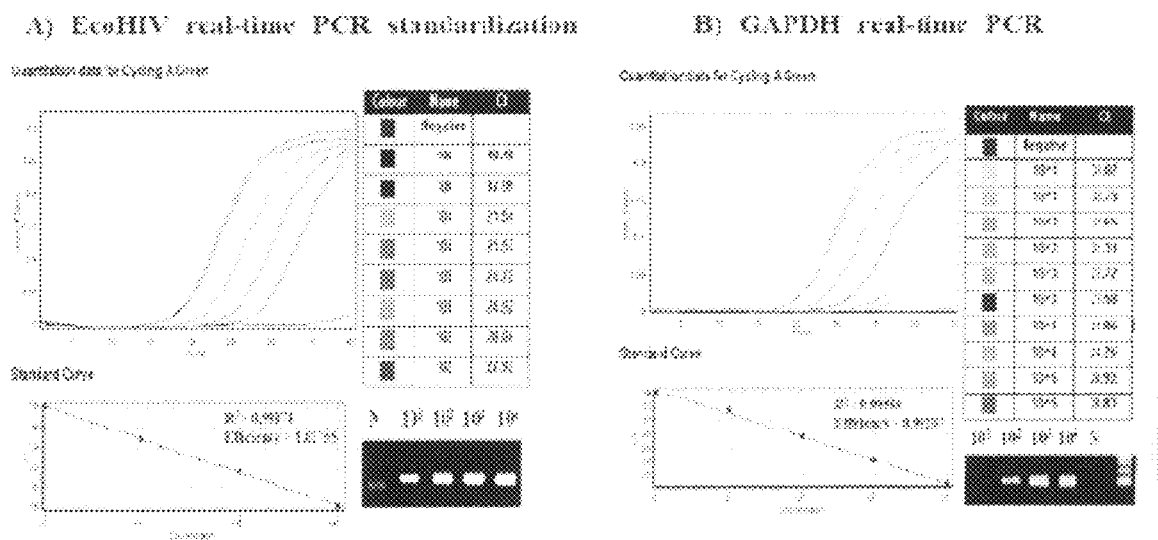

FIG. 16: Standardization of real-time PCR for EcoHIV and GAPDH using plasmid templates.

DETAILED DESCRIPTION OF THE INVENTION

The present invention relates to a viral Tat DNA sequence comprising N-terminal region, Cysteine rich domain (CRD), Core domain, Basic domain (BD), C-terminal region and Exon II region, wherein the Cysteine rich domain (CRD) is disrupted by insertion of Pan HLA-DR Binding epitope (PADRE) as represented by Sequence Id No 1, or by $Pol_{711}$ epitope as represented by Sequence Id No. 2.

The present invention relates to a viral Tat DNA sequence comprising N-terminal region, Cysteine rich domain (CRD), Core domain, Basic domain (BD), C-terminal region and Exon II region, wherein the Basic Domain (BD) is disrupted by insertion of Pan HLA-DR Binding epitope (PADRE) as represented by Sequence Id No 3, or by $Pol_{711}$ epitope as represented by Sequence Id No. 4.

The present invention relates to a viral Tat DNA sequence Comprising N-terminal region, Cysteine rich domain (CRD), Core domain, Basic domain (BD), C-terminal region and Exon II region, wherein the Cysteine rich domain (CRD) is disrupted by insertion of Pan HLA-DR Binding epitope (PADRE) and Basic Domain (BD) is disrupted by insertion of $Pol_{711}$ as represented by Sequence Id No 5.

The present invention relates to a viral Tat DNA sequence comprising N-terminal region, Cysteine rich domain (CRD), Core domain, Basic domain (BD), C-terminal region and Exon II region, wherein the Cysteine rich domain (CRD) is disrupted by insertion of $Pol_{711}$ epitope and Basic Domain (BD) is disrupted by insertion of Pan HLA-DR Binding epitope (PADRE) as represented by Sequence Id No 6.

The present invention relates to a viral Tat DNA sequence comprising N-terminal region, Cysteine rich domain (CRD), Core domain, Basic domain (BD), C-terminal region and Exon II region, wherein a synthetic Intron is inserted between C-terminal region and Exon II region of the Tat DNA sequence as represented by Sequence Id No. 7.

In another embodiment of the present invention, the Tat DNA is derived from diverse viral types selected from a group comprising subtypes and sub-subtypes of human and primate retroviruses including HIV-1, HIV-2 and SIV; HIV-1 types M, N and O; HIV-1 subtypes A to K; and various HIV-1 and HIV-2 recombinant forms including unique recombinant forms (URF) and circulating recombinant forms (CRF).

The present invention relates to an Intron sequence as represented by Sequence Id No. 8.

The present invention relates to a viral Tat DNA sequence comprising N-terminal region, Cysteine rich domain (CRD), Core domain, Basic domain (BD), C-terminal region and Exon II region, wherein synthetic Intron of Sequence Id No. 8 is inserted between C-terminal region and Exon II region of sequences selected from a group comprising Sequence Id Nos 1 or 2 or 3 or 4 or 5 or 6.

In another embodiment of the present invention, the Tat DNA is derived from diverse viral types selected from a group comprising subtypes and sub-subtypes of human and primate retroviruses including HIV-1, HIV-2 and SW; HIV-1 types M, N and O; HIV-1 subtypes A to K; and various HIV-1 and HIV-2 recombinant forms including unique recombinant forms (URF) and circulating recombinant forms (CRF).

The present invention relates to a non toxic, immunogenic viral Tat DNA sequence comprising N-terminal region, Cysteine rich domain (CRD), Core domain, Basic domain (BD), C-terminal region and Exon II region, wherein the Tat Sequence is rendered non toxic and immunogenic by insertion of T-Helper Epitope into the Cysteine-rich domain, or Basic domain or Core domain of said Tat DNA sequence, optionally along with insertion of a synthetic Intron between C-terminal region and Exon II region of the Tat DNA Sequence.

In another embodiment of the present invention, the Tat DNA is derived from diverse viral types selected from a group comprising subtypes and sub-subtypes of human and primate retroviruses including HIV-1, HIV-2 and SIV; HIV-1 types M, N and O; HIV-1 subtypes A to K; and various HIV-1 and HIV-2 recombinant forms including unique recombinant forms (URF) and circulating recombinant forms (CRF).

In yet another embodiment of the present invention, the T-helper epitope is selected from a group comprising Pan HLA-DR binding epitope (PADRE), and any other 'universal' T-helper epitopes including HIV-1 $Pol_{711}$, T-helper epitopes derived from diverse biological sources and artificially synthesized including toxins: *Clostridium botulinum* neurotoxin serotype A, Diththeria toxin, cholera toxin, and bacterial enterotoxins; immunodominant antigens: HIV antigens including gag, RT, Integrase, env, net Tat and Rev, hepatitis B surface antigen, core antigen and antigens of other organisms; heat-shock proteins and chaperone proteins: of mammals and microorganisms including viruses, bacteria, fungi and parasites; carrier proteins including keyhole limpet cyanine, bovine serum albumin, ovalbumin, *E. coli* maltose-binding protein, Riboflavin carrier protein, glycoprotein D carrier protein, and many others, preferably PADRE and $Pol_{711}$ or any combination thereof.

In still another embodiment of the present invention, the PADRE is derived from a group comprising tetanus toxoid, *Clostridium botulinum* neurotoxin serotype A, Diththeria toxin, cholera toxin and bacterial enterotoxins, preferably tetanus toxoid and said $Pol_{711}$ is derived from a group comprising HIV-1 polymerase, HIV antigens including gag, RT, Integrase, env, nef, Tat and Rev, preferably HIV-1 polymerase.

In still another embodiment of the present invention, the engineered Tat DNA sequence is non-toxic to host as a consequence of structural disruption of important domains of Tat including CRD, BD and core domain of the virus.

The present invention relates to a process to obtain a non toxic, immunogenic viral Tat DNA sequence, wherein the Tat DNA Sequence is rendered non toxic and immunogenic by insertion of T-Helper Epitope into Cysteine-rich domain, or Basic domain or Core domain of said Tat DNA sequence, optionally along with insertion of a synthetic intron between C-terminal and Exon 2 of the Tat DNA Sequence, said method comprising steps of:

a) amplifying full length Tat DNA to obtain PCR products with inserted T-Helper epitope into CRD, BD or Core domain of the amplified Tat DNA, optionally along with synthetic Intron between the C-terminal region and Exon II region of the Tat DNA sequence,
b) cloning of PCR products with insertions of step (a) into a mammalian expression cassettes or plasmid vectors, and
c) insertion of expression cassettes or plasmid vectors of step (b) into a suitable host for expression to obtain said Tat DNA sequence.

In another embodiment of the present invention, the Tat DNA is derived from diverse viral types selected from a group comprising subtypes and sub-subtypes of human and primate retroviruses including HIV-1, HIV-2 and SIV; HIV-1 types M, N and O; HIV-1 subtypes A to K; and various HIV-1 and HIV-2 recombinant forms including unique recombinant forms (URF) and circulating recombinant forms (CRF).

In yet another embodiment of the present invention, the T-helper epitope is selected from a group comprising Pan HLA-DR binding epitope (PADRE), and any other 'universal' T-helper epitopes including HIV-1 $Pol_{711}$, T-helper epitopes derived from diverse biological sources and artificially synthesized including toxins: *Clostridium botulinum* neurotoxin serotype A, Diththeria toxin, cholera toxin, and bacterial enterotoxins; immunodominant antigens: HIV antigens including gag, RT, Integrase, env, nef, Tat and Rev, hepatitis B surface antigen, core antigen and antigens of other organisms; heat-shock proteins and chaperone proteins: of mammals and microorganisms including viruses, bacteria, fungi and parasites; carrier proteins including keyhole limpet cyanine, bovine serum albumin, ovalbumin, *E. coli* maltose-binding protein, Riboflavin carrier protein, glycoprotein D carrier protein, and many others, preferably PADRE and $Pol_{711}$ or any combination thereof.

In still another embodiment of the present invention, the PADRE is derived from a group comprising tetanus toxoid, *Clostridium botulinum* neurotoxin serotype A, Diththeria toxin, cholera toxin, bacterial enterotoxins and many others, preferably tetanus toxoid and said $Pol_{711}$ is derived from a group comprising HIV-1 polymerase, HIV antigens including gag, RT, Integrase, env, nef, Tat, Rev and other proteins, preferably HIV-1 polymerase.

The present invention relates to an expression vector having a non toxic, immunogenic viral Tat DNA sequence comprising N-terminal region, Cysteine rich domain (CRD), Core domain, Basic domain (BD), C-terminal region and Exon II region, wherein the Tat Sequence is engineered by insertion of T-Helper Epitope into the Cysteine-rich domain, or Basic domain or Core domain of said Tat DNA sequence, optionally along with insertion of a synthetic Intron between C-terminal region and Exon II region of the Tat DNA Sequence, wherein said expression vector comprises ubiquitous cellular promoters including EF-1α, β-Actin, EGR1, eIF4A1, FerH, FerL, GAPDH, GRP78, GRP94, HSP70, β-Kin, PGK-1, ROSA, Ubiquitin B, ubiquitin C and many others, preferably EF-1α promoter or any combination thereof.

The present invention relates to an Elongation factor-1alpha (EF-1α) cellular promoter gene construct as represented in Sequence Id No. 9 or 10 or 11 or 12 or 13 or 14, wherein different fragments within Intron1 of the original full length promoter sequence is deleted to obtain said promoter gene constructs.

In another embodiment of the present invention, the cellular promoter gene constructs are used to express non toxic, immunogenic viral Tat DNA sequence present in a mammalian expression vector.

The present invention relates to a process to obtain an Elongation factor-1alpha (EF-1α) cellular promoter gene construct as represented in Sequence Id No. 9 or 10 or 11 or 12 or 13 or 14, wherein different fragments within Intron1 of the original full length promoter sequence is deleted to obtain said promoter gene constructs, said method comprising step of using Restriction Digestion to delete different fragments within Intron 1 to obtain said gene constructs.

In another embodiment of the present invention, the restriction digestion is carried out using sites selected from a group comprising of MluI, EcoRI, ApaI, SacI, SacII, BglII, XhoI or PstI or any combination thereof.

The present invention relates to a vaccine comprising non toxic, immunogenic viral Tat DNA sequence in phosphate buffer saline, wherein said Tat DNA comprise N-terminal region, Cysteine rich domain (CRD), Core domain, Basic domain (BD), C-terminal region and Exon II region, wherein the Tat Sequence is rendered non toxic and immunogenic by insertion of T-Helper Epitope into the Cysteine-rich domain, or Basic domain or Core domain of said Tat DNA sequence, optionally along with insertion of a synthetic Intron between C-terminal region and Exon II region of the Tat DNA Sequence.

In another embodiment of the present invention, the Tat DNA is derived from diverse viral types selected from a group comprising subtypes and sub-subtypes of human and primate retroviruses including HIV-1, HIV-2 and SIV; HIV-1 types M, N and O; HIV-1 subtypes A to K; and various HIV-1 and HIV-2 recombinant forms including unique recombinant forms (URF) and circulating recombinant forms (CRF).

In yet another embodiment of the present invention, the T-helper epitope is selected from a group comprising Pan HLA-DR binding epitope (PADRE), and any other 'universal' T-helper epitopes including HIV-1 $Pol_{711}$, T-helper epitopes derived from diverse biological sources and artificially synthesized including toxins: *Clostridium botulinum* neurotoxin serotype A, Diththeria toxin, cholera toxin, and bacterial enterotoxins; immunodominant antigens: HIV antigens including gag, RT, Integrase, env, nef, Tat and Rev, hepatitis B surface antigen, core antigen and antigens of other organisms; heat-shock proteins and chaperone proteins: of mammals and microorganisms including viruses, bacteria, fungi and parasites; carrier proteins including keyhole limpet cyanine, bovine serum albumin, ovalbumin, *E. coli* maltose-binding protein, Riboflavin carrier protein, glycoprotein D carrier protein, and many others, preferably PADRE and $Pol_{711}$ or any combination thereof.

In still another embodiment of the present invention, the PADRE is derived from a group comprising tetanus toxoid, *Clostridium botulinum* neurotoxin serotype A, Diththeria toxin, cholera toxin, bacterial enterotoxins and many others, preferably tetanus toxoid and said $Pol_{711}$ is derived from a group comprising HIV-1 polymerase, HIV antigens including gag, RT, Integrase, env, nef, Tat, Rev and other proteins, preferably HIV-1 polymerase.

In still another embodiment of the present invention, the engineered Tat DNA sequence is non-toxic to host as a consequence of structural disruption of important domains of Tat including CRD, BD and core domain of the virus.

The present invention relates to a method of obtaining a vaccine comprising non toxic, immunogenic viral Tat DNA sequence comprising of N-terminal region, Cysteine rich domain (CRD), Core domain, Basic domain (BD), C-terminal region and Exon II region, wherein the Tat Sequence is rendered non toxic and immunogenic by insertion of T-Helper Epitope into the Cysteine-rich domain, or Basic domain or Core domain of said Tat DNA sequence, optionally along with insertion of a synthetic Intron between C-terminal region and Exon II region of the Tat DNA Sequence, said method comprising step of dissolving said viral Tat DNA into phosphate buffer saline to obtain the vaccine.

The present invention relates to a kit having a vaccine comprising non toxic, immunogenic viral Tat DNA sequence in phosphate buffer saline, wherein said Tat DNA comprise N-terminal region, Cysteine rich domain (CRD), Core domain, Basic domain (BD), C-terminal region and Exon II region, wherein the Tat Sequence is rendered non toxic and immunogenic by insertion of T-Helper Epitope into the Cysteine-rich domain, or Basic domain or Core domain of said Tat DNA sequence, optionally along with insertion of a synthetic Intron between C-terminal region and Exon II region of the Tat DNA Sequence.

Some of these features are first-time strategies in the field. The most critical component of the present strategy is to disrupt cysteine-rich domain (CRD) and/or basic domains (BD) of Tat by inserting T-helper epitopes. Two independent advantages are expected to be accrued by this manipulation. First, the structural integrity of Tat is perturbed by T-helper epitope insertion disrupting many of Tat biological functions thus rendering safer for vaccination. This manipulation, however, is not likely to diminish natural immune responses to native Tat since care was taken not to disrupt known B-cell and CTL epitopes in Tat. Second, engineering of universal epitopes into CRD and/or BD is expected to recruit additional and stronger T-help augmenting the quality and quantity of antigen-specific immune responses. Thus, this strategy is expected to achieve two different and important objectives simultaneously.

The uniqueness of this strategy is the generation of a novel Tat vaccine that is superior to the existing forms of Tat vaccine candidates in two important respects; it has superior immunogenic properties and lacks toxicity as compared to native Tat vaccine or Tat toxoid.

Safety of Tat DNA Sequence:

Using standard molecular techniques, one of the two universal T-helper epitopes were inserted into cysteine-rich domain (CRD) and/or basic domain (BD) of Tat. While CRD regulates transactivation, chemokine induction and apoptosis properties of Tat, BD is responsible for nuclear localization, RNA binding and membrane translocation and many other functions. Thus disruption of these domains by grafting T-helpers is expected to attenuate the toxic functions of Tat thus making it safe for in vivo administration.

Immunogenicity of Tat DNA Sequence:

Importantly, engineering T-helper epitopes into CRD and BD is also expected to augment Tat-specific immune responses thus answering the question of non-immunogenicity of Tat. T-helper epitopes were engineered in such a way that the known B- and CTL epitopes in Tat are not disrupted.

Additional Immune-Modulatory Features:

Codon-optimization of Tat for efficient translation, engineering of a synthetic intron mimicking the natural expression of Tat and additional adjuvants at immunization.

Tat-Challenge Models:

Two novel and independent in vivo challenge models will be used to evaluate the significance of the augmented anti-Tat immune responses. Autologous tumor model (establishment or rejection of stable Tat-expressing tumor cell line in mouse) and a chimera virus-challenge model (EcoHIV-1 virus proliferation in mouse).

Augmented immune responses need not necessarily be protective immune response. Thus, the protective nature of Tat vaccine was tested in two different experimental models as described below:

A) EcoHIV challenge Model: David J Volksy's group created a model of HIV-1 infection of conventional mice for investigation of viral replication, control and pathogenesis. To enable viral proliferation in mice, although at a restricted level, the coding region of gp120 in HIV/NL4-3 virus strain was replaced with that of gp80 from ecotropic murine leukemia virus, a retrovirus that infects only rodents (Potash et al., 2005). The resulting chimeric virus, EcoHIV, productively infects murine, but not human lymphocytes. Adult, immunocompetent mice were readily susceptible to infection by a single inoculation of EcoHIV as shown by the detection of virus in splenic lymphocytes, peritoneal macrophages, and the brain. The virus produced in animals was infectious as shown by passage in culture, and immunogenic as shown by induction of antibodies to HIV-1 Gag and Tat. EcoHIV challenge model offers a cost effective and simple alternative for the primate models to evaluate vaccine efficiency especially in a resource-poor setting. This pre-established model was used to evaluate the efficacy of DNA vaccines of the instant invention. Mouse immunization and viral load evaluation have been standardized in JNCASR laboratory. To make in vivo monitoring of the virus proliferation technically simpler, GFP was engineered into EcoHIV to generate EcoHIV-GFP. The engineering of GFP would enable us to analyze the virus burden directly in different tissues using confocal microscopy rather than the use of RT-PCR on splenocytes. Reduction in the viral burden/load would give us a measure of vaccine efficacy.

B) Tumor Challenge Model: DNA vaccination has been shown to induce strong anti-tumor immune response. To characterize the quality of immune responses generated by Tat DNA vaccines, syngenic tumor challenge model (Holden et al., 1975; Mocellin, 2005; Stevenson et al., 2004a; Rice et al., 2002; Hedley et al., 1998) was used. Briefly, immunized mice would be challenged with syngenic tumor cells stably expressing Tat, eg. EL4 cells for C57BL/6 mice. Potential anti-Tat cell-mediated immune responses are expected to reject tumor development when compared to control mice. Stably transfected cell lines: Mammalian expression vectors that expressed $Tat_{co}$ under the control of the EF-1α promoter was transfected into the two syngenic cell lines, P815 ($H-2^d$ for BALB/c) and EL4 ($H-2^b$, for C57BL) and selected with G418 drug selection marker. Expression of Tat in the stably transfected cells was confirmed by western blotting analysis. Tumor establishment in mouse: Parental EL-4 cells ($10^6$) or Tat-expressing EL-4 cells (EL4-$Tat_{co}$) were injected intradermally into the hind flanks of C57BL/6 mice. The growth of the tumor was monitored. Both the parental cells and Tat-expressing cells efficiently induced tumors in mice hence these cells could be used to evaluate efficacy of the Tat DNA vaccines.

To ensure safety and functional integrity, the vaccine candidates must be evaluated in animal and cell models before taking them to human clinical trials.

This vaccination strategy involves DNA priming followed by DNA boosting. Alternative, rather complementary, strategies of immunization are possible including DNA priming followed by protein boosting, or protein priming followed by DNA boosting or protein priming followed by protein boosting. The quality and nature of the immune response generated by these alternative immunization schemes could have significant impact on protection. These alternative strategies have been used, using recombinant Tat-proteins with T-helper epitopes engineered as described in this document. The common theme behind all these immunization schemes is the use of modified Tat.

The limited success attained with HIV-1 env vaccines prompted search for alternative viral antigens that may serve as potential candidates of a multi-component HIV vaccine. The viral regulatory protein Tat offers several advantages as one of such potential candidate antigens. Several attempts made by other groups previously with the Tat vaccine have met with limited success for the following reasons. (1) Most of the published reports ignored the non-immunodominant nature of Tat (2) Most of these publications used Tat as a protein or toxoid in which form Tat couldn't have accessed the MHC class I pathway critical for virus control. (3) Many of these reports failed to employ molecular strategies to alleviate toxic properties of Tat. Unique molecular strategies to overcome the technical limitations of Tat vaccine have been proposed.

The most innovative aspect of present strategies is to engineer universal T-helper epitopes into the cysteine-rich domain (CRD) and/or basic domain (BD) of Tat. Two different objectives are expected to be achieved by this molecular manipulation. The T-helper epitopes are expected to recruit efficient T-help and augment immune responses to Tat thereby converting this poorly immunogenic antigen into strongly immunogenic one. Additionally and importantly, disruption of the well structured CRD and BD by inserting T-helper epitopes into them is expected to make Tat non-toxic or less toxic to the host since most of the critical biological functions of Tat are dependent on the structural integrity of these two domains.

Further, exploring additional molecular strategies to augment immune responses to Tat including the use of an optimized cellular promoter and stabilization of the viral transcript and enhanced translocation of the transcript by engineering a synthetic intron into Tat has been proposed. Unlike most of the previous strategies, present invention expresses Tat as a DNA expression vector, not as a recombinant protein. Tat, expressed from DNA vector is expected to be efficiently presented to the MHC class I pathway thus eliciting cellular immune responses required for efficient viral control. Some of these strategies could have direct relevance to other non-immunodominant antigens therefore, with far-reaching and broad-range impact of the DNA vaccine field, in general.

The instant invention is further elaborated with the help of following examples. However, these examples should not be construed to limit the scope of the invention.

EXAMPLE 1

Insertion Sequence for Codon Optimized Tat with PADRE Epitope Grafted into the Cysteine Rich Domain (CRD) of Tat

| Construct | N-term | Cysteine-Rich-Domain | Core Domain | Basic Domain | C-term | Exon II |
|---|---|---|---|---|---|---|
| PADRE- | ATGGAGCC | GCCTGC | TTCCA | CGGAA | GCTCCTCC | CCCCT |
| CRD | AGTAGATC | AACAAC | GACCA | GAAGC | AAGCAGCG | GCCTA |
| DNA | CTAACCTG | TGCTAC | AGGGC | GGCGC | AGGACCAC | GGACC |
| sequence | GAGCCCTG | TGCAAG | CTGGG | CAGCG | CAAAATCT | CAGGG |
|  | GAACCACC | CACTGC | CATCA | CCGGA | TATATCAA | CGACC |
|  | CTGGCAGC | GCCAAG | GCTAC | GC | AGCAG | CCACA |
|  | CAGCCCAA | TTTGTC | GGC |  |  | GGCAG |
|  | GACC | GCTGCC |  |  |  | CGAGG |
|  |  | TGGACG |  |  |  | AGAGC |
|  |  | CTGAAG |  |  |  | AAGA |
|  |  | GCTGCT |  |  |  | AGAA |
|  |  | GCCAGC |  |  |  | GGTGG |
|  |  | TACCAC |  |  |  | AGAGC |
|  |  | TGCCTG |  |  |  | AAGAC |
|  |  | GTGTGC |  |  |  | AGAG |
|  |  |  |  |  |  | ACAGA |
|  |  |  |  |  |  | CCCCT |
|  |  |  |  |  |  | TCGAC |

| Construct | N-term | Cysteine-Rich-Domain | Core Domain | Basic Domain | C-term | Exon II |
|---|---|---|---|---|---|---|
| PADRE-CRD Protein sequence | MEPVDPNL EPWNHPGS QPKT | ACNNCY CKHC AKFVAA WTLKAA ASYHCL VC | FQTKG LGISYG | RKKRR QRRS | APPSSEDHQ NLISKQ | TGA PLPRT QGDPT GSEES KKKVE SKTET DPFD |

DNA Sequence without Breakup: (PADRE Epitope Underlined): Represented by SEQUENCE ID NO.1

ATGGAGCCAGTAGATCCTAACCTGGAGCCCTGGAACCACCCTGGCAGCCA
GCCCAAGACCGCCTGCAACAACTGCTACTGCAAGCACTGCGCCAAGTTTG
TCGCTGCCTGGACGCTGAAGGCTGCTGCCAGCTACCACTGCCTGGTGTGC
TTCCAGACCAAGGGCCTGGGCATCAGCTACGGCCGGAAGAAGCGGCGCCA
GCGCCGGAGCGCTCCTCCAAGCAGCGAGGACCACCAAAATCTTATATCAA
AGCAGCCCCTGCCTAGGACCCAGGGCGACCCCACAGGCAGCGAGGAGAGC
AAGAAGAAGGTGGAGAGCAAGACAGAGACAGACCCCTTCGACTGA

Protein Sequence without Breakup: (PADRE Epitope Underlined): Represented by SEQUENCE ID NO.16

MEPVDPNLEPWNHPGSQPKTACNNCYCKHCAKFVAAWTLKAAASYHCLVC
FQTKGLGISYGRKKRRQRRSAPPSSEDHQNLISKQPLPRTQGDPTGSEES
KKKVESKTETDPFD

EXAMPLE 2

Insertion Sequence for Codon Optimized Tat with Pol$_{711}$ Epitope Grafted into the Cysteine Rich Domain (CRD) of Tat

| Construct | N-term | Cysteine-Rich-Domain | Core Domain | Basic

| Construct | N-term | Cysteine-Rich-Domain | Core Domain | Basic Domain | C-term | Exon II |
|---|---|---|---|---|---|---|
| | | | | | | TCGAC |
| | | | | | | TGA |
| Pol₇₁₁- | MEPVDPN | ACNNCYC | FQTKGLGI | RKKRRQ | APPSSEDH | PLPRT |
| CRD | LEPWNHP | KHC | SYG | RRS | QNLISKQ | QGDPT |
| Protein | GSQPKT | EKVYLAW | | | | GSEES |
| sequence | | VPAHKGI | | | | KKKVE |
| | | GSYHCLV | | | | SKTET |
| | | C | | | | DPFD |

DNA Sequence without Breakup: (Pol₇₁₁ Epitope Underlined): Represented by SEQUENCE ID NO.2

ATGGAGCCAGTAGATCCTAACCTGGAGCCCTGGAACCACCCTGGCAGCCA

GCCCAAGACCGCCTGCAACAACTGCTACTGCAAGCACTGCGAGAAGGTGT

ACCTCGCATGGGTGCCTGCCCACAAGGGCATTGGCAGCTACCACTGCCTG

GTGTGCTTCCAGACCAAGGGCCTGGGCATCAGCTACGGCCGGAAGAAGCG

GCGCCAGCGCCGGAGCGCTCCTCCAAGCAGCGAGGACCACCAAAATCTTA

TATCAAAGCAGCCCCTGCCTAGGACCCAGGGCGACCCCACAGGCAGCGAG

GAGAGCAAGAAGAAGGTGGAGAGCAAGACAGAGACAGACCCCTTCGACTA

G

Protein Sequence without Breakup: (Pol₇₁₁ Epitope Underlined): Represented by SEQUENCE ID NO.17

MEPVDPNLEPWNHPGSQPKTACNNCYCKHCEKVYLAWVPAHKGIGSYHCL

VCFQTKGLGISYGRKKRRQRRSAPPSSEDHQNLISKQPLPRTQGDPTGSE

ESKKKVESKTETDPFD

EXAMPLE 3

Insertion Sequence for Codon Optimized Tat with PADRE Epitope Grafted into the Basic Domain (BD) of Tat

| Construct | N-term | Cysteine-Rich-Domain | Core Domain | Basic Domain | C-term | Exon II |
|---|---|---|---|---|---|---|
| PADRE- | ATGGAGCC | GCCTGCAA | TTCCAG | CGGAAGA | GCTCCT | CCCCT |
| BD | AGTAGATC | CAACTGCT | ACCAAG | AG- | CCAAGC | GCCTA |
| DNA | CTAACCTG | ACTGCAAG | GGCCTG | GCCAAG | AGCGAG | GGACC |
| Sequence | GAGCCCTG | CACTGCAG | GGCATC | TTTGTCG | GACCAC | CAGGG |
| | GAACCACC | CTACCACT | AGCTAC | CTGCCTG | CAAAAT | CGACC |
| | CTGGCAGC | GCCTGGTG | GGC | GACGCT | CTTATA | CCACA |
| | CAGCCCAA | TGC | | GAAGGC | TCAAAG | GGCAG |
| | GACC | | | TGCTGCC- | CAG | CGAGG |
| | | | | CGGCGCC | | AGAGC |
| | | | | AGCGCCG | | AAGA |
| | | | | GAGC | | AGAA |
| | | | | | | GGTGG |
| | | | | | | AGAGC |
| | | | | | | AAGAC |
| | | | | | | AGAG |

-continued

| Construct | N-term | Cysteine-Rich-Domain | Core Domain | Basic Domain | C-term | Exon II |
|---|---|---|---|---|---|---|
| | | | | | | ACAGA |
| | | | | | | CCCCT |
| | | | | | | TCGAC |
| | | | | | | TGA |
| PADRE- | MEPVDPNL | ACNNCYCK | FQTKGL | RKKAKFV | APPSSED | PLPRT |
| BD | EPWNHPGS | HCSYHCLV | GISYG | AAWTLKA | HQNLIS | QGDPT |
| Protein | QPKT | C | | AARRQRR | KQ | GSEES |
| sequence | | | | S | | KKKVE |
| | | | | | | SKTET |
| | | | | | | DPFD |

DNA Sequence without Breakup: (PADRE Epitope Underlined): Represented by SEQUENCE ID NO.3

ATGGAGCCAGTAGATCCTAACCTGGAGCCCTGGAACCACCCTGGCAGCCA
GCCCAAGACCGCCTGCAACAACTGCTACTGCAAGCACTGCAGCTACCACT
GCCTGGTGTGCTTCCAGACCAAGGGCCTGGGCATCAGCTACGGCCGGAAG
AAGGCCAAGTTTGTCGCTGCCTGGACGCTGAAGGCTGCTGCCCGGCGCCA
GCGCCGGAGCGCTCCTCCAAGCAGCGAGGACCACCAAAATCTTATATCAA
AGCAGCCCCTGCCTAGGACCCAGGGCGACCCCACAGGCAGCGAGGAGAGC
AAGAAGAAGGTGGAGAGCAAGACAGAGACAGACCCCTTCGACTAG

Protein Sequence without Breakup: (PADRE Epitope Underlined): Represented by SEQUENCE ID NO.18

MEPVDPNLEPWNHPGSQPKTACNNCYCKHCSYHCLVCFQTKGLGISYGRK
KAKFVAAWTLKAAARRQRRSAPPSSEDHQNLISKQPLPRTQGDPTGSEES
KKKVESKTETDPFD

EXAMPLE 4

Insertion Sequence for Codon Optimized Tat with $Pol_{711}$ Epitope Grafted into the Basic Domain (BD) of Tat

| Construct | N-term | Cysteine-Rich-Domain | Core Domain | Basic Domain | C-term | Exon II |
|---|---|---|---|---|---|---|
| $Pol_{711}$- | ATGGAGC | GCCTGC | TTCCAG | CGGAAG | GCTCCTC | CCCCTG |
| BD | CAGTAGA | AACAAC | ACCAAG | AAGGA | CAAGCAG | CCTAGG |
| DNA | TCCTAAC | TGCTAC | GGCCTG | GAAGG | CGAGGAC | ACCCAG |
| sequence | CTGGAGC | TGCAAG | GGCATC | TGTACC | CACCAAA | GGCGAC |
| | CCTGGAA | CACTGC | AGCTAC | TCGCAT | ATCTTAT | CCCACA |
| | CCACCCT | AGCTAC | GGC | GGGTG | ATCAAAG | GGCAGC |
| | GGCAGCC | CACTGC | | CCTGCC | CAG | GAGGAG |
| | AGCCCAA | CTGGTG | | CACAA | | AGCAAG |
| | GACC | TGC | | GGGCA | | AAGAAG |
| | | | | TTGGCC | | GTGGAG |
| | | | | GGCGCC | | AGCAAG |
| | | | | AGCGCC | | ACAGAG |
| | | | | GGAGC | | ACAGAC |

| Construct | N-term | Cysteine-Rich-Domain | Core Domain | Basic Domain | C-term | Exon II |
|---|---|---|---|---|---|---|
| | | | | | | CCCTTC |
| | | | | | | GACTGA |
| Pol₇₁₁-BD Protein sequence | MEPVDPN LEPWNHP GSQPKT | ACNNCY CKHCSY HCLVC | FQTKGL GISYG | RKKEKV YLAWVP AHKGIG RRQRRS | APPSSEDH QNLISKQ | PLPRTQ GDPTGS EESKKK VESKTE TDPFD |

DNA Sequence without Breakup: (Pol₇₁₁ Epitope Underlined): Represented by SEQUENCE ID NO.4

ATGGAGCCAGTAGATCCTAACCTGGAGCCCTGGAACCACCCTGGCAGCCA
GCCCAAGACCGCCTGCAACAACTGCTACTGCAAGCACTGCAGCTACCACT
GCCTGGTGTGCTTCCAGACCAAGGGCCTGGGCATCAGCTACGGCCGGAAG
AAGGAGAAGGTGTACCTCGCATGGGTGCCTGCCCACAAGGGCATTGGCCG
GCGCCAGCGCCGGAGCGCTCCTCCAAGCAGCGAGGACCACCAAAATCTTA
TATCAAAGCAGCCCCTGCCTAGGACCCAGGGCGACCCCACAGGCAGCGAG
GAGAGCAAGAAGAAGGTGGAGAGCAAGACAGAGACAGACCCCTTCGACTG
A

Protein Sequence without Breakup: (Pol₇₁₁ Epitope Underlined): Represented by SEQUENCE ID NO.19

MEPVDPNLEPWNHPGSQPKTACNNCYCKHCSYHCLVCFQTKGLGISYGRK
KEKVYLAWVPAHKGIGRRQRRSAPPSSEDHQNLISKQPLPRTQGDPTGSE
ESKKKVESKTETDPFD

EXAMPLE 5

Insertion Sequence for Codon Optimized Tat with PADRE Epitope in Cysteine-Rich-Domain and Pol₇₁₁ Epitope Grafted into the Basic Domain of Tat

| Construct | N-term | Cysteine-Rich-Domain | Core Domain | Basic Domain | C-term | Exon II |
|---|---|---|---|---|---|---|
| Pol₇₁₁-BD DNA sequence | ATGGAGC CAGTAGA TCCTAAC CTGGAGC CCTGGAA CCACCCT GGCAGCC AGCCCAA GACC | GCCTGCA ACAACTG CTACTGC AAGCACT GC GCCAAG TTTGTCG CTGCCTG GACGCT GAAGGC TGCTGCC AGCTACC ACTGCCT GGTGTGC | TTCCAGA CCAAGGG CCTGGGC ATCAGCT ACGGC | CGGAAGA AGGAGA AGGTGT ACCTCGC ATGGGT GCCTGC CCACAA GGGCAT TGGCCGG CGCCAGC GCCGGAG C | GCTCCT CCAAGC AGCGAG GACCAC CAAAAT CTTATA TCAAAG CCCCTG CCTAGG ACCCAG GGCGAC CCCACA GGCAGC GAGGAG AGCAAG AAGAAG GTGGAG AGCAAG | CCCCTG CCTAGG ACCCAG GGCGAC ACCCAG GGCGAC CCCACA GGCAGC GAGGAG AGCAAG AAGAAG GTGGAG AGCAAG ACAGAG ACAGAC CCCTTC GACTGA |

-continued

| Construct | N-term | Cysteine-Rich-Domain | Core Domain | Basic Domain | C-term | Exon II |
|---|---|---|---|---|---|---|
| PADRE-<br>CRD,<br>$Pol_{711}$-<br>BD<br>Protein<br>sequence | MEPVDPN<br>LEPWNHP<br>GSQPKT | ACNNCYC<br>KHC<br>AKFVAA<br>WTLKAAA<br>SYHCLVC | FQTKGLGI<br>SYG | RKKEKVY<br>LAWVPAH<br>KGIGRRQ<br>RRS | APPSSED<br>HQNLIS<br>KQ | PLPRTQ<br>GDPTGS<br>EESKKK<br>VESKTE<br>TDPFD |

DNA Sequence without Breakup: (Respective Epitopes Underlined): Represented by SEQUENCE ID NO.5

ATGGAGCCAGTAGATCCTAACCTGGAGCCCTGGAACCACCCTGGCAGCCA

GCCCAAGACCGCCTGCAACAACTGCTACTGCAAGCACTGCGCCAAGTTTG

TCGCTGCCTGGACGCTGAAGGCTGCTGCCAGCTACCACTGCCTGGTGTGC

TTCCAGACCAAGGGCCTGGGCATCAGCTACGGCCGGAAGAAGGAGAAGGT

GTACCTCGCATGGGTGCCTGCCCACAAGGGCATTGGCCGGCGCCAGCG

CCGGAGCGCTCCTCCAAGCAGCGAGGACCACCAAAATCTTATATCAAAGC

AGCCCCTGCCTAGGACCCAGGGCGACCCCACAGGCAGCGAGGAGAGCAAG

AAGAAGGTGGAGAGCAAGACAGAGACAGACCCCTTCGACTGA

Protein Sequence without Breakup: (Respective Epitopes Underlined): Represented by SEQUENCE ID NO.20

MEPVDPNLEPWNHPGSQPKTACNNCYCKHCAKFVAAWTLKAAASYHCLVC

FQTKGLGISYGRKKEKVYLAWVPAHKGIGR

RQRRSAPPSSEDHQNLISKQPLPRTQGDPTGSEESKKKVESKTETDPFD

EXAMPLE 6

Insertion Sequence for Codon Optimized Tat with $Pol_{711}$ Epitope in Cysteine-Rich-Domain and PADRE Epitope Grafted into the Basic Domain of Tat

| Construct | N-term | Cysteine-Rich-Domain | Core Domain | Basic Domain | C-term | Exon II |
|---|---|---|---|---|---|---|
| $Pol_{711}$-<br>BD<br>DNA<br>sequence | ATGGA<br>GCCAG<br>TAGAT<br>CCTAA<br>CCTGG<br>AGCCC<br>TGGAA<br>CCACC<br>CTGGC<br>AGCCA<br>GCCCA<br>AGACC | GCCTGCA<br>ACAACTG<br>CTACTGC<br>AAGCACT<br>GC<br>GAGAAG<br>GTGTACC<br>TCGCATG<br>GGTGCC<br>TGCCCAC<br>AAGGGC<br>ATTGGCA<br>GCTACCA<br>CTGCCTG<br>GTGTGC | TTCCAG<br>ACCAAG<br>GGCCTG<br>GGCATC<br>AGCTAC<br>GGC | CGGAAG<br>AAGGC<br>CAAGTT<br>TGTCGC<br>TGCCTG<br>GACGC<br>TGAAG<br>GCTGCT<br>GCCCGG<br>CGCCAG<br>CGCCGG<br>AGC | GCTC<br>CTCC<br>AAGC<br>AGCG<br>AGGA<br>CCAC<br>CAAA<br>ATCT<br>TATA<br>TCAA<br>AGCA<br>G | CCCCTGC<br>CTAGGAC<br>CCAGGGC<br>GACCCCA<br>CAGGCAG<br>CGAGGAG<br>AGCAAGA<br>AGAAGGT<br>GGAGAGC<br>AAGACAG<br>AGACAGA<br>CCCCTTC<br>GACTGA |
| $Pol_{711}$-<br>CRD,<br>PADRE-<br>BD<br>Protein<br>sequence | MEPVD<br>PNLEP<br>WNHPG<br>SQPKT | ACNNCYC<br>KHC<br>EKVYLAW<br>VPAHKGI<br>GSYHCLV<br>C | FQTKGL<br>GISYG | RKKAKF<br>VAAWTL<br>KAAARR<br>QRRS | APPS<br>SEDH<br>QNLI<br>SKQ | PLPRTQG<br>DPTGSEES<br>KKKVESK<br>TETDPFD |

DNA Sequence without Breakup: (Respective Epitopes Underlined): Represented by SEQUENCE ID NO.6

ATGGAGCCAGTAGATCCTAACCTGGAGCCCTGGAACCACCCTGGCAGC

CAGCCCAAGACCGCCTGCAACAACTGCTACTGCAAGCACTGCGAGAAG

GTGTACCTCGCATGGGTGCCTGCCCACAAGGGCATTGGCAGCTACCAC

TGCCTGGTGTGCTTCCAGACCAGGGCCTGGGCATCAGCTACGGCCGGA

AGAAGGCCAAGTTTGTCGCTGCCTGGACGCTGAAGGCTGCTGCCCGGC

GCCAGCGCCGGAGCGCTCCTCCAAGCAGCGAGGACCACCAAAATCTTA

TATCAAAGCAGCCCCTGCCTAGGACCCAGGGCGACCCCACAGGCAGCG

AGGAGAGCAAGAAGAAGGTGGAGAGCAAGACAGAGACAGACCCCTTCG

ACTGA

Protein Sequence without Breakup: (Respective Epitopes Underlined): Represented by SEQUENCE ID NO.21

MEPVDPNLEPWNHPGSQPKTACNNCYCKHCEKVYLAWVPAHKGIGSYH

CLVCFQTKGLGISYGRKKAKFVAAWTLKAAARRQRRSAPPSSEDHQNL

ISKQPLPRTQGDPTGSEESKKKVESKTETDPFD

EXAMPLE 7

Insertion Sequence for Codon Optimized Tat with Synthetic Intron

| Tat | N-term | Cysteine-Rich-Domain | Core Domain | Basic Domain | C-term | Synthetic Intron | Exon II |
|---|---|---|---|---|---|---|---|
| Tat$_{int}$ DNA Sequence | ATGG AGCC AGTA GATCC TAACC TGGA GCCCT GGAA CCACC CTGGC AGCC AGCCC AAGA CC | GCCTG CAACA ACTGC TACTG CAAGC ACTGC AGCTA CCACT GCCTG GTGTG C | TTCC AGAC CAAG GGCC TGGG CATC AGCT ACGG C | CGGAA GAAGC GGCGC CAGCG CCGGA AGCT | GCTC CTCC AAGC AGCG AGG ACCA CCAA AATC TTAT ATCA AAGC AG | GTGAGTACT CCCTCTCAA AAGCGGGC ATGACTTCT GCGCTAAG ATTGTCAGT TTCCAAAAA CGAGGAGG ATTTGATAT TCACCTGGC CCGCGGTG ATGCCTTTG AGGGTGGC CGCGTCCAT CTGGTCAGA AAAGACAAT CTTTTTGTT GTCAAGCTT GAGGTGTG GCAGGCTT GAGATCTG GCCATACAC TTGAGTGAC AATGACATC CACTTTGCC TTTCTCTCC ACAG | CCCCTG CCTAG GACCC AGGGC GACCC CACAG GCAGC GAGGA GAGCA AGAAG AAGGT GGAGA GCAAG ACAGA GACAG ACCCCT TCGACT GA |
| Protein sequence | MEPV DPNLE PWNH PGSQP KT | ACNNC YCKHC SYHCL VC | FQTK GLGI SYG | RKKRR QRRS | APPS SEDH QNLI SKQ | | PLPRTQ GDPTGS EESKKK VESKTE TDPFD |

DNA Sequence without Breakup: (Synthetic Intron Underlined): Represented by SEQUENCE ID NO.7

ATGGAGCCAGTAGATCCTAACCTGGAGCCCTGGAACCACCCTGGCAGC

CAGCCCAAGACCGCCTGCAACAACTGCTACTGCAAGCACTGCAGCTAC

CACTGCCTGGTGTGCTTCCAGACCAAGGGCCTGGGCATCAGCTACGGC

CGGAAGAAGCGGCGCCAGCGCCGGAGCGCTCCTCCAAGCAGCGAGGAC

CACCAAAATCTTATATCAAAGCAGGTGAGTACTCCCTCTCAAAAGCGG

GCATGACTTCTGCGCTAAGATTGTCAGTTTCCAAAAACGAGGAGGATT

TGATATTCACCTGGCCCGCGGTGATGCCTTTGAGGGTGGCCGCGTCCA

TCTGGTCAGAAAAGACAATCTTTTTGTTGTCAAGCTTGAGGTGTGGCA

GGCTTGAGATCTGGCCATACACTTGAGTGACAATGACATCCACTTTGC

CTTTCTCTCCACAGCCCTGCCTAGGACCCAGGGCGACCCCACAGGCA

GCGAGGAGAGCAAGAAGAAGGTGGAGAGCAAGACAGAGACAGACCCCT

TCGACTGA

Protein Sequence without Breakup: Represented by SEQUENCE ID NO.21

MEPVDPNLEPWNHPGSQPKTACNNCYCKHCSYHCLVCFQTKGLGISYG

RKKRRQRRSAPPSSEDHQNLISKQPLPRTQGDPTGSEESKKKVESKTE

TDPFD

EXAMPLE 8

Insertion Sequence for Synthetic Intron: Represented by SEQUENCE ID NO.8

GTGAGTACTCCCTCTCAAAAGCGGGCATGACTTCTGCGCTAAGATTGT

CAGTTTCCAAAAACGAGGAGGATTTGATATTCACCTGGCCCGCGGTGA

TGCCTTTGAGGGTGGCCGCGTCCATCTGGTCAGAAAAGACAATCTTTT

TGTTGTCAAGCTTGAGGTGTGGCAGGCTTGAGATCTGGCCATACACTT

GAGTGACAATGACATCCACTTTGCCTTTCTCTCCACAG

EXAMPLE 9

DNA Sequence of the ApaI-SacI Deletion Construct (Intron Underlined; MluI and EcoRI Enzyme Sites are Marked in Bold)

Represented by SEQUENCE ID NO.9

ACGCGTTCCGGTGCCCGTCAGTGGGCAGAGCGCACATCGCCCACAGTC

CCCGAGAAGTTGGGGGGAGGGGTCGGCAATTGAACCGGTGCCTAGAGA

AGGTGGCGCGGGGTAAACTGGGAAAGTGATGTCGTGTACTGGCTCCGC

CTTTTTCCCGAGGGTGGGGGAGAACCGTATATAAGTGCAGTAGTCGCC

GTGAACGTTCTTTTTCGCAACGGGTTTGCCGCCAGAACACAG<u>GTAAGT</u>

<u>GCCGTGTGTGGTTCCCGCGGGCCTGGCCTCTTTACGGGTTATGGCCCT</u>

<u>TGCGTGCCTTGAATTACTTCCACGCCCCTGGCTGCAGTACGTGATTCT</u>

<u>TGATCCCGAGCTTCGGGTTGGAAGTGGGTGGGAGAGTTCGAGGCCTTG</u>

<u>CGCTTAAGGAGCCCCTTCGCCTCGTGCTTGAGTTGAGGCCTGGCCTGG</u>

<u>GCGCTGGGGCCGCCGCGTGCGAATCTGGTGGCACCTTCGCGCCTGTCT</u>

<u>CGCTGCTTTCGATAAGTCTCTAGCCATTTAAAATTTTTGATGACCTGC</u>

<u>TGCGACGCTTTTTTTCTGGCAAGATAGTCTTGTAAATGCGGGCCAAGA</u>

<u>TCTGCACACTGGTATTTCGGTTTTTGGGGCCGCGGGCGGCGACGGTGC</u>

<u>AAGCTCAAAATGGAGGACGCGGCGCTCGGGAGAGCGGGCGGGTGAGTC</u>

<u>ACCCACACAAAGGAAAAGGGCCTTTCCGTCCTCAGCCGTCGCTTCATG</u>

<u>TGACTCCACGGAGTACCGGGCGCCGTCCAGGCACCTCGATTAGTTCTC</u>

<u>GAGCTTTTGGAGTACGTCGTCTTTAGGTTGGGGGAGGGGTTTTATGC</u>

<u>GATGGAGTTTCCCCACACTGAGTGGGTGGAGACTGAAGTTAGGCCAGC</u>

<u>TTGGCACTTGATGTAATTCTCCTTGGAATTTGCCCTTTTTGAGTTTGG</u>

<u>ATCTTGGTTCATTCTCAAGCCTCAGACAGTGGTTCAAAGTTTTTTCT</u>

<u>TCCATTTCAG</u>GTGTCGTGAAGAATTC

EXAMPLE 10

DNA Sequence of the SacII Deletion Construct (Intron Underlined; MluI and EcoRI Enzyme Sites are Marked in Bold)

Represented by SEQUENCE ID NO.10

ACGCGTTCCGGTGCCCGTCAGTGGGCAGAGCGCACATCGCCCACAGTC

CCCGAGAAGTTGGGGGGAGGGGTCGGCAATTGAACCGGTGCCTAGAGA

AGGTGGCGCGGGGTAAACTGGGAAAGTGATGTCGTGTACTGGCTCCGC

CTTTTTCCCGAGGGTGGGGGAGAACCGTATATAAGTGCAGTAGTCGCC

GTGAACGTTCTTTTTCGCAACGGGTTTGCCGCCAGAACACAG<u>GTAAGT</u>

<u>GCCGTGTGTGGTTCCCGCGGGCGGCGACGGGCCCGTGCGTCCCAGCG</u>

<u>CACATGTTCGGCGAGGCGGGCCTGCGAGCGCGGCCACCGAGAATCGG</u>

<u>ACGGGGTAGTCTCAAGCTGGCCGGCCTGCTCTGGTGCCTGGCCTCGC</u>

<u>GCCGCCGTGTATCGCCCCGCCCTGGGCGGCAAGGCTGGCCCGGTCGGC</u>

<u>ACCAGTTGCGTGAGCGGAAAGATGGCCGCTTCCCGGCCCTGCTGCAGG</u>

<u>GAGCTCAAAATGGAGGACGCGGCGCTCGGGAGAGCGGGCGGGTGAGTC</u>

<u>ACCCACACAAAGGAAAAGGGCCTTTCCGTCCTCAGCCGTCGCTTCATG</u>

<u>TGACTCCACGGAGTACCGGGCGCCGTCCAGGCACCTCGATTAGTTCTC</u>

<u>GAGCTTTTGGAGTACGTCGTCTTTAGGTTGGGGGAGGGGTTTTATGC</u>

<u>GATGGAGTTTCCCCACACTGAGTGGGTGGAGACTGAAGTTAGGCCAGC</u>

<u>TTGGCACTTGATGTAATTCTCCTTGGAATTTGCCCTTTTTGAGTTTGG</u>

<u>ATCTTGGTTCATTCTCAAGCCTCAGACAGTGGTTCAAAGTTTTTTCT</u>

<u>TCCATTTCAG</u>GTGTCGTGAAGAATTC

EXAMPLE 11

DNA Sequence of the BglII-XhoI Deletion Construct (Intron Underlined; MluI and EcoRI Enzyme Sites are Marked in Bold)

Represented by SEQUENCE ID NO.11

ACGCGTTCCGGTGCCCGTCAGTGGGCAGAGCGCACATCGCCCACAGTC

CCCGAGAAGTTGGGGGGAGGGGTCGGCAATTGAACCGGTGCCTAGAGA

AGGTGGCGCGGGGTAAACTGGGAAAGTGATGTCGTGTACTGGCTCCGC

CTTTTTCCCGAGGGTGGGGGAGAACCGTATATAAGTGCAGTAGTCGCC

GTGAACGTTCTTTTTCGCAACGGGTTTGCCGCCAGAACACAG<u>GTAAGT</u>

<u>GCCGTGTGTGGTTCCCGCGGGCCTGGCCTCTTTACGGGTTATGGCCCT</u>

<u>TGCGTGCCTTGAATTACTTCCACGCCCCTGGCTGCAGTACGTGATTCT</u>

<u>TGATCCCGAGCTTCGGGTTGGAAGTGGGTGGGAGAGTTCGAGGCCTTG</u>

<u>CGCTTAAGGAGCCCCTTCGCCTCGTGCTTGAGTTGAGGCCTGGCCTGG</u>

<u>GCGCTGGGGCCGCCGCGTGCGAATCTGGTGGCACCTTCGCGCCTGTCT</u>

<u>CGCTGCTTTCGATAAGTCTCTAGCCATTTAAAATTTTTGATGACCTGC</u>

<u>TGCGACGCTTTTTTTCTGGCAAGATAGTCTTGTAAATGCGGGCCAAGA</u>

<u>TCTCGAGCTTTTGGAGTACGTCGTCTTTAGGTTGGGGGAGGGGTTTT</u>

<u>ATGCGATGGAGTTTCCCCACACTGAGTGGGTGGAGACTGAAGTTAGGC</u>

<u>CAGCTTGGCACTTGATGTAATTCTCCTTGGAATTTGCCCTTTTTGAGT</u>

<u>TTGGATCTTGGTTCATTCTCAAGCCTCAGACAGTGGTTCAAAGTTTTT</u>

<u>TTCTTCCATTTCAG</u>GTGTCGTGAAGAATTC

EXAMPLE 12

DNA Sequence of the PstI Deletion Construct (Intron Underlined; MluI and EcoRI Enzyme Sites are Marked in Bold)

Represented by SEQUENCE ID NO.12

ACGCGTTCCGGTGCCCGTCAGTGGGCAGAGCGCACATCGCCCACAGTC

CCCGAGAAGTTGGGGGGAGGGGTCGGCAATTGAACCGGTGCCTAGAGA

AGGTGGCGCGGGGTAAACTGGGAAAGTGATGTCGTGTACTGGCTCCGC

CTTTTTCCCGAGGGTGGGGGAGAACCGTATATAAGTGCAGTAGTCGCC

GTGAACGTTCTTTTTCGCAACGGGTTTGCCGCCAGAACACAG<u>GTAAGT</u>

<u>GCCGTGTGTGGTTCCCGCGGGCCTGGCCTCTTTACGGGTTATGGCCCT</u>

<u>TGCGTGCCTTGAATTACTTCCACGCCCCTGGCTGCAGGGAGCTCAAAA</u>

<u>TGGAGGACGCGGCGCTCGGGAGAGCGGGCGGGTGAGTCACCCACACAA</u>

<u>AGGAAAAGGGCCTTTCCGTCCTCAGCCGTCGCTTCATGTGACTCCACG</u>

<u>GAGTACCGGGCGCCGTCCAGGCACCTCGATTAGTTCTCGAGCTTTTGG</u>

<u>AGTACGTCGTCTTTAGGTTGGGGGAGGGGTTTTATGCGATGGAGTTT</u>

<u>CCCCACACTGAGTGGGTGGAGACTGAAGTTAGGCCAGCTTGGCACTTG</u>

<u>ATGTAATTCTCCTTGGAATTTGCCCTTTTTGAGTTTGGATCTTGGTTC</u>

<u>ATTCTCAAGCCTCAGACAGTGGTTCAAAGTTTTTTTCTTCCATTTCAG</u>

<u>GTGTCGTGAA</u>GAATTC

EXAMPLE 13

DNA Sequence of the PstI-SacII Deletion Construct (Intron Underlined; MluI and EcoRI Enzyme Sites are Marked in Bold)

Represented by SEQUENCE ID NO.13

ACGCGTTCCGGTGCCCGTCAGTGGGCAGAGCGCACATCGCCCACAGTC

CCCGAGAAGTTGGGGGAGGGGTCGGCAATTGAACCGGTGCCTAGAGA

AGGTGGCGCGGGGTAAACTGGGAAAGTGATGTCGTGTACTGGCTCCGC

CTTTTTCCCGAGGGTGGGGGAGAACCGTATATAAGTGCAGTAGTCGCC

GTGAACGTTCTTTTTCGCAACGGGTTTGCCGCCAGAACACAG<u>GTAAGT</u>

<u>GCCGTGTGTGGTTCCCGCTGCAGGGAGCTCAAAATGGAGGACGCGGCG</u>

<u>CTCGGGAGAGCGGGCGGGTGAGTCACCCACACAAAGGAAAAGGGCCTT</u>

<u>TCCGTCCTCAGCCGTCGCTTCATGTGACTCCACGGAGTACCGGGCGCC</u>

<u>GTCCAGGCACCTCGATTAGTTCTCGAGCTTTTGGAGTACGTCGTCTTT</u>

<u>AGGTTGGGGGAGGGGTTTTATGCGATGGAGTTTCCCCACACTGAGTG</u>

<u>GGTGGAGACTGAAGTTAGGCCAGCTTGGCACTTGATGTAATTCTCCTT</u>

<u>GGAATTTGCCCTTTTTGAGTTTGGATCTTGGTTCATTCTCAAGCCTCA</u>

<u>GACAGTGGTTCAAAGTTTTTTTCTTCCATTTCAGGTGTCGTGAA</u>GAAT
TC

EXAMPLE 14

DNA Sequence of the SacII-EcoRI Deletion Construct (Intron Underlined; MluI and EcoRI Enzyme Sites are Marked in Bold)

Represented by SEQUENCE ID NO.14

ACGCGTTCCGGTGCCCGTCAGTGGGCAGAGCGCACATCGCCCACAGTC

CCCGAGAAGTTGGGGGAGGGGTCGGCAATTGAACCGGTGCCTAGAGA

AGGTGGCGCGGGGTAAACTGGGAAAGTGATGTCGTGTACTGGCTCCGC

CTTTTTCCCGAGGGTGGGGGAGAACCGTATATAAGTGCAGTAGTCGCC

GTGAACGTTCTTTTTCGCAACGGGTTTGCCGCCAGAACACAG<u>GTAAGT</u>

<u>GCCGTGTGTGGTTC</u>

EXAMPLE 15

DNA Sequence of the Elongation Factor-1α Promoter (Full Length) (Intron Underlined; MluI and EcoRI Enzyme Sites are Marked in Bold)

Represented by SEQUENCE ID NO.15

ACGCGTTCCGGTGCCCGTCAGTGGGCAGAGCGCACATCGCCCACAGTC

CCCGAGAAGTTGGGGGAGGGGTCGGCAATTGAACCGGTGCCTAGAGA

AGGTGGCGCGGGGTAAACTGGGAAAGTGATGTCGTGTACTGGCTCCGC

CTTTTTCCCGAGGGTGGGGGAGAACCGTATATAAGTGCAGTAGTCGCC

GTGAACGTTCTTTTTCGCAACGGGTTTGCCGCCAGAACACAG<u>GTAAGT</u>

<u>GCCGTGTGTGGTTCCCGCGGGCCTGGCCTCTTTACGGGTTATGGCCCT</u>

<u>TGCGTGCCTTGAATTACTTCCACGCCCCTGGCTGCAGTACGTGATTCT</u>

<u>TGATCCCGAGCTTCGGGTTGGAAGTGGGTGGGAGAGTTCGAGGCCTTG</u>

<u>CGCTTAAGGAGCCCCTTCGCCTCGTGCTTGAGTTGAGGCCTGGCCTGG</u>

<u>GCGCTGGGGCCGCCGCGTGCGAATCTGGTGGCACCTTCGCGCCTGTCT</u>

<u>CGCTGCTTTCGATAAGTCTCTAGCCATTTAAAATTTTTGATGACCTGC</u>

<u>TGCGACGCTTTTTTTCTGGCAAGATAGTCTTGTAAATGCGGGCCAAGA</u>

<u>TCTGCACACTGGTATTTCGGTTTTTGGGGCCGCGGGCGGCGACGGGGC</u>

<u>CCGTGCGTCCCAGCGCACATGTTCGGCGAGGCGGGGCCTGCGAGCGCG</u>

<u>GCCACCGAGAATCGGACGGGGGTAGTCTCAAGCTGGCCGGCCTGCTCT</u>

<u>GGTGCCTGGCCTCGCGCCGCCGTGTATCGCCCCGCCCTGGGCGGCAAG</u>

<u>GCTGGCCCGGTCGGCACCAGTTGCGTGAGCGGAAAGATGGCCGCTTCC</u>

<u>CGGCCCTGCTGCAGGGAGCTCAAAATGGAGGACGCGGCGCTCGGGAGA</u>

<u>GCGGGCGGGTGAGTCACCCACACAAAGGAAAAGGGCCTTTCCGTCCTC</u>

<u>AGCCGTCGCTTCATGTGACTCCACGGAGTACCGGGCGCCGTCCAGGCA</u>

<u>CCTCGATTAGTTCTCGAGCTTTTGGAGTACGTCGTCTTTAGGTTGGGG</u>

<u>GGAGGGGTTTTATGCGATGGAGTTTCCCCACACTGAGTGGGTGGAGAC</u>

<u>TGAAGTTAGGCCAGCTTGGCACTTGATGTAATTCTCCTTGGAATTTGC</u>

<u>CCTTTTTGAGTTTGGATCTTGGTTCATTCTCAAGCCTCAGACAGTGGT</u>

<u>TCAAAGTTTTTTTCTTCCATTTCAGGTGTCGTGAA</u>GAATTC

EXAMPLE 16

Generation of Expression Vectors

HIV-1 Subtype C Tat Wild Type and Codon-Optimized Expression Vectors:

The cloning of full-length wild type subtype C Tat vector was reported previously from JNCASR laboratory (Siddappa et al., 2007). Construction of the codon-optimized HIV-1 Tat gene, corresponding to the first exon of the consensus HIV-1 subtype C sequence, pDV2-Tat$_{co}$, has also been described previously (Ramakrishna et al., 2004). This vector, however, lacked exon II. Using the overlap PCR approach, the full-length Tat expression vector was assembled, by adding 30 aa of subtype C consensus sequence of the exon II to pDV2-Tat$_{co}$, in which all the codons have been optimized for the mammalian expression. Exon I was amplified using the forward primer N113 (5'-TA GAATTCGCCGCCGCCATGGAGCCAGTAGATCCTA-ACCTA-3') (represented by SEQUENCE ID NO.23) and reverse primer N458 (5'GTCGCCCTGGGTCCTAGGCA-GGGGCTGCTTTGATATAAGATTTT-3') (represented by SEQUENCE ID NO.24). The reverse primer was designed to contain a 20 bp overlap with exon I and a 24 bp overlap with exon II. The plasmid pDV2-Tat$_{co}$ (containing only exon I of Tat) served as template for the amplification. Amplification conditions were as follows: 94° C. for 1 min, 54° C. for 30 sec, and 72° C. for 1 min for 3 cycles and 94° C. for 1 min, 60° C. for 30 sec, and 72° C. for 1 min for 12 cycles. The amplicon was gel purified using a commercial kit (Qiagen, Hilden, Germany). Codon optimized consensus sequence of the second exon was synthesized as a single primer of 87 bases (N456) (5'-CCCCTGCCTAGGACCCA-GGGCGACCCCACAGGCAGCGAGGAGAGCAA GAAGAAGGTGGAGAGCAAGACAGAGACAGAC-CCCTTCGAC-3') (represented by SEQUENCE ID NO.25). Exon II amplicon of ~100 bp was obtained using the primers N456 and N457 (5'-AGAG TCTAGACTAGTCGAAGGGGTCTGTCTCTGTCTT-3') (represented by SEQUENCE ID NO.26) in a non-templated PCR using the amplification conditions 94° C. for 1 min, 54° C. for 30 sec, and 72° C. for 1 min for 3 cycles and 94° C. for 1 min, 60° C. for 30 sec, and 72° C. for 1 min for 12 cycles. The exon I and exon II amplicons were gel purified and an overlap PCR was carried out, using the primers N113 and N457, which contained the enzymes sites EcoRI and XbaI, respectively. The final product of 350 bp was gel purified and directionally cloned between the EcoRI and XbaI sites, downstream of the CMV promoter on the vector pcDNA3.1 (+), generating the pCMV-Tat$_{co}$ that contains full-length Tat with optimized codons (FIG. 1).

EXAMPLE 17

Generation of Expression Vectors

Intron Engineering into Tat$_{co}$:

The overlap PCR approach was employed to amplify a synthetic intron of 230 bp derived from vector pIRESpuro (#6031-1, Clontech), and cloned it between the two exons of codon-optimized Tat on vector pcDNA3.1 (+) (FIG. 5). The intron was first added to exon I of Tat followed by the addition of exon II thus generating full-length Tat with engineered intron between the exons. Amplification of the synthetic intron was performed using the primer pair N521 (5'-GACCACCAAAATCTTATATCAAAGCAGGTGAG-TACTCCCTCTC-3') (represented by SEQUENCE ID NO.27) and N522 (5'-TCGCCCGGGTCCTAGGCA-GGGGCTGTGGAGAGAAAGGC-3') (represented by SEQUENCE ID NO.28) while 100 ng of the plasmid pIRESpuro (#6031-1, Clontech) served as the template for the reaction. The amplification conditions were as follows: 94° C. for 1 min, 42° C. for 30 sec, and 72° C. for 1 min for 3 cycles and 94° C. for 1 min, 60° C. for 30 sec, and 72° C. for 1 min for 12 cycles. The amplicon of ~300 bp was gel purified and used as a mega-primer for the next round of PCR, where the plasmid pCMV-Tat$_{co}$ served as the template. The initial 3 cycles of amplification was carried out in the absence of the primers. The amplification conditions were as follows: 94° C. for 1 min, 42° C. for 30 sec, and 72° C. for 1 min for 3 cycles and 94° C. for 1 min, 60° C. for 30 sec, and 72° C. for 1 min for 12 cycles. The cycler was paused for a few seconds after the third cycle and the primer mix consisting of N113 (5'-TAGAATTCG-CCGCCGCCATGGAGCCAGTAGATCCTAACCTA-3') (SEQUENCE ID NO.23) and N522 (5'-TCGCCCGGGTC-CTAGGCAGGGGCTGTGGAGAGAAAGGC-3') (SE-QUENCE ID NO.28), the forward and reverse primers respectively, was added to the vial. Amplification of a 480 bp fragment from this PCR was obtained. The product comprising the first exon and the synthetic intron was gel eluted and mixed with the second exon amplicon of Tat, obtained as described above. The cycler was paused after the third cycle and the primer mix comprising of N113 (5'-TA GAATTCGCCGCCGCCATGGAGCCAGTAGATCCTA-ACCTA-3') (SEQUENCE ID NO.23) and N457 (5'-AGAG TCTAGACTAGTCGAAGGGGTCTGTCTCTGTCTT-3') (SEQUENCE ID NO.26) containing the restriction enzyme sites EcoRI and XbaI, respectively, was added to the vial and the amplification was continued for an additional 15 cycles. The amplicon of 560 bp comprising of exon I-synthetic intron-exon II, was gel eluted and directionally cloned into two different vectors under the control of the CMV or the EF-1α promoters, on the pcDNA3.1 (+) backbone to obtain pCMV-Tat$_{int}$ and pEF-1α Tat$_{int}$ constructs.

EXAMPLE 18

Generation of Expression Vectors

Grafting T-Helper Epitopes HTL into Tat$_{co}$:

The overlap PCR approach was used to graft the HTL epitopes into Tatco constructs. Towards this, two different epitopes the 'PADRE' epitope (Pan DR helper T-cell epitope, AKFVAAWTLKAAA (represented by SEQUENCE ID NO.29)) originally identified in the tetanus toxin that has been subjected to additional modification to bind most common HLA-DR molecules with high affinity (Alexander et al., 2000; Alexander et al., 1994b) and the pol 711 epitope (EKVYLAWVPAHKGIG) (represented by SEQUENCE ID NO.30) derived from HIV-1 RT polymerase, which has been reported to bind a large number of different HLA-DR (Wilson C et al., 2001) as well as several murine class II molecules were used. The HTL epitopes were engineered into the cysteine-rich domain (CRD, between residues C30 and S31) and/or the basic domain (BD, between residues K52 and R53), singly or in combination in both of the orientations.

TABLE 1

| Target Tat Domain | HTL Epitope Engineered | Primer | Sequence (5'-3') |
|---|---|---|---|
| — | — | N113 | TA<u>GAATTC</u>CCCCCCCCCATGGAGCCAGTAGATCCTAACCTA |
| — | — | N457 | AGAG<u>TGTAGA</u>CTACTAGTCGAAGGGGTCTCTCTCTGTCTT |
| CRD | PADRE | N648 | CTGAAGGCTGCTGCC*AGCTACCACTGCCTGGTG |
|  |  | N649 | GGCAGCAGCCTTCAGCGTCCAGGCAGCGACAAACTTGGC*GCAG TGCTTGCAGTAGC |
|  | Pol 711 | N650 | CACAAGGGCATTGGC*ACCTACCACTGCCTGGTG |
|  |  | N651 | GCCAATGCCCTTGTGGGCAGGCACCCATGCGAGGTACACCTTC TC*GCAGTGCTTGCAGTAGC |
| BD | PADRE | N679 | CTGAAGGCTGCTGCC*CGGCGCCAGCGCGGGAGC |
|  |  | N680 | GGCAGCAGCCTTCAGGCTCCAGGCAGCGACAAACTTGGC*C TTCTTCCGGCCGTAGC |
|  | Pol 711 | N652 | CCACAAGGGCATTGGC*CGGCGCCAGCGCCGGAGC |
|  |  | N653 | GCCAATGCCCTTGTGGGCAGGCACCCATGCGAGGTACACCTTC TC*CTTCTTCCGGCCGTAGC |

Primers used to graft HTL epitopes into Tat: top and bottom primers in a pair represent forward and reverse primers respectively. The reverse primers are presented as reverse complement. The asterisk represents the junction between two adjacent domains. Restriction enzymes have been highlighted by underlining.

The amplification conditions were as follows: 94° C. for 1 min, 42° C. for 30 sec, and 72° C. for 1 min for 3 cycles and 94° C. for 1 min, 60° C. for 30 sec, and 72° C. for 1 min for 12 cycles for 12 cycles, for the first round of PCR, which yielded Product 'A' and Product 13', and the amplification conditions for the second round of PCR that yielded product 'C' were 94° C. for 1 min, 60° C. for 30 sec, and 72° C. for 1 min for 15 cycles. Product 'C' was directionally cloned between EcoRI and XbaI sites downstream of the CMV or the EF-1α promoter on the pcDNA3.1 (+) backbone.

EXAMPLE 19

Generation of Expression Vectors

Cloning of Full-Length EF-1α Promoter:

The vector, pEF-BOS was procured, containing the 1.2 kb upstream element of the EF-1α gene, as a gift from Dr. Shigekazu Nagata (Mizushima and Nagata, 1990). Placing the EF1-α promoter upstream of the Tat vector was achieved in two successive steps (FIG. 12, p100). In the first step, a larger fragment of the promoter (800 bp fragment) was directionally transferred upstream of Tat between AflII and EcoRI RE sites of the pcDNA3.1 (+) vector. In the second step, the reminder 400 bp 5' part of the EF-1α promoter was amplified using the forward primer, N570 (5'-ATAG ACGCGTGTGAGGCTCAGGTCGCCGTCAGTGGGC-3') (represented by SEQUENCE ID NO.31) and reverse primer, N573 (5'-GGGCTTAAGCGCAAGGCGTCG-3') (represented by SEQUENCE ID NO.32), which contained the RE sites MluI and AflII, respectively. The amplification conditions were as follows: 94° C. for 1 min, 48° C. for 30 sec, and 72° C. for 1 min for 3 cycles and 94° C. for 1 min, 65° C. for 30 sec, and 72° C. for 1 min for 12 cycles. 100 ng of pEF-BOS plasmid was used as template for the amplification. The ~400 bp fragment was directionally cloned between the MluI and AflII sites, thus assembling the full-length EF-1α promoter on the pcDNA3.1 (+) backbone, in the place of the original CMV promoter (FIG. 2).

EXAMPLE 20

Generation of Expression Vectors

Construction of EF-1α Promoter:

EF-1α $Tat_{co}$ plasmid was obtained by replacing the CMV promoter in the plasmid CMV-$Tat_{co}$ (p215.1). Restriction enzyme sites MluI and EcoRI were used for promoter transfer.

The cloning of full-length wild type subtype C Tat vector was reported previously from JNCASR laboratory (Siddappa et al., 2007). Construction of the codon-optimized HIV-1 Tat gene, corresponding to the first exon of the consensus HIV-1 subtype C sequence, pDV2-$Tat_{co}$, has also been described previously (Ramakrishna et al., 2004). This vector, however, lacked exon II. Using the overlap PCR approach, the full-length Tat expression vector was assembled, by adding 30 aa of subtype C consensus sequence of the exon II to pDV2-$Tat_{co}$, in which all the codons have been optimized for the mammalian expression. Exon I was amplified using the forward primer N113 (5'-TA GAATTCGCCGCCGCCATGGAGCCAGTAGATCCTA-ACCTA-3') (SEQUENCE ID NO.23) and reverse primer N458 (5'GTCGCCCTGGGTCCTAGGCAGGGGCT-GCTTTGATATAAGATTTT-3') (SEQUENCE ID NO.24). The reverse primer was designed to contain a 20 bp overlap with exon I and a 24 bp overlap with exon II. The plasmid pDV2-$Tat_{co}$ (containing only exon I of Tat) served as template for the amplification. Amplification conditions were as follows: 94° C. for 1 min, 54° C. for 30 sec, and 72° C. for 1 min for 3 cycles and 94° C. for 1 min, 60° C. for 30 sec, and 72° C. for 1 min for 12 cycles. The amplicon was gel purified using a commercial kit (Qiagen, Hilden, Germany). Codon optimized consensus sequence of the second exon was synthesized as a single primer of 87 bases (N456) (5'-CCCCTGCCTAGGACCCAGGGCGACCCCACAG-GCAGCGAGGAGAGCAA GAAGAAGGTGGAGAG-CAAGACAGAGACAGACCCCTTCGAC-3') (SEQUENCE ID NO.25). Exon II amplicon of ~100 bp was obtained using the primers N456 and N457 (5'-AGAG TCTAGACTAGTCGAAGGGGTCTGTCTCTGTCTT-3') (SEQUENCE ID NO.26) in a non-templated PCR using the amplification conditions 94° C. for 1 min, 54° C. for 30 sec, and 72° C. for 1 min for 3 cycles and 94° C. for 1 min, 60° C. for 30 sec, and 72° C. for 1 min for 12 cycles. The exon I and exon II amplicons were gel purified and an overlap PCR was carried out, using the primers N113 and N457, which contained the enzymes sites EcoRI and XbaI, respectively. The final product of 350 bp was gel purified and directionally cloned between the EcoRI and XbaI sites, downstream of the EF-1α promoter on the vector pcDNA3.1 (+), generating the pEF-1α-Tat$_{co}$, that contains full-length Tat with optimized codons (FIG. 3).

EXAMPLE 21

Generation of Expression Vectors

Construction of the Deletion Mutants of the EF-1α Promoter:

Deletion analysis of the EF-1α intron I was undertaken to reduce the overall length of the promoter on the one hand and to evaluate the suppressive role of the putative 'negative regulatory element' (NRE) or any other cis-acting regulatory element on the other hand. To generate deletion mutants within the first intron, the whole EF-1α promoter was transferred to pUC19 vector from pcDNA3.1 (+) using NruI and EcoRI sites. Diverse restriction enzymes, either singly or in combination, were used to generate a series of deletion mutations in the first intron as schematically shown in (FIG. 14, p102). Each of the EF-1α promoter deletion mutants was subsequently returned to pcDNA3.1 (+) using MluI and EcoRI sites thus replacing the original CMV promoter in CMV-Tat$_{co}$ and placing Tat$_{co}$ under the control of the mutant EF-1α promoter. The constructs were labeled after the RE used for the deletion. The constructs have been labeled as: ApaI-SacI, SacII, BglII-XhoI, PstI, PstI-SacII, and SacII-EcoRI (Int-less). The final construct lacks the intron completely.

EXAMPLE 22

Engineering T-Helper Epitopes into Tat Makes it Safe for Immunization

Most of the toxic properties of Tat can be attributed to the cysteine-rich domain (CRD) or the basic domain (BD) of Tat. T-helper (HTL) epitopes were inserted into one or both of these domains to perturb protein structure and the function of Tat to make it safe for immunization. Two different HTL epitopes were used for this purpose. First, a non-natural Pan HLA-DR binding epitope, PADRE (Alexander et al., 2000; Alexander et al., 1994a), derived from tetanus toxoid. Second, The other epitope, Pol$_{711}$, was derived from HIV-1 polymerase (van der Burg et al., 1999). Both of these epitopes have very high binding affinity to mouse MHC class II molecules and they also bind several common Human MHC. HTL epitopes were engineered into the CRD and/or the BD singly or in combination in both of the orientations.

Transactivation Assay:

To augment immunogenicity of Tat and to reduce toxicity, two strong universal T-helper (HTL) epitopes were introduced into this protein. One of the epitope is a non-natural Pan HLA-DR binding epitope, PADRE (Alexander et al., 2000; Alexander et al., 1994a), derived from tetanus toxoid. The other epitope, Pol$_{711}$, was derived from HIV-1 polymerase (van der Burg et al., 1999). Both of these epitopes have very high binding affinity to mouse MHC class II molecules and they also bind several common Human MHC. HTL epitopes were engineered into the cysteine-rich domain (CRD) and/or the basic domain (BD) singly or in combination in both of the orientations (FIG. 4, left panel). As mentioned above, two different objectives have been expected to be achieved by the HTL engineering into Tat. One, recruitment of efficient T-help to make Tat immunogenic and two, to abrogate toxic properties of Tat thus improving safety. Disrupting the CRD and/or BD is to abrogate several biological functions of Tat as these two domains play significant role in governing Tat functions. While engineering HTL, precaution was taken not to disrupt known B- or CTL epitopes of Tat. Using epitopes with cross-reactive binding between human and murine class II molecules would enable their evaluation in a standard mouse model (Alexander et al., 2002; Lopez-Diaz et al., 2003). Preliminary results from mouse immunizations demonstrated greatly augmented immune responses from the Tat construct where the PADRE HTL was engineered into the CD of Tat (Data not presented). Tat transactivation activity was significantly abrogated when either the CRD or BD domain was disrupted. In this experiment, a dual reporter vector, (expresses two different genes, Secreted Alkaline Phosphatase—SEAP, and Green Fluorescent Protein—GFP, under the control of the viral promoter) GFP-SEAP reporter vector was introduced into HEK293 cells along with one of the Tat-expression vectors. Three different Tat-expression vectors with intact CRD and BD (FIG. 4, right-top panel, wild type, codon optimized and intron engineered Tat proteins) are transactivation active and upregulated gene expression from the HIV-1 LTR permitting expression of GFP or SEAP. In contrast, all the 6 Tat-expression vectors with CRD and/or BD disrupted failed to transactivate reporter gene expression from the viral promoter (FIG. 4, right, bottom panel). This result suggested that Tat proteins with either of the domains disrupted is safe for vaccination.

EXAMPLE 23

Engineering T-Helper Epitopes into Tat Makes it Safe for Immunization—Apoptosis Assay When cells are exposed to Tat, the viral protein triggers cell death by inducing apoptosis. The CRD and also BD play a significant role in cell apoptosis. If one of these domains is disrupted, the engineered Tat should not be capable of killing cells. This hypothesis was tested using the BD or CRD disrupted Tat vectors. To examine if domain disruption of Tat abrogated the apoptotic function of Tat, THP-1 cells were transiently transfected with Tat vectors with intact domains (wild type or codon-optimized Tat) or with a Tat vector in which both of the CRD and BD were disrupted by HTL grafting. Twenty-four hours after the transfection, cells were stained for Annexin V-FITC in a buffer containing propidium iodide and analyzed by flow cytometry using FACSCalibur (BD Biosciences). While the wild type (wt) and codon-optimized (co) Tat DNA induced significantly higher levels of apoptosis, 48% and 51% cells positive respectively, domain-disrupted Tat (double HTL) induced low level apoptosis indistinguishable from the mock (empty vector) control. The difference between intact Tat constructs and the domain-disrupted Tat was explicit when mean fluorescence intensity (MFI) values were compared (right panels with graphical representation) suggesting that domain disruption led to profound attenuation of this viral transactivator thus making it safe for immunization, genetic, protein, or in any other format (FIG. 5).

EXAMPLE 24

Engineering T-Helper Epitopes into Tat Makes it Immunologically Superior

Groups of mice (5 per group) were immunized with different Tat-expressing DNA vectors intra-muscularly, 100 μg DNA per immunization, as per standard protocols. One primer immunization was followed by three booster immunizations and splenocytes were harvested 3 months after the final booster immunization. ELISPOT assay for cytokines interferon gamma (IFNγ, a Th-1 representative cytokine, desirable immune response) or interleukine-4 (IL-4, a Th-2 type cytokine, less desirable) was performed. The data presented in the FIG. 6 show that Tat with PADRE engineered into CRD, but not into BD, shows significantly augmented IFNγ response as compared to the Wt-Tat antigen. Tat expression driven either by the CMV or EF-1α promoter essentially show identical pattern of immune response. Insertion of the HIV-1 RT HTL doesn't enhance immune response. The immune response generated by the PADRE epitope is the more desirable Th-1 type (IFNγ) and no discernable IL-4 response was observed. In summary, the engineering of the PADRE epitope into the CRD of Tat alone elicits the most desirable Th-1 type immune response. This vector construct will be used in subsequent experiments for further development of the Tat antigens (FIG. 6).

The data presented above, serve as proof-of-the-concept experiments providing experimental evidence that The PADRE engineered Tat antigens are highly immunogenic and non-toxic.

EXAMPLE 25

Intron Engineered Tat Induces Higher Order Gene Expression

Using the primer extension strategy, a synthetic intron of small size (230 bp) from pIRES-puro (Clontech, #6031-1) was introduced between the two exons of Tat to enhance the stability of cytoplasmic RNA and gene expression. The intron-containing Tat gene was placed downstream of both of the CMV and EF-1α promoters on the pcDNA3.1 (+) backbone. $Tat_{int}$ construct was compared with Tat (wild type) and $Tat_{co}$ (codon-optimized) for the transactivation property using reporter assays. Briefly, $Tat_{wt}$, $Tat_{co}$ and $Tat_{int}$ constructs driven by CMV or EF-1α promoter, were cotransfected with the dual reporter plasmid, HIV-LTR-SEAP-IRES-GFP, in HEK 293 cells. Following transfection, gene expression was monitored every 24 h. At all the time points of analysis and from both the promoters, $Tat_{int}$ produced significantly higher levels of the reporter genes as compared to $Tat_{wt}$ or $Tat_{co}$ suggesting that the presence of intron indeed improved gene expression as expected (FIG. 7).

EXAMPLE 26

Intron Engineered Tat Induces Higher Order Immune Response

Importantly, Tat into which the intron inserted (domains not disrupted) too induced elevated immune responses with an efficiency comparable to HTL-engineered Tat (FIG. 8). In additional experiments, Tat was compared with and without intron in immunization. Tat with intron induced generation of significantly greater number of cytokine lymphocytes (Panel A) and higher magnitude of lymphocyte proliferation (Panel B) suggesting successful immunization. The superior performance of the Tatint was manifested under both of the promoters (see FIG. 8) and in two different strains of mice, BALB/c and C57BL/6 as well.

EXAMPLE 27

Intron Engineered Tat Controls Viral Load in Mice

The immunized mice were challenged with EcoHIV virus using one-prime-three-boost regimen. EcoHIV is a chimera HIV-1 in which original envelope was replaced by that of the gp80, the envelope of ecotropic murine leukemia virus (MLV), a retrovirus that infects only rodents (Potash et al., Proc Natl Acad Sci USA 102:3760-3765, 2005). EcoHIV can replicate in the conventional mice, although in a restricted manner, therefore offering a powerful tool of investigation of viral replication, control and pathogenesis. Two weeks after the last booster, immunized mice were challenged with EcoHIV virus and viral load was determined using real-time PCR. Compared to the parental vector control (pv), Tat immunized mice contained significantly less viral load (FIG. 9). Tat with intron controlled viral load to a greater extent than regular Tat. The data provide evidence that intron engineering is capable of generating higher levels of immune response and controlling the virus in the mouse model.

EXAMPLE 28

Tat DNA Vectors with an Intron and HTL Engineered Together are Safe

The new Tat vectors contains an intron between the first and second exons of Tat. The PADRE HTL epitope has been inserted at the extreme ends of CRD unlike in the previous vectors where the HTL was inserted in the middle of CRD. Recent work in JNCASR laboratory mapped an immunodominant B-cell epitope within the CRD in Indian clinical cohorts. That means, the HTL insertion (between amino acid residues 30 and 31) in the older vectors destroyed this epitope. To avoid this problem, to leave the natural B-cell epitope intact, two new Tat vectors were developed by inserting the HTL (red box) at the N-term end of the CRD (C22 Tat) or C-term of the CRD (C37 Tat). An additional Tat vector in which the HTL was inserted into the core domain (CD) was also generated. Only the intact wild type (wt) Tat could activate the viral promoter and induce expression of GFP in HEK293 cells but not any other tat with the domain engineering. The RFP expression confirms transfection efficiency was good. The western blot analysis (the bottom panel) confirms the expression of all the proteins in the cells. Taken together, these data prove that Tat in the newly engineered vectors is safe for immunization purpose (FIG. 10).

EXAMPLE 29

Virus Related Assays

Preparation of the EcoHIV Viral Stocks:
HEK 293T cells were transfected with the 10 μg of EcoHIV plasmid, a gift from Dr. David J Volsky (Potash et al., 2005), using the $CaCl_2$ method (Jordan et al., 1996). The supernatant was harvested 48 h post-transfection. The supernatant was spun at 1,500 rpm for 10 min at room temperature, and then filtered through a 0.45 µm membrane filter and stored frozen at −80° C. until use. The concentration of p24 in the supernatant was quantified using a commercial ELISA kit (Cat # NEK050, Perkin Elmer, Inc). The virus was pelleted using high-speed centrifugation (SS34 rotor, 50,000×g for 3 h), washed once and resuspended in saline. One hundred ng of p24 was used when the virus was injected through the tail vein for establishing the infection in mice (Potash et al., 2005). For viral challenge experiment, following immunization, 5 µg, of virus was administered through the intraperitoneal route (Saini et al., 2007).

EXAMPLE 30

Immunological Assays

DNA Immunization:

The immunization quality plasmid DNA was prepared using (#12381, Qiagen EndoFree Plasmid Mega kit) as per the manufacturer's instructions. The DNA was resuspended in endofree PBS (Manukirti, endotoxin<0.06 EU) and the endotoxin amounts were analyzed using a standard LAL assay (QCL-1000, Biowhittaker) and found to be within recommended limits (<0.1 EU/µg DNA). 100 µg of the DNA was injected into the tibialis anterior muscle of mice that were 8-12 week old. Each immunization consisted of four or five mice per group. The immunization schedule involved one primary immunization followed by a single booster or three boosters. Animals were housed and maintained in a facility adhering to the recommendations of the Committee for the Purpose of Control and Supervision of Experiments on Animals (CPCSEA) of India and the Institutional Animal Ethics Committee (IAEC) of JNCASR.

EXAMPLE 31

Immunological Assays

Lymphoproliferation Assay:

The DNA primed mice were sacrificed by cervical dislocation and the spleens were collected aseptically into a 60 mm sterile dish containing 2 ml of complete medium. To release splenocytes into the medium, the organ was crushed by using the hub of a 2 ml disposable syringe and by applying gentle pressure. The cells were collected into 15 ml screw-cap tubes (Corning) containing 5 ml of RPMI medium supplemented with 10% FBS. The cell debris was allowed to settle by gravity for 2 min and the upper layer containing the cells was carefully transferred to fresh tubes. Viable cells were counted using trypan blue exclusion technique. 50-100×$10^6$ cells per spleen were typically recovered. Splenocytes were cultured in triplicate wells in a flat-bottom 96-well microplate at 2×$10^5$ cells per well. Cells were activated in the presence of a mitogen, antigen or peptide pool for four days. In some experiments, the in vitro peptide activation was precluded and the cells were directly characterized for the immune function. A pool of six overlapping 20 mer peptides, with a 10 residue overlap between peptides, spanning the exon I of Tat, was used at 2 µg/ml concentration for cell activation as reported previously (Ramakrishna et al., 2004). Conconavalin A was used as positive control, for cell proliferation at a final concentration of 5 µg/ml. After incubation, the extent of cell proliferation was measured by adding [$^3$H] Thymidine, (10 µCi/ml) to the wells and cultures were incubated for additional 4 h at 37° C. for incorporation of the label. Plates were harvested using a cell harvester (Skatron, Norway). The filters were dried and radioactive counts were determined using a β-scintillation counter (Wallac, 1409).

EXAMPLE 32

Immunological Assays

ELISPOT Assay:

ELISPOT Assay was performed for the Th1 cytokine IFNγ (mouse IFNγ ELISPOT, BD pharmingen) and the Th2 cytokine IL-4 (mouse IL-4 ELISPOT, BD pharmingen) before invitro stimulation. Briefly, the IFNγ-specific capture antibody (5 µg/ml) was adsorbed onto the PVDF-backed 96-well plates by incubating the antibody solution overnight at 4° C. The plates were blocked with complete medium for 2 h at room temperature, and primed splenocytes (0.2×$10^6$ cells) were added to each well. Antigen, peptide pool or a suitable mitogen was added at appropriate concentration to labeled wells and the cells in a final volume of 200 µl medium were incubated for 24 h. The cells were decanted by inverting the plate. To each well 200 µl of sterile distilled water was added and the plates were incubated in 4° C. for 5 min to osmotically lyse the cells. Cell debris was removed by washing the wells three times with 1×PBS (200 µl per wash) and the wells were incubated with a biotinylated anti-IFNγ antibody (0.5 µg/ml) for 2 h. The plates were washed three times with 1×PBS containing 0.05% Tween-20, and the wells were incubated with HRP-conjugated avidin (0.25 µg/ml) for 1 h. Spots were developed using the substrate 3-amino-9-ethylcarbazole substrate solution (#551951, BD Biosciences) and incubating the plates for 20 min at room temperature. A combination of phorbol myristate acetate (1 µg/ml) and ionomycin (0.5 µg/ml) was used as a positive control for cell stimulation. The spots were enumerated using the KS ELISPOT system (Carl Zeiss, Germany).

EXAMPLE 33

Cellular Promoter Optimization

The human cytomegalovirus major immediate early (CMV) promoter/enhancer is one of the strongest promoters known. This promoter is most frequently used in gene therapeutic applications, as it is highly functional in cell lines and tissues of diverse origin. Expression from the CMV promoter, like from other viral regulatory elements, nevertheless, is downregulated in several physiological contexts either through the interferon-mediated pathways or mechanisms yet to be defined. Given its viral origin and inconsistency in gene expression made it necessary to search for an alternative promoter with improved expression properties.

The promoter element of the Elongation factor-1α (EF-1α) gene has been shown to perform as efficiently as the CMV promoter, or even superior in a few cases. Similar to the CMV promoter, gene expression form the EF-1α promoter is ubiquitous. Importantly, unlike the CMV promoter, EF-1α promoter was not subjected to gene silencing through the IFN-mediated or CpG methylation pathways. Paradoxically, except for a single publication, the potential of EF-1α has not been evaluated for genetic immunization, although this promoter has been used in gene therapeutic approaches.

With this objective in mind, DNA expression vectors were constructed containing the EF-1α promoter and compared its performance with that of the CMV promoter. The objectives of this analysis are two-fold, to delineate important regulatory elements of the EF-1α promoter on the one hand and to evaluate its performance in immunologically important cell lines such as the T-cells, monocytes and myoblasts on the other hand. A previous publication identified a negative regulatory element (NRE) in the intron of the EF-1α promoter in HeLa cells. Performing a similar analysis in immunologically relevant cells is important which will be attempted through the present study.

Generation of EF-1α Promoter Variant Promoters:

Restriction enzyme digestion was used to delete different fragments within the intron-I to reduce the length of the cellular promoter on the one hand and examine the function of the NRE on the other hand (see FIGS. 11 and 11a). All the cellular promoter variants were cloned upstream of HIV-1 Tat and compared with the CMV promoter expressing the viral antigen.

EF-1α Variant Promoters Express Reporter Genes Efficiently:

HEK293 cells were transfected with a reporter vector (expressing both SEAP and GFP under the control of the HIV promoter) and one of the EF-1α promoters or the CMV promoter vectors driving Tat. All the vectors expressed Tat (FIG. 12) which in turn induced expression of GFP (Panel-A) or SEAP. They also rescue virus from HLM-1 cells efficiently. EF-1α promoter which completely lacked the intron was non-functional. RFP expression was used as a control for the transfection efficiency (FIG. 12).

EXAMPLE 34

Tat Driven by EF-1α Variant Promoters Induces High Quality Immune Responses

C57BL/6 Mice were immunized with Tat DNA vectors under the control of CMV promoter of a series of EF-1α promoters as shown on the left side. Mice (four or five animals per group) were immunized with 100 µg of plasmid DNA according to the schedule shown in the line diagram. ELISPOT response was performed on splenocytes directly without in vitro cell stimulation. Each assay consisted of $0.2 \times 10^6$ splenocytes incubated with a pool of Tat peptide representing the full length of the viral antigen. The results indicate that some of the cellular promoter constructs perform with an efficiency comparable to the CMV promoter. The immunization induced primarily the more desirable TH-1 type (IFNγ) (FIG. 13).

EXAMPLE 35

Tat Immunization by EF-1α Variant Promoters Efficiently Controls Viral Load

Mice were immunized with one of the four Tat-expression vectors shown in FIG. 14 following the regimen depicted. Two different mouse strains were employed. Two weeks after the last booster, immunized mice were challenged with EcoHIV virus and viral load was determined using real-time PCR. All the immunized mice controlled viral load to significantly low levels as compared to the control immunized with the parental vector. The ApaI-SacII variant promoter of the EF-1α promoter controlled the virus to the greatest level as efficiently as the CMV promoter in both of the mouse strains. These data indicate that the ApaI-SacII and SacII variant promoters have a great potential for genetic immunization. These promoters are more efficient than the original EF-1α promoter and may not be associated with the disadvantages of the CMV viral promoter (FIG. 14).

EXAMPLE 36

Vaccine Efficiency—Qualitative Analysis of Infection of Mice by EcoHIV

EcoHIV challenge model was used to test the efficacy of Tat vaccine constructs of the present invention. The EcoHIV plasmid was obtained as a kind gift from Dr. David J. Volsky. The infection was standardized by EcoHIV in two different strains of mice, BALB/c and C57BL/6, essentially following the protocol outlined in their paper (Potash et al., 2005). Briefly, 293T cells transfected with the EcoHIV plasmid, served as the producer cell line, to obtain the viral stock. Cell-free viral stock was prepared using high-speed centrifugation. BALB/c or C57BL/6 mice were inoculated by an i.v. injection (tail vein) of 0.1 µg p24 EcoHIV. Six weeks after infection, or mock-infection, mice were euthanized and splenocytes were collected for analysis. The splenocytes are depleted of the $CD8^+$ T-cell subset using the complement mediated lysis procedure as described above. The $CD8^+$-depleted splenocytes were fixed, permeabilized, stained for intra-cellular p24 and analyzed by confocal microscopy as described. Immunofluorescence staining for intracellular p24 revealed the presence of several brightly stained cells in infected mice, ascertaining efficient and progressive viral replication (FIG. 15).

Viral Load Determination in Real-Time PCR:

For the EcoHIV viral challenge experiments, mice were infected with 5 µg p24 of EcoHIV/NL4-3 by intraperitoneal injection of cell-free virus, as previously described (Saini et al., 2007). One week after the challenge, mice were euthanized by cervical dislocation and spleen and peritoneal macrophages were collected. DNA was isolated from spleen using a commercial column (#G10N0, Sigma) and the proviral load was determined using real-time PCR.

Standardization of the Real-Time PCRs for EcoHIV and GAPDH:

The real-time PCR was standardized for EcoHIV and glyceraldehydes phosphate dehydrogenase (GAPDH) using plasmid standards (FIG. 16). GAPDH amplification was used as the internal control and to normalize the proviral load. The primers N909 (5'-GGCCAAACCCCGTTCTG-3') (represented by SEQUENCE ID NO.33) and N910 (5'-ACTTAACAGGTTTGGGCTTGGA-3') (represented by SEQUENCE ID NO.34) used for the viral load PCR were located on gp80 of EcoHIV and amplify a 56 bp fragment between 7116-7172 (Potash et al., 2005). The amplification conditions were: 94° C. for 1 min, 56° C. for 30 sec, and 72° C. for 30 sec for 40 cycles. Primers N1040 (5'-GAGCTGAACGGGAAGCTCACT-3') (represented by SEQUENCE ID NO.35) and N1041 (5'-CACGTCAGATCCACGACGGACACATTG-3') (represented by SEQUENCE ID NO.36) were employed for GAPDH amplification using the following reaction conditions: 94° C. for 1 min, 66° C. for 30 sec, and 72° C. for 30 sec for 40 cycles. The amplicon obtained was 120 bp in length. The optimal annealing temperatures for these two pairs of primers were identified using a gradient PCR (MyCyler Thermal cycler, Biorad). The real-time PCR was performed using a commercial kit (#62345, Bio-Rad) and using Rotor-Gene 6000 (Corbett life Sciences, Australia) and the data were analyzed using Rotor-Gene 1.7.28 software (FIG. 16).

REFERENCES

Agadjanyan M G, Ghochikyan A, Petrushina I, Vasilevko V, Movsesyan N, Mkrtichyan M, Saing T, Cribbs D H: Prototype Alzheimer's Disease Vaccine Using the Immunodominant B Cell Epitope from {beta}-Amyloid and Promiscuous T Cell Epitope Pan HLA DR-Binding Peptide. J Immunol 174:1580-1586 (2005).

Albini A, Benelli R, Giunciuglio D, Cai T, Mariani G, Ferrini S, Noonan D M: Identification of a novel domain of HIV tat involved in monocyte chemotaxis. J Biol Chem 273:15895-15900 (1998).

Alexander J, del Guercio M F, Frame B, Maewal A, Sette A, Nahm M H, Newman M J: Development of experimental carbohydrate-conjugate vaccines composed of *Streptococcus pneumoniae* capsular polysaccharides and the universal helper T-lymphocyte epitope (PADRE). Vaccine 22:2362-2367 (2004).

Alexander J, del Guercio M F, Maewal A, Qiao L, Fikes J, Chesnut R W, Paulson J, Bundle D R, DeFrees S, Sette A: Linear PADRE T helper epitope and carbohydrate B cell epitope conjugates induce specific high titer IgG antibody responses. J Immunol % 2000 Feb. 1; 164 (3):1625-33 (2000).

Alexander J, Fikes J, Hoffman S, Franke E, Sacci J, Appella E, Chisari F V, Guidotti L G, Chesnut R W, Livingston B, Sette A: The optimization of helper T lymphocyte (HTL) function in vaccine development. Immunol Res 18:79-92 (1998).

Alexander J, Oseroff C, Dahlberg C, Qin M, Ishioka G, Beebe M, Fikes J, Newman M, Chesnut R W, Morton P A, Fok K, Appella E, Sette A: A decaepitope polypeptide primes for multiple CD8+ IFN-gamma and Th lymphocyte responses: evaluation of multiepitope polypeptides as a mode for vaccine delivery. J Immunol % 2002 Jun. 15; 168 (12):6189-98 (2002).

Alexander J, Sidney J, Southwood S, Ruppert J, Oseroff C, Maewal A, Snoke K, Serra H M, Kubo R T, Sette A: Development of high potency universal DR-restricted helper epitopes by modification of high affinity DR-blocking peptides. Immunity % 1994 December; 1(9): 751-61 (1994a).

Alexander J, Sidney J, Southwood S, Ruppert J, Oseroff C, Maewal A, Snoke K, Serra H M, Kubo R T, Sette A: Development of high potency universal DR-restricted helper epitopes by modification of high affinity DR-blocking peptides. Immunity 1:751-761 (1994b).

Allen T M, O'Connor D H, Jing P, Dzuris J L, Mothe B R, Vogel T U, Dunphy E, Liebl M E, Emerson C, Wilson N, Kunstman K J, Wang X, Allison D B, Hughes A L, Desrosiers R C, Altman J D, Wolinsky S M, Sette A, Watkins D I: Tat-specific cytotoxic T lymphocytes select for SIV escape variants during resolution of primary viraemia. Nature 407:386-390 (2000).

Bangari D S, Mittal S K: Current strategies and future directions for eluding adenoviral vector immunity. Curr Gene Ther 6:215-226 (2006).

Beebe M, Qin M, Moi M, Wu S, Heiati H, Walker L, Newman M, Fikes J, Ishioka G Y: Formulation and Characterization of a Ten-peptide Single-vial Vaccine, EP-2101, Designed to Induce Cytotoxic T-lymphocyte Responses for Cancer Immunotherapy. Hum Vaccin 4: (2007).

Belliard G, Hurtrel B, Moreau E, B A P L, Monceaux V, Rogues B, Desgranges C, Aubertin A M, Grand R L, Muller S: Tat-neutralizing versus Tat-protecting antibodies in rhesus macaques vaccinated with Tat peptides. Vaccine 23:1399-1407 (2005).

Belot F, Guerreiro C, Baleux F, Mulard L A: Synthesis of two linear PADRE conjugates bearing a deca- or pentadecasaccharide B epitope as potential synthetic vaccines against *Shigella flexneri* serotype 2a infection. Chemistry 11:1625-1635 (2005).

Belyakov I M, Derby M A, Ahlers J D, Kelsall B L, Earl P, Moss B, Strober W, Berzofsky J A: Mucosal immunization with HIV-1 peptide vaccine induces mucosal and systemic cytotoxic T lymphocytes and protective immunity in mice against intrarectal recombinant HIV-vaccinia challenge. Proc Natl Acad Sci USA 95:1709-1714 (1998).

Blazevic V, Ranki A, Mattinen S, Valle S L, Koskimies S, Jung G, Krohn K J: Helper T-cell recognition of HIV-1 Tat synthetic peptides. J Acquir Immune Defic Syndr 6:881-890 (1993).

Borrow P, Lewicki H, Hahn B H, Shaw G M, Oldstone M B: Virus-specific CD8+ cytotoxic T-lymphocyte activity associated with control of viremia in primary human immunodeficiency virus type 1 infection. J Virol 68:6103-6110 (1994).

Bubnoff vB: 'Stopping a steam train': Immunizations and enrollment in a second trial with MRKAd5 have now been permanently stopped, and volunteers in the Phambili and STEP trials are being unblinded. IAVI Report 11:1-6 (2007).

Cafaro A, Caputo A, Fracasso C, Maggiorella M T, Goletti D, Baroncelli S, Pace M, Sernicola L, Koanga-Mogtomo M L, Betti M, Borsetti A, Belli R, Akerblom L, Corrias F, Butto S, Heeney J, Verani P, Titti F, Ensoli B: Control of SHIV-89.6P-infection of cynomolgus monkeys by HIV-1 Tat protein vaccine. Nat Med 5:643-650 (1999).

Calarota S A, Leandersson A C, Bratt G, Hinkula J, Klinman D M, Weinhold K J, Sandstrom E, Wahren B: Immune responses in asymptomatic HIV-1-infected patients after HIV-DNA immunization followed by highly active anti-retroviral treatment. J Immunol 163:2330-2338 (1999).

Caselli E, Betti M, Grossi M P, Balboni P G, Rossi C, Boarini C, Cafaro A, Barbanti-Brodano G, Ensoli B, Caputo A: DNA immunization with HIV-1 tat mutated in the trans activation domain induces humoral and cellular immune responses against wild-type Tat. J Immunol 162: 5631-5638 (1999).

Chambers R S, Johnston S A: High-level generation of polyclonal antibodies by genetic immunization. Nat Biotechnol 21:1088-1092 (2003).

Chang H C, Samaniego F, Nair B C, Buonaguro L, Ensoli B: HIV-1 Tat protein exits from cells via a leaderless secretory pathway and binds to extracellular matrix-associated heparan sulfate proteoglycans through its basic region. AIDS 11:1421-1431 (1997).

Cohen J: AIDS RESEARCH: Feud Over AIDS Vaccine Trials Leads Prominent Italian Researchers to Court. Science 317:738-739 (2007).

Cohen S S, Li C, Ding L, Cao Y, Pardee A B, Shevach E M, Cohen D I: Pronounced acute immunosuppression in vivo mediated by HIV Tat challenge. Proc Natl Acad Sci USA 96:10842-10847 (1999).

de M A, Lambeck A J, Regts J, van Dam G M, Nijman H W, Snippe H, Wilschut J, Daemen T: Viral vector-based prime-boost immunization regimens: a possible involvement of T-cell competition. Gene Ther 15:393-403 (2008).

Dean D A, Strong D D, Zimmer W E: Nuclear entry of nonviral vectors. Gene Ther 12:881-890 (2005).

Decroix N, Quan C P, Pamonsinlapatham P, Bouvet J P: Mucosal immunity induced by intramuscular administration of free peptides in-line with PADRE: IgA antibodies to the ELDKWA epitope of HIV gp41. Scand J Immunol 56:59-65 (2002).

Dyson H J, Wright P E: Intrinsically unstructured proteins and their functions. Nat Rev Mol Cell Biol 6:197-208 (2005).

Ensoli B, Cafaro A: Control of viral replication and disease onset in cynomolgus monkeys by HIV-1 TAT vaccine. J Biol Regul Homeost Agents 14:22-26 (2000).

Ensoli B, Fiorelli V, Ensoli F, Cafaro A, Titti F, Butto S, Monini P, Magnani M, Caputo A, Garaci E: Candidate HIV-1 Tat vaccine development: from basic science to clinical trials. AIDS 20:2245-2261 (2006).

Evans T G, Keefer M C, Weinhold K J, Wolff M, Montefiori D, Gorse G J, Graham B S, McElrath M J, Clements-Mann M L, Mulligan M J, Fast P, Walker M C, Excler J L, Duliege A M, Tartaglia J: A Canarypox Vaccine Expressing Multiple Human Immunodeficiency Virus Type 1 Genes Given Alone or with Rgp120 Elicits Broad and Durable CD8+ Cytotoxic T Lymphocyte Responses in Seronegative Volunteers. J Infect Dis 180:290-298 (1999).

Fanales-Belasio E, Moretti S, Nappi F, Barillari G, Micheletti F, Cafaro A, Ensoli B: Native HIV-1 Tat protein targets monocyte-derived dendritic cells and enhances their maturation, function, and antigen-specific T cell responses. J Immunol 168:197-206 (2002).

Fitzmaurice C J, Brown L E, McInerney T L, Jackson D C: The assembly and immunological properties of non-linear synthetic immunogens containing T-cell and B-cell determinants. Vaccine 14:553-560 (1996).

Gallo R C: Tat as one key to HIV-induced immune pathogenesis and Tat toxoid as an important component of a vaccine. Proc Natl Acad Sci USA 96:8324-8326 (1999).

Gao W J, Peng X M, Xie D Y, Xie Q F, Gao Z L, Yao J L: Construction of exogenous multiple epitopes of helper T lymphocytes and DNA immunization of its chimeric plasmid with HBV pre-S2/S gene. World J Gastroenterol 10:2979-2983 (2004).

Gavioli R, Cellini S, Castaldello A, Voltan R, Gallerani E, Gagliardoni F, Fortini C, Cofano E B, Triulzi C, Cafaro A, Srivastava I, Barnett S, Caputo A, Ensoli B: The Tat protein broadens T cell responses directed to the HIV-1 antigens Gag and Env: implications for the design of new vaccination strategies against AIDS. Vaccine 26:727-737 (2008).

Gavioli R, Gallerani E, Fortini C, Fabris M, Bottoni A, Canella A, Bonaccorsi A, Marastoni M, Micheletti F, Cafaro A, Rimessi P, Caputo A, Ensoli B: HIV-1 Tat Protein Modulates the Generation of Cytotoxic T Cell Epitopes by Modifying Proteasome Composition and Enzymatic Activity. J Immunol 173:3838-3843 (2004).

Giacca M: The HIV-1 Tat Protein: A Multifaceted Target for Novel Therapeutic Opportunities. Curr Drug Targets Immune Endocr Metabol Disord 4:277-285 (2004).

Goldstein G: HIV-1 Tat protein as a potential AIDS vaccine. Nat Med 2:960-964 (1996).

Gorse G J, Baden L R, Wecker M, Newman M J, Ferrari G, Weinhold K J, Livingston B D, Villafana T L, Li H, Noonan E, Russell N D: Safety and immunogenicity of cytotoxic T-lymphocyte poly-epitope, DNA plasmid (EP HIV-1090) vaccine in healthy, human immunodeficiency virus type 1 (HIV-1)-uninfected adults. Vaccine 26:215-223 (2008).

Goulder P J, Addo M M, Altfeld M A, Rosenberg E S, Tang Y, Govender U, Mngqundaniso N, Annamalai K, Vogel T U, Hammond M, Bunce M, Coovadia H M, Walker B D: Rapid Definition of Five Novel HLA-A*3002-Restricted Human Immunodeficiency Virus-Specific Cytotoxic T-Lymphocyte Epitopes by Elispot and Intracellular Cytokine Staining Assays. J Virol 75:1339-1347 (2001).

Greenstein J L, Schad V C, Goodwin W H, Brauer A B, Bollinger B K, Chin R D, Kuo M C: A universal T cell epitope-containing peptide from hepatitis B surface antigen can enhance antibody specific for HIV gp120. J Immunol 148:3970-3977 (1992).

Gregoire C, Peloponese J M, Jr., Esquieu D, Opi S, Campbell G, Solomiac M, Lebrun E, Lebreton J, Loret E P: Homonuclear (1)H-NMR assignment and structural characterization of human immunodeficiency virus type 1 Tat Mal protein. Biopolymers 62:324-335 (2001).

Gringeri A, Santagostino E, Muca-Perja M, Le Buanec H, Bizzini B, Lachgar A, Zagury J F, Rappaport J, Burny A, Gallo R C, Zagury D: Tat toxoid as a component of a preventive vaccine in seronegative subjects. J Acquir Immune Defic Syndr Hum Retrovirol 20:371-375 (1999).

Gringeri A, Santagostino E, Muca-Perja M, Mannucci P M, Zagury J F, Bizzini B, Lachgar A, Carcagno M, Rappaport J, Criscuolo M, Blattner W, Burny A, Gallo R C, Zagury D: Safety and immunogenicity of HIV-1 Tat toxoid in immunocompromised HIV-1-infected patients. J Hum Virol 1:293-298 (1998).

Gupta S, Boppana R, Mishra G C, Saha B, Mitra D: HIV-1 Tat suppresses gp120-specific T cell response in IL-10-dependent manner. J Immunol 180:79-88 (2008).

Hadas E, Borjabad A, Chao W, Saini M, Ichiyama K, Potash M J, Volsky D J: Testing antiretroviral drug efficacy in conventional mice infected with chimeric HIV-1. AIDS 21:905-909 (2007).

Hedley M L, Strominger J L, Urban R G: Plasmid DNA encoding targeted naturally processed peptides generates protective cytotoxic T lymphocyte responses in immunized animals. Hum Gene Ther % 1998 Feb. 10; 9 (3):325-32 (1998).

Hejdeman B, Bostrom A C, Matsuda R, Calarota S, Lenkei R, Fredriksson E L, Sandstrom E, Bratt G, Wahren B: DNA Immunization with HIV Early Genes in HIV Type 1-Infected Patients on Highly Active Antiretroviral Therapy. AIDS Res Hum Retroviruses 20:860-870 (2004).

Ho D D, Huang Y: The HIV-1 vaccine race. Cell 110:135-138 (2002).

Holden H T, Kirchner H, Herberman R B: Secondary cell-mediated cytotoxic response to syngeneic mouse tumor challenge. J Immunol % 1975 August; 115 (2):327-31 (1975).

Hsu S C, Chargelegue D, Obeid O E, Steward M W: Synergistic effect of immunization with a peptide cocktail inducing antibody, helper and cytotoxic T-cell responses on protection against respiratory syncytial virus. J Gen Virol 80 (Pt 6):1401-1405 (1999).

Huang L, Bosch I, Hofmann W, Sodroski J, Pardee A B: Tat protein induces human immunodeficiency virus type 1 (HIV-1) coreceptors and promotes infection with both macrophage-tropic and T-lymphotropic HIV-1 strains. J Virol 72:8952-8960 (1998).

Huang L, Li C J, Pardee A B: Human immunodeficiency virus type 1 TAT protein activates B lymphocytes. Biochem Biophys Res Commun 237:461-464 (1997).

Huigen M C, Kamp W, Nottet H S: Multiple effects of HIV-1 trans-activator protein on the pathogenesis of HIV-1 infection. Eur J Clin Invest 34:57-66 (2004).

Hung C F, Tsai Y C, He L, Wu T C: DNA vaccines encoding Ii-PADRE generates potent PADRE-specific CD4+ T-cell immune responses and enhances vaccine potency. Mol Ther 15:1211-1219 (2007).

Jeang K T, Xiao H, Rich E A: Multifaceted activities of the HIV-1 transactivator of transcription, Tat. J Biol Chem 274:28837-28840 (1999).

Kaiser J: AIDS RESEARCH: Review of Vaccine Failure Prompts a Return to Basics. Science 320:30-31 (2008).

Kiepiela P, Ngumbela K, Thobakgale C, Ramduth D, Honeyborne I, Moodley E, Reddy S, de Pierres C, Mncube Z, Mkhwanazi N, Bishop K, van der Stok M, Nair K, Khan N, Crawford H, Payne R, Leslie A, Prado J, Prendergast A, Frater J, McCarthy N, Brander C, Learn G H, Nickle D, Rousseau C, Coovadia H, Mullins J I, Heckerman D, Walker B D, Goulder P: CD8+ T-cell responses to different HIV proteins have discordant associations with viral load. Nat Med 13:46-53 (2007).

Kim D, Hoory T, Wu T C, Hung C F: Enhancing DNA vaccine potency by combining a strategy to prolong dendritic cell life and intracellular targeting strategies with a strategy to boost CD4+ T cell. Hum Gene Ther 18:1129-1139 (2007).

Kim D T, Mitchell D J, Brockstedt D G, Fong L, Nolan G P, Fathman C G, Engleman E G, Rothbard J B: Introduction of soluble proteins into the MHC class I pathway by conjugation to an HIV tat peptide. J Immunol 159:1666-1668 (1997).

Krone W J, Debouck C, Epstein L G, Heutink P, Meloen R, Goudsmit J: Natural antibodies to HIV-tat epitopes and expression of HIV-1 genes in vivo. J Med Virol 26:261-270 (1988).

Lafrenie R M, Wahl L M, Epstein J S, Yamada K M, Dhawan S: Activation of monocytes by HIV-Tat treatment is mediated by cytokine expression. J Immunol 159:4077-4083 (1997).

Lamhamedi-Chemadi S, Culmann-Penciolelli B, Guy B, Kieny M, Dreyfus F, Saimot A, Sereni D, Sicard D, Levy J, Gomard E: Qualitative and quantitative analysis of human cytotoxic T-lymphocyte responses to HIV-1 proteins. AIDS 6:1249-1258 (1992).

Le Buanec H, Bizzini B: Procedures for preparing biologically inactive, but immunogenic HIV-1 Tat protein (Tat toxoid) for human use. Biomed Pharmacother 54:41-44 (2000).

Li C J, Friedman D J, Wang C, Metelev V, Pardee A B: Induction of apoptosis in uninfected lymphocytes by HIV-1 Tat protein. Science 268:429-431 (1995).

Lieberman J, Fabry J A, Fong D M, Parkerson G R: Recognition of a small number of diverse epitopes dominates the cytotoxic T lymphocytes response to HIV type 1 in an infected individual. AIDS Res Hum Retroviruses 13:383-392 (1997).

Lopez-Diaz dC, Lasarte J J, Casares N, Sarobe P, Ruiz M, Prieto J, Borras-Cuesta F: Engineering Th determinants for efficient priming of humoral and cytotoxic T cell responses. Int Immunol % 2003 Jun. 15 (6):691-9 (2003).

Mansour M, Pohajdak B, Kast W M, Fuentes-Ortega A, Korets-Smith E, Weir G M, Brown R G, Daftarian P: Therapy of established B16-F10 melanoma tumors by a single vaccination of CTL/T helper peptides in VacciMax. J Transl Med 5:20 (2007).

Masemola A, Mashishi T, Khoury G, Mohube P, Mokgotho P, Vardas E, Colvin M, Zijenah L, Katzenstein D, Musonda R, Allen S, Kumwenda N, Taha T, Gray G, McIntyre J, Karim S A, Sheppard H W, Gray C M: Hierarchical Targeting of Subtype C Human Immunodeficiency Virus Type 1 Proteins by CD8(+) T Cells: Correlation with Viral Load. J Virol 78:3233-3243 (2004).

Mayol K, Munier S, Beck A, Verrier B, Guillon C: Design and characterization of an HIV-1 Tat mutant: inactivation of viral and cellular functions but not antigenicity. Vaccine 25:6047-6060 (2007).

Mishra M, Vetrivel S, Siddappa N B, Ranga U, Seth P: Clade-specific differences in neurotoxicity of human immunodeficiency virus-1 B and C Tat of human neurons: significance of dicysteine C30C31 motif. Ann Neurol 63:366-376 (2007).

Mocellin S: Cancer vaccines: the challenge of developing an ideal tumor killing system. Front Biosci % 2005 Sep. 1; 10:2285-305 (2005).

Moreau E, Belliard G, Partidos C D, Pradezinsky F, Le Buanec H, Muller S, Desgranges C: Important B-cell epitopes for neutralization of human immunodeficiency virus type 1 Tat in serum samples of humans and different animal species immunized with Tat protein or peptides. J Gen Virol 85:2893-2901 (2004).

Nath A, Conant K, Chen P, Scott C, Major E O: Transient exposure to HIV-1 Tat protein results in cytokine production in macrophages and astrocytes. A hit and run phenomenon. J Biol Chem 274:17098-17102 (1999).

Nath A, Geiger J D, Mattson M P, Magnuson D S K, Jones M, Berger J R: Role of Viral Proteins in HIV-1 Neuropathogenesis with Emphasis on Tat. NeuroAids 1: (1998).

Newman M J, Livingston B, McKinney D M, Chesnut R W, Sette A: T-lymphocyte epitope identification and their use in vaccine development for HIV-1. Front Biosci 7:d1503-d1515 (2002).

Noonan D, Albini A: From the outside in: extracellular activities of HIV Tat. Adv Pharmacol 48:229-250 (2000).

Noonan D M, Gringeri A, Meazza R, Rosso O, Mazza S, Muca-Perja M, Le Buanec H, Accolla R S, Albini A, Ferrini S: Identification of Immunodominant Epitopes in Inactivated Tat-Vaccinated Healthy and HIV-1-Infected Volunteers. J Acquir Immune Defic Syndr 33:47-55 (2003).

Novitsky V, Gilbert P, Peter T, McLane M F, Gaolekwe S, Rybak N, Thior I, Ndung'u T, Marlink R, Lee T H, Essex M: Association between virus-specific T-cell responses and plasma viral load in human immunodeficiency virus type 1 subtype C infection. J Virol 77:882-890 (2003).

Novitsky V A, Gilbert P B, Shea K, McLane M F, Rybak N, Klein I, Thior I, Ndung'u T, Lee T H, Essex M E: Interactive association of proviral load and IFN-gamma-secreting T cell responses in HIV-1C infection. Virology (2006).

Olszewska W, Obeid O E, Steward M W: Protection against measles virus-induced encephalitis by anti-mimotope antibodies: the role of antibody affinity. Virology 272:98-105 (2000).

Osmanov S, Heyward W L, Esparza J: HIV-1 genetic variability: implications for the development of HIV vaccines. Antibiot Chemother 48:30-38 (1996).

Pauza C D, Trivedi P, Wallace M, Ruckwardt T J, Le Buanec H, Lu W, Bizzini B, Burny A, Zagury D, Gallo R C: Vaccination with tat toxoid attenuates disease in simian/HIV-challenged macaques. Proc Natl Acad Sci USA 97:3515-3519 (2000).

Peloponese J M, Jr., Gregoire C, Opi S, Esquieu D, Sturgis J, Lebrun E, Meurs E, Collette Y, Olive D, Aubertin A M, Witvrow M, Pannecouque C, De Clercq E, Bailly C, Lebreton J, Loret E P: 1H-13C nuclear magnetic resonance assignment and structural characterization of HIV-1 Tat protein. C R Acad Sci III 323:883-894 (2000).

Potash M J, Chao W, Bentsman G, Paris N, Saini M, Nitkiewicz J, Belem P, Sharer L, Brooks A I, Volsky D J: A mouse model for study of systemic HIV-1 infection, antiviral immune responses, and neuroinvasiveness. Proc Natl Acad Sci USA 102:3760-3765 (2005).

Putkonen P, Quesada-Rolander M, Leandersson A, Schwartz S, Thorstensson R, Okuda K, Wahren B, Hinkula J: Immune responses but no protection against SHIV by gene-gun delivery of HIV-1 DNA followed by recombinant subunit protein boosts. Virology 250:293-301 (1998).

Ramakrishna L, Anand K K, Mohankumar K M, Ranga U: Codon Optimization of the Tat Antigen of Human Immunodeficiency Virus Type 1 Generates Strong Immune Responses in Mice following Genetic Immunization. J Virol 78:9174-9189 (2004).

Ranki A, Suni J, Blazevic V, Holmstrom P, Mattinen S, Krohn K, Valle S L: T-cell recognition of HIV antigens in HIV-seroreverted persons. AIDS11:132-133 (1997).

Re M C, Furlini G, Vignoli M, Ramazzotti E, Roderigo G, De R, V, Zauli G, Lolli S, Capitani S, La Placa M: Effect of antibody to HIV-1 Tat protein on viral replication in vitro and progression of HIV-1 disease in vivo. J Acquir Immune Defic Syndr Hum Retrovirol 10:408-416 (1995).

Re M C, Furlini G, Vignoli M, Ramazzotti E, Zauli G, La Placa M: Antibody against human immunodeficiency virus type 1 (HIV-1) Tat protein may have influenced the progression of AIDS in HIV-1-infected hemophiliac patients. Clin Diagn Lab Immunol 3:230-232 (1996).

Re M C, Vignoli M, Furlini G, Gibellini D, Colangeli V, Vitone F, La Placa M: Antibodies against full-length Tat protein and some low-molecular-weight Tat-peptides correlate with low or undetectable viral load in HIV-1 seropositive patients. J Clin Virol 21:81-89 (2001).

Reinhold D, Wrenger S, Kahne T, Ansorge S: HIV-1 Tat: immunosuppression via TGF-beta1 induction. Immunol Today 20:384-385 (1999).

Reiss P, Lange J M, De Ronde A, de Wolf F, Dekker J, Debouck C, Goudsmit J: Speed of progression to AIDS and degree of antibody response to accessory gene products of HIV-1. J Med Virol 30:163-168 (1990).

Remoli A L, Marsili G, Perrotti E, Gallerani E, Ilari R, Nappi F, Cafaro A, Ensoli B, Gavioli R, Battistini A: Intracellular HIV-1 Tat protein represses constitutive LMP2 transcription increasing proteasome activity by interfering with the binding of IRF-1 to STAT1. Biochem J 396:371-380 (2006).

Rice J, de Lima B, Stevenson F K, Stevenson P G: A gamma-herpesvirus immune evasion gene allows tumor cells in vivo to escape attack by cytotoxic T cells specific for a tumor epitope. Eur J Immunol % 2002 December; 32 (12):3481-7 (2002).

Richardson M W, Mirchandani J, Duong J, Grimaldo S, Kocieda V, Hendel H, Khalili K, Zagury J F, Rappaport J: Antibodies to Tat and Vpr in the GRIV cohort: differential association with maintenance of long-term non-progression status in HIV-1 infection. Biomed Pharmacother 57:4-14 (2003).

Richardson M W, Mirchandani J, Silvera P, Regulier E G, Capini C, Bojczuk P M, Hu J, Gracety E J, Boyer J D, Khalili K, Zagury J F, Lewis M G, Rappaport J: Immunogenicity of HIV-1 IIIB and SHIV 89.6P Tat and Tat toxoids in rhesus macaques: induction of humoral and cellular immune responses. DNA Cell Biol 21:637-651 (2002).

Rodman T C, Pruslin F H, To S E, Winston R: Human immunodeficiency virus (HIV) Tat-reactive antibodies present in normal HIV-negative sera and depleted in HIV-positive sera. Identification of the epitope. J Exp Med 175:1247-1253 (1992).

Rosa D S, Tzelepis F, Cunha M G, Soares I S, Rodrigues M M: The pan HLA DR-binding epitope improves adjuvant-assisted immunization with a recombinant protein containing a malaria vaccine candidate. Immunol Lett 92:259-268 (2004).

Rubartelli A, Poggi A, Sitia R, Zocchi M R: HIV-I Tat: a polypeptide for all seasons. Immunol Today 19:543-545 (1998).

Rusnati M, Presta M: HIV-1 Tat protein: a target for the development of anti-AIDS therapies. Drugs Fut 27:481-493 (2002).

Saini M, Hadas E, Volsky D J, Potash M J: Vaccine-induced protection from infection of mice by chimeric human immunodeficiency virus type 1, EcoHIV/NL4-3. Vaccine 25:8660-8663 (2007).

Senkaali D, Kebba A, Shafer L A, Campbell G R, Loret E P, Van Der P L, Grosskurth H, Yirrell D, Kaleebu P: Tat-Specific Binding IgG and Disease Progression in HIV Type 1-Infected Ugandans. AIDS Res Hum Retroviruses (2008).

Shojania S, O'neil J D: HIV-1 Tat Is a Natively Unfolded Protein: THE SOLUTION CONFORMATION AND DYNAMICS OF REDUCED HIV-1 Tat-(1-72) BY NMR SPECTROSCOPY. J Biol Chem 281:8347-8356 (2006).

Silvera P, Richardson M W, Greenhouse J, Yalley-Ogunro J, Shaw N, Mirchandani J, Khalili K, Zagury J F, Lewis M G, Rappaport J: Outcome of simian-human immunodeficiency virus strain 89.6p challenge following vaccination of rhesus macaques with human immunodeficiency virus Tat protein. J Virol 76:3800-3809 (2002).

Steinbrook R: One step forward, two steps back—will there ever be an AIDS vaccine? N Engl J Med 357:2653-2655 (2007).

Stevenson F K, Ottensmeier C H, Johnson P, Zhu D, Buchan S L, McCann K J, Roddick J S, King A T, McNicholl F, Savelyeva N, Rice J: DNA vaccines to attack cancer. Proc Natl Acad Sci USA % 2004 Oct. 5; 101 Suppl 2:14646-52 Epub 2004 August 3Epub (2004a).

Stevenson F K, Ottensmeier C H, Johnson P, Zhu D, Buchan S L, McCann K J, Roddick J S, King A T, McNicholl F, Savelyeva N, Rice J: DNA vaccines to attack cancer. Proc Natl Acad Sci USA 101 Suppl 2:14646-14652 (2004b).

Stittelaar K J, Gruters R A, Schutten M, van Baalen C A, van Amerongen G, Cranage M, Liljestrom P, Sutter G, Osterhaus A D: Comparison of the efficacy of early versus late viral proteins in vaccination against SIV. Vaccine 20:2921-2927 (2002).

Tikhonov I, Ruckwardt T J, Hatfield G S, Pauza C D: Tat-neutralizing antibodies in vaccinated macaques. J Virol 77:3157-3166 (2003).

Uyttenhove C, Arendse B, Stroobant V, Brombacher F, Van Snick J: Development of an anti-IL-12 p40 auto-vaccine: protection in experimental autoimmune encephalomyelitis at the expense of increased sensitivity to infection. Eur J Immunol 34:3572-3581 (2004).

van Baalen C A, Pontesilli O, Huisman R C, Geretti A M, Klein M R, de Wolf F, Miedema F, Gruters R A, Osterhaus A D: Human immunodeficiency virus type 1 Rev- and Tat-specific cytotoxic T lymphocyte frequencies inversely correlate with rapid progression to AIDS. J Gen Virol 78:1913-1918 (1997).

van Bergen J, Camps M, Offring a R, Melief C J, Ossendorp F, Koning F: Superior tumor protection induced by a cellular vaccine carrying a tumor-specific T helper epitope by genetic exchange of the class II-associated invariant chain peptide. Cancer Res 60:6427-6433 (2000).

van der Burg S H, Kwappenberg K M, Geluk A, van der K M, Pontesilli O, Hovenkamp E, Franken K L, van Meijgaarden K E, Drijfhout J W, Ottenhoff T H, Melief C J, Offring a R: Identification of a conserved universal Th epitope in HIV-1 reverse transcriptase that is processed and presented to HIV-specific CD4+ T cells by at least four unrelated HLA-DR molecules. J Immunol % 1999 Jan. 1; 162 (1):152-60 (1999).

Veljkovic V, Muller S, Kohler H: AIDSVAX results: an important open question. Vaccine 21:3528-3529 (2003).

Viscidi R P, Mayur K, Lederman H M, Frankel A D: Inhibition of antigen-induced lymphocyte proliferation by Tat protein from HIV-1. Science 246:1606-1608 (1989).

Wieland U, Kuhn J E, Jassoy C, Rubsamen-Waigmann H, Wolber V, Braun R W: Antibodies to recombinant HIV-1 vif, tat, and nef proteins in human sera. Med Microbiol Immunol (Berl) 179:1-11 (1990).

Willis R A, Kappler J W, Marrack P C: CD8 T cell competition for dendritic cells in vivo is an early event in activation. Proc Natl Acad Sci USA 103:12063-12068 (2006).

Yang Y, Tikhonov I, Rucicwardt T J, Djavani M, Zapata J C, Pauza C D, Salvato M S: Monocytes Treated with Human Immunodeficiency Virus Tat Kill Uninfected CD4(+) Cells by a Tumor Necrosis Factor-Related Apoptosis-Induced Ligand-Mediated Mechanism. J Virol 77:6700-6708 (2003).

Zagury D, Lachgar A, Chams V, Fall L S, Bernard J, Zagury J F, Bizzini B, Gringeri A, Santagostino E, Rappaport J, Feldman M, Burny A, Gallo R C: Interferon alpha and Tat involvement in the immunosuppression of uninfected T cells and C—C chemokine decline in AIDS. Proc Natl Acad Sci USA 95:3851-3856 (1998a).

Zagury J F, Sill A, Blattner W, Lachgar A, Le Buanec H, Richardson M, Rappaport J, Hendel H, Bizzini B, Gringeri A, Carcagno M, Criscuolo M, Burny A, Gallo R C, Zagury D: Antibodies to the HIV-1 Tat protein correlated with nonprogression to AIDS: a rationale for the use of Tat toxoid as an HIV-1 vaccine. J Hum Virol 1:282-292 (1998b).

Zocchi M R, Rubartelli A, Morgavi P, Poggi A: HIV-1 Tat inhibits human natural killer cell function by blocking L-type calcium channels. J Immunol 161:2938-2943 (1998).

I claim:

1. A viral Tat DNA sequence comprising SEQ ID NO: 1, wherein said sequence comprises an N-terminal region, Cysteine rich domain (CRD), Core domain, Basic domain (BD), C-terminal region and Exon II region, wherein the Cysteine rich domain (CRD) is disrupted by insertion of Pan HLA-DR Binding epitope (PADRE).

2. A viral Tat DNA sequence comprising N-terminal region, Cysteine rich domain (CRD), Core domain, Basic domain (BD), C-terminal region and Exon II region, wherein the Basic Domain (BD) is disrupted by insertion of Pan HLA-DR Binding epitope (PADRE) as represented by Sequence Id No 3, or by $Pol_{711}$ epitope as represented by Sequence Id No.4.

3. A viral Tat DNA sequence comprising N-terminal region, Cysteine rich domain (CRD), Core domain, Basic domain (BD), C-terminal region and Exon II region, wherein the Cysteine rich domain (CRD) is disrupted by insertion of Pan HLA-DR Binding epitope (PADRE) and Basic Domain (BD) is disrupted by insertion of $Pol_{711}$ as represented by Sequence Id No 5.

4. A viral Tat DNA sequence comprising N-terminal region, Cysteine rich domain (CRD), Core domain, Basic domain (BD), C-terminal region and Exon II region, wherein the Cysteine rich domain (CRD) is disrupted by insertion of $Pol_{711}$ epitope and Basic Domain (BD) is disrupted by insertion of Pan HLA-DR Binding epitope (PADRE) as represented by Sequence Id No 6.

5. A nontoxic, immunogenic viral Tat DNA sequence comprising SEQ ID NO: 1 or SEQ ID NO. 2 comprises a N terminal region, Cysteine rich domain (CRD), Core domain, Basic domain (BD), C-terminal region and Exon II region, wherein the Tat Sequence comprising SEQ ID NO: 1 is rendered nontoxic and immunogenic by insertion of Pan HLA-DR binding epitope (PADRE) into the Cysteine-rich domain, or Basic domain or Core-domain of said Tat DNA sequence, or the Tat sequence comprising SEQ ID NO: 2 is rendered nontoxic and immunogenic by insertion of $Pol_{711}$ epitope into the Cysteine-rich domain of said Tat DNA sequence.

6. The viral Tat DNA sequence as claimed in claim 5, wherein the engineered Tat DNA sequence is non-toxic to host as a consequence of structural disruption of CRD domain of Tat.

7. A process to obtain a non toxic, immunogenic viral Tat DNA sequence comprising Sequence Id No 1 or Sequence Id No 2, said method comprising steps of:
  a) amplifying full length Tat DNA to obtain PCR products with inserted Pan HLA-DR binding epitope (PADRE) into CRD or $Pol_{711}$ epitope into CRD of the amplified Tat DNA;
  b) cloning of PCR products with insertions of step (a) into mammalian expression cassettes or plasmid vectors; and
  c) insertion of expression cassettes or plasmid vectors of step (b) into a suitable host for expression to obtain said Tat DNA sequence comprising Sequence ID No 1 or Sequence Id No 2.

8. An expression vector having a non toxic, immunogenic viral Tat DNA sequence comprising Sequence Id No 1 or Sequence Id No 2, wherein said expression vector comprises a ubiquitous cellular promoter selected from a group comprising EF-1α, β-Actin EGRI, eIF4AI, FerH, FerL, GAPDH, GRP78, GRP94, HSP70, β-Kin, PGK-I, ROSA, Ubiquitin B and ubiquitin C, or any combination thereof.

9. An immunogenic composition comprising non toxic, immunogenic viral Tat DNA sequence comprising Sequence Id No 1 or Sequence Id No 2 in phosphate buffer saline.

10. The immunogenic composition according to claim 9, wherein the engineered Tat DNA sequence is nontoxic to host as a consequence of structural disruption of CRD domain of Tat.

11. A method of obtaining an immunogenic composition comprising nontoxic, immunogenic viral Tat DNA sequence selected from the group consisting of SEQ ID NO: 1, SEQ ID NO: 2, SEQ ID NO: 3, SEQ ID NO: 4, SEQ ID NO: 5, or SEQ ID NO: 6, wherein said sequence comprises a N-terminal region, Cysteine rich domain (CRD), Core domain, Basic domain (BD), C-terminal region and Exon II region, wherein the Tat Sequence is rendered nontoxic and immunogenic by insertion of HLA-DR binding epitope into the Cysteine-rich domain, or Basic domain or Core domain of said Tat DNA sequence, said method comprising step of dissolving said viral Tat DNA into phosphate buffer saline to obtain the immunogenic composition.

12. A method of inducing an immune response in a subject comprising administering a nontoxic, immunogenic viral Tat DNA sequence selected from the group consisting of SEQ ID NO: 1, SEQ ID NO: 2, SEQ ID NO: 3, SEQ ID NO: 4, SEQ ID NO: 5, or SEQ ID NO: 6, wherein said sequence comprises a N-terminal region, Cysteine rich domain (CRD), Core domain, Basic domain (BD), C-terminal region and Exon II region, wherein the Tat Sequence is rendered nontoxic and immunogenic by insertion of HLA-DR binding epitope into the Cysteine-rich domain, or Basic domain or Core domain of said Tat DNA sequence, said method comprising a step of administering a therapeutically effective dose of the immunogenic composition to a subject in need thereof.

13. A kit having an immunogenic composition comprising nontoxic, immunogenic viral Tat DNA sequence in phosphate buffer saline, wherein said Tat DNA comprises SEQ ID NO: 1 or SEQ ID NO: 2.

14. A viral Tat DNA sequence comprising SEQ ID NO: 2, wherein said sequence comprises N-terminal region, Cysteine rich domain (CRD), Core domain, Basic domain (BD), C-terminal region and Exon II region, wherein the Cysteine rich domain (CRD) is disrupted by insertion of $Pol_{711}$ epitope.

15. The expression vector according to claim 8, wherein said ubiquitous cellular promoter is EF-1α promoter.

* * * * *

```
                               SEQUENCE LISTING

<160> NUMBER OF SEQ ID NOS: 36

<210> SEQ ID NO 1
<211> LENGTH: 345
<212> TYPE: DNA
<213> ORGANISM: Artificial Sequence
<220> FEATURE:
<223> OTHER INFORMATION: Viral Tat DNA-PADRE-CRD

<400> SEQUENCE: 1
atggagccag tagatcctaa cctggagccc tggaaccacc ctggcagcca gcccaagacc      60
gcctgcaaca actgctactg caagcactgc gccaagtttg tcgctgcctg gacgctgaag     120
gctgctgcca gctaccactg cctggtgtgc ttccagacca agggcctggg catcagctac     180
ggccggaaga agcggcgcca gcgccggagc gctcctccaa gcagcgagga ccaccaaaat     240
cttatatcaa agcagcccct gcctaggacc cagggcgacc ccacaggcag cgaggagagc     300
aagaagaagg tggagagcaa gacagagaca gacccccttcg actga                   345

<210> SEQ ID NO 2
<211> LENGTH: 351
<212> TYPE: DNA
<213> ORGANISM: Artificial Sequence
<220> FEATURE:
<223> OTHER INFORMATION: Viral Tat DNA-POL-CRD

<400> SEQUENCE: 2
atggagccag tagatcctaa cctggagccc tggaaccacc ctggcagcca gcccaagacc      60
gcctgcaaca actgctactg caagcactgc gagaaggtgt acctcgcatg ggtgcctgcc     120
cacaagggca ttggcagcta ccactgcctg gtgtgcttcc agaccaaggg cctgggcatc     180
agctacggcc ggaagaagcg gcgccagcgc cggagcgctc ctccaagcag cgaggaccac     240
caaaatctta tatcaaagca gcccctgcct aggacccagg gcgaccccac aggcagcgag     300
gagagcaaga agaaggtgga gagcaagaca gagacagacc ccttcgactg a              351
```

<210> SEQ ID NO 3
<211> LENGTH: 345
<212> TYPE: DNA
<213> ORGANISM: Artificial Sequence
<220> FEATURE:
<223> OTHER INFORMATION: Viral Tat DNA-PADRE-BD

<400> SEQUENCE: 3

```
atggagccag tagatcctaa cctggagccc tggaaccacc ctggcagcca gcccaagacc      60
gcctgcaaca actgctactg caagcactgc agctaccact gcctggtgtg cttccagacc     120
aagggcctgg gcatcagcta cggccggaag aaggccaagt tgtcgctgc ctggacgctg      180
aaggctgctg cccggcgcca cgccggagc gctcctccaa gcagcgagga ccaccaaaat     240
cttatatcaa agcagcccct gcctaggacc cagggcgacc ccacaggcag cgaggagagc     300
aagaagaagg tggagagcaa gacagagaca gacccccttcg actga                    345
```

<210> SEQ ID NO 4
<211> LENGTH: 351
<212> TYPE: DNA
<213> ORGANISM: Artificial Sequence
<220> FEATURE:
<223> OTHER INFORMATION: Viral Tat DNA-POL-BD

<400> SEQUENCE: 4

```
atggagccag tagatcctaa cctggagccc tggaaccacc ctggcagcca gcccaagacc      60
gcctgcaaca actgctactg caagcactgc agctaccact gcctggtgtg cttccagacc     120
aagggcctgg gcatcagcta cggccggaag aaggagaagg tgtacctcgc atgggtgcct     180
gcccacaagg gcattggccg cgccagcgc cggagcgctc ctccaagcag cgaggaccac      240
caaaatctta tcaaagca gccctgcct aggacccagg gcgaccccac aggcagcgag        300
gagagcaaga agaaggtgga gagcaagaca gagacagacc ccttcgactg a              351
```

<210> SEQ ID NO 5
<211> LENGTH: 390
<212> TYPE: DNA
<213> ORGANISM: Artificial Sequence
<220> FEATURE:
<223> OTHER INFORMATION: Viral Tat DNA-PADRE-CRD-POL-BD

<400> SEQUENCE: 5

```
atggagccag tagatcctaa cctggagccc tggaaccacc ctggcagcca gcccaagacc      60
gcctgcaaca actgctactg caagcactgc gccaagtttg tcgctgcctg gacgctgaag     120
gctgctgcca gctaccactg cctggtgtgc ttccagacca agggcctggg catcagctac     180
ggccggaaga aggagaaggt gtacctcgca tgggtgcctg cccacaaggg cattggccgg     240
cgccagcgcc ggagcgctcc tccaagcagc gaggaccacc aaaatcttat atcaaagcag     300
cccctgccta ggacccaggg cgaccccaca ggcagcgagg agagcaagaa gaaggtggag     360
agcaagacag agacagaccc cttcgactga                                      390
```

<210> SEQ ID NO 6
<211> LENGTH: 389
<212> TYPE: DNA
<213> ORGANISM: Artificial Sequence
<220> FEATURE:
<223> OTHER INFORMATION: Viral Tat DNA-POL-CRD-PADRE-BD

<400> SEQUENCE: 6

```
atggagccag tagatcctaa cctggagccc tggaaccacc ctggcagcca gcccaagacc    60
gcctgcaaca actgctactg caagcactgc gagaaggtgt acctcgcatg ggtgcctgcc   120
cacaagggca ttggcagcta ccactgcctg gtgtgcttcc agaccagggc ctgggcatca   180
gctacggccg gaagaaggcc aagtttgtcg ctgcctggac gctgaaggct gctgcccggc   240
gccagcgccg gagcgctcct ccaagcagcg aggaccacca aaatcttata tcaaagcagc   300
ccctgcctag gacccagggc gaccccacag gcagcgagga gagcaagaag aaggtggaga   360
gcaagacaga gacagacccc ttcgactga                                     389

<210> SEQ ID NO 7
<211> LENGTH: 536
<212> TYPE: DNA
<213> ORGANISM: Artificial Sequence
<220> FEATURE:
<223> OTHER INFORMATION: Viral Tat DNA-inserted INTRON

<400> SEQUENCE: 7
atggagccag tagatcctaa cctggagccc tggaaccacc ctggcagcca gcccaagacc    60
gcctgcaaca actgctactg caagcactgc agctaccact gcctggtgtg cttccagacc   120
aagggcctgg gcatcagcta cggcggaag agcggcgcc agcgccggag cgctcctcca   180
agcagcgagg accaccaaaa tcttatatca aagcaggtga gtactccctc tcaaaagcgg   240
gcatgacttc tgcgctaaga ttgtcagttt ccaaaaacga ggaggatttg atattcacct   300
ggcccgcggt gatgcctttg agggtggccg cgtccatctg gtcagaaaag acaatctttt   360
tgttgtcaag cttgaggtgt ggcaggcttg agatctggcc atacacttga gtgacaatga   420
catccacttt gcctttctct ccacagcccc tgcctaggac ccagggcgac cccacaggca   480
gcgaggagag caagaagaag gtggagagca agacagagac agaccccttc gactga       536

<210> SEQ ID NO 8
<211> LENGTH: 230
<212> TYPE: DNA
<213> ORGANISM: Artificial Sequence
<220> FEATURE:
<223> OTHER INFORMATION: Synthetic Intron

<400> SEQUENCE: 8
gtgagtactc cctctcaaaa gcgggcatga cttctgcgct aagattgtca gtttccaaaa    60
acgaggagga tttgatattc acctggcccg cggtgatgcc tttgagggtg gccgcgtcca   120
tctggtcaga aaagacaatc ttttgttgt caagcttgag gtgtggcagg cttgagatct   180
ggccatacac ttgagtgaca atgacatcca cttgccttt ctctccacag                230

<210> SEQ ID NO 9
<211> LENGTH: 986
<212> TYPE: DNA
<213> ORGANISM: Artificial Sequence
<220> FEATURE:
<223> OTHER INFORMATION: ApaI-SacI Deletion Construct

<400> SEQUENCE: 9
acgcgttccg gtgcccgtca gtgggcagag cgcacatcgc ccacagtccc cgagaagttg    60
gggggagggg tcggcaattg aaccggtgcc tagagaaggt ggcgcggggt aaactgggaa   120
agtgatgtcg tgtactggct ccgccttttt cccgagggtg ggggagaacc gtatataagt   180
gcagtagtcg ccgtgaacgt tctttttcgc aacgggtttg ccgccagaac acaggtaagt   240
gccgtgtgtg gttcccgcgg gcctggcctc tttacgggtt atgcccttg cgtgccttga   300
```

```
attacttcca cgccctggc tgcagtacgt gattcttgat cccgagcttc gggttggaag      360
tgggtgggag agttcgaggc cttgcgctta aggagcccct tcgcctcgtg cttgagttga      420
ggcctggcct gggcgctggg gccgccgcgt gcgaatctgg tggcaccttc gcgcctgtct      480
cgctgctttc gataagtctc tagccattta aaattttga tgacctgctg cgacgctttt      540
tttctggcaa gatagtcttg taaatgcggg ccaagatctg cacactggta tttcggtttt      600
tggggccgcg ggcggcgacg gtgcaagctc aaaatggagg acgcggcgct cgggagagcg      660
ggcgggtgag tcacccacac aaaggaaaag ggcctttccg tcctcagccg tcgcttcatg      720
tgactccacg gagtaccggg cgccgtccag gcacctcgat tagttctcga gcttttggag      780
tacgtcgtct ttaggttggg gggaggggtt ttatgcgatg gagtttcccc acactgagtg      840
ggtggagact gaagttaggc cagcttggca cttgatgtaa ttctccttgg aatttgccct      900
ttttgagttt ggatcttggt tcattctcaa gcctcagaca gtggttcaaa gttttttct      960 tccatttcag gtgtcgtgaa gaattc                                          986

<210> SEQ ID NO 10
<211> LENGTH: 842
<212> TYPE: DNA
<213> ORGANISM: Artificial Sequence
<220> FEATURE:
<223> OTHER INFORMATION: SacII Deletion Construct

<400> SEQUENCE: 10
acgcgttccg gtgcccgtca gtgggcagag cgcacatcgc ccacagtccc cgagaagttg       60
gggggagggg tcggcaattg aaccggtgcc tagagaaggt ggcgcggggt aaactgggaa      120
agtgatgtcg tgtactggct ccgccttttt cccgagggtg ggggagaacc gtatataagt      180
gcagtagtcg ccgtgaacgt tcttttttcgc aacgggtttg ccgccagaac acaggtaagt      240
gccgtgtgtg gttcccgcgg gcggcgacgg ggcccgtgcg tcccagcgca catgttcggc      300 gaggcgggggc ctgcgagcgc ggccaccgag aatcggacgg gggtagtctc aagctggccg      360
gcctgctctg gtgcctggcc tcgcgccgcc gtgtatcgcc ccgccctggg cggcaaggct      420
ggcccggtcg gcaccagttg cgtgagcgga aagatggccg cttcccggcc tgctgcagg      480 gagctcaaaa tggaggacgc ggcgctcggg agagcgggcg ggtgagtcac ccacacaaag      540
gaaaagggcc tttccgtcct cagccgtcgc ttcatgtgac tccacggagt accgggcgcc      600
gtccaggcac ctcgattagt tctcgagctt ttggagtacg tcgtctttag gttggggga      660 ggggttttat gcgatggagt ttccccacac tgagtgggtg gagactgaag ttaggccagc      720
ttggcacttg atgtaattct ccttggaatt tgcccttttt gagtttggat cttggttcat      780
tctcaagcct cagacagtgg ttcaaagttt ttttcttcca tttcaggtgt cgtgaagaat      840
tc                                                                    842

<210> SEQ ID NO 11
<211> LENGTH: 798
<212> TYPE: DNA
<213> ORGANISM: Artificial Sequence
<220> FEATURE:
<223> OTHER INFORMATION: BglII-XhoI Deletion Construct

<400> SEQUENCE: 11
acgcgttccg gtgcccgtca gtgggcagag cgcacatcgc ccacagtccc cgagaagttg       60
gggggagggg tcggcaattg aaccggtgcc tagagaaggt ggcgcggggt aaactgggaa      120
```

| | |
|---|---:|
| agtgatgtcg tgtactggct ccgccttttt cccgagggtg ggggagaacc gtatataagt | 180 |
| gcagtagtcg ccgtgaacgt tcttttcgc aacgggtttg ccgccagaac acaggtaagt | 240 |
| gccgtgtgtg gttcccgcgg gcctggcctc tttacgggtt atggcccttg cgtgccttga | 300 |
| attacttcca cgcccctggc tgcagtacgt gattcttgat cccgagcttc ggggttggaag | 360 |
| tgggtgggag agttcgaggc cttgcgctta aggagcccct tcgcctcgtg cttgagttga | 420 |
| ggcctggcct gggcgctggg gccgccgcgt gcgaatctgg tggcaccttc gcgcctgtct | 480 |
| cgctgctttc gataagtctc tagccattta aaatttttga tgacctgctg cgacgctttt | 540 |
| tttctggcaa gatagtcttg taaatgcggg ccaagatctc gagcttttgg agtacgtcgt | 600 |
| ctttaggttg gggggagggg ttttatgcga tggagtttcc ccacactgag tgggtggaga | 660 |
| ctgaagttag gccagcttgg cacttgatgt aattctcctt ggaatttgcc cttttttgagt | 720 |
| ttggatcttg gttcattctc aagcctcaga cagtggttca agtttttttt cttccatttc | 780 |
| aggtgtcgtg aagaattc | 798 |

```
<210> SEQ ID NO 12
<211> LENGTH: 688
<212> TYPE: DNA
<213> ORGANISM: Artificial Sequence
<220> FEATURE:
<223> OTHER INFORMATION: PstI Deletion Construct

<400> SEQUENCE: 12
```

| | |
|---|---:|
| acgcgttccg gtgcccgtca gtgggcagag cgcacatcgc ccacagtccc cgagaagttg | 60 |
| gggggagggg tcggcaattg aaccggtgcc tagagaaggt ggcgcggggt aaactgggaa | 120 |
| agtgatgtcg tgtactggct ccgccttttt cccgagggtg ggggagaacc gtatataagt | 180 |
| gcagtagtcg ccgtgaacgt tcttttcgc aacgggtttg ccgccagaac acaggtaagt | 240 |
| gccgtgtgtg gttcccgcgg gcctggcctc tttacgggtt atggcccttg cgtgccttga | 300 |
| attacttcca cgcccctggc tgcagggagc tcaaaatgga ggacgcggcg ctcgggagag | 360 |
| cgggcgggtg agtcacccac acaaaggaaa agggcctttc cgtcctcagc cgtcgcttca | 420 |
| tgtgactcca cggagtaccg ggcgccgtcc aggcacctcg attagttctc gagcttttgg | 480 |
| agtacgtcgt ctttaggttg gggggagggg ttttatgcga tggagtttcc ccacactgag | 540 |
| tgggtggaga ctgaagttag gccagcttgg cacttgatgt aattctcctt ggaatttgcc | 600 |
| cttttttgagt ttggatcttg gttcattctc aagcctcaga cagtggttca agtttttttt | 660 |
| cttccatttc aggtgtcgtg aagaattc | 688 |

```
<210> SEQ ID NO 13
<211> LENGTH: 626
<212> TYPE: DNA
<213> ORGANISM: Artificial Sequence
<220> FEATURE:
<223> OTHER INFORMATION: PstI-SacII Deletion Construct

<400> SEQUENCE: 13
```

| | |
|---|---:|
| acgcgttccg gtgcccgtca gtgggcagag cgcacatcgc ccacagtccc cgagaagttg | 60 |
| gggggagggg tcggcaattg aaccggtgcc tagagaaggt ggcgcggggt aaactgggaa | 120 |
| agtgatgtcg tgtactggct ccgccttttt cccgagggtg ggggagaacc gtatataagt | 180 |
| gcagtagtcg ccgtgaacgt tcttttcgc aacgggtttg ccgccagaac acaggtaagt | 240 |
| gccgtgtgtg gttcccgctg cagggagctc aaaatggagg acgcggcgct cgggagagcg | 300 |
| ggcgggtgag tcacccacac aaaggaaaag ggcctttccg tcctcagccg tcgcttcatg | 360 |

```
tgactccacg gagtaccggg cgccgtccag gcacctcgat tagttctcga gcttttggag      420
tacgtcgtct ttaggttggg gggaggggtt ttatgcgatg gagtttcccc acactgagtg      480
ggtggagact gaagttaggc cagcttggca cttgatgtaa ttctccttgg aatttgccct      540
ttttgagttt ggatcttggt tcattctcaa gcctcagaca gtggttcaaa gttttttcct      600
tccatttcag gtgtcgtgaa gaattc                                          626
```

```
<210> SEQ ID NO 14
<211> LENGTH: 270
<212> TYPE: DNA
<213> ORGANISM: Artificial Sequence
<220> FEATURE:
<223> OTHER INFORMATION: SacII-EcoRI Deletion Construct

<400> SEQUENCE: 14
acgcgttccg gtgcccgtca gtgggcagag cgcacatcgc ccacagtccc cgagaagttg       60
gggggagggg tcggcaattg aaccggtgcc tagagaaggt ggcgcggggt aaactgggaa      120
agtgatgtcg tgtactggct ccgccttttt cccgagggtg ggggagaacc gtatataagt      180
gcagtagtcg ccgtgaacgt tcttttttcgc aacgggtttg ccgccagaac acaggtaagt    240
gccgtgtgtg gttcgtgtcg tgaagaattc                                      270
```

```
<210> SEQ ID NO 15
<211> LENGTH: 1193
<212> TYPE: DNA
<213> ORGANISM: Artificial Sequence
<220> FEATURE:
<223> OTHER INFORMATION: EF-1alpha Promoter Full Length Sequence

<400> SEQUENCE: 15
acgcgttccg gtgcccgtca gtgggcagag cgcacatcgc ccacagtccc cgagaagttg       60
gggggagggg tcggcaattg aaccggtgcc tagagaaggt ggcgcggggt aaactgggaa      120
agtgatgtcg tgtactggct ccgccttttt cccgagggtg ggggagaacc gtatataagt      180
gcagtagtcg ccgtgaacgt tctttttcgc aacgggtttg ccgccagaac acaggtaagt     240
gccgtgtgtg gttcccgcgg gcctggcctc tttacgggtt atggcccttg cgtgccttga      300
attacttcca cgcccctggc tgcagtacgt gattcttgat cccgagcttc gggttggaag      360
tgggtgggag agttcgaggc cttgcgctta aggagcccct tcgcctcgtg cttgagttga      420
ggcctggcct gggcgctggg gccgccgcgt gcgaatctgg tggcaccttc gcgcctgtct      480
cgctgctttc gataagtctc tagccattta aattttttga tgacctgctg cgacgctttt     540
tttctggcaa gatagtcttg taaatgcggg ccaagatctg cacactggta tttcggtttt    600
tggggccgcg gcggcgacg gggcccgtgc gtcccagcgc acatgttcgg cgaggcgggg     660
cctgcgagcg cggccaccga gaatcggacg ggggtagtct caagctggcc ggcctgctct      720
ggtgcctggc ctcgcgccgc cgtgtatcgc cccgccctgg gcggcaaggc tggcccggtc      780
ggcaccagtt gcgtgagcgg aaagatggcc gcttcccggc cctgctgcag ggagctcaaa      840
atggaggacg cggcgctcgg gagagcgggc gggtgagtca cccacacaaa ggaaaagggc      900
ctttccgtcc tcagccgtcg cttcatgtga ctccacggag taccgggcgc cgtccaggca      960
cctcgattag ttctcgagct tttggagtac gtcgtcttta ggttgggggg aggggtttta    1020
tgcgatggag tttccccaca ctgagtgggt ggagactgaa gttaggccag cttggcactt    1080
gatgtaattc tccttggaat ttgccctttt tgagtttgga tcttggttca ttctcaagcc    1140
```
tcagacagtg gttcaaagtt tttttcttcc atttcaggtg tcgtgaagaa ttc 1193

<210> SEQ ID NO 16
<211> LENGTH: 114
<212> TYPE: PRT
<213> ORGANISM: Artificial Sequence
<220> FEATURE:
<223> OTHER INFORMATION: Viral Tat DNA-PADRE-CRD
<220> FEATURE:
<221> NAME/KEY: PEPTIDE
<222> LOCATION: (1)..(114)

<400> SEQUENCE: 16

Met Glu Pro Val Asp Pro Asn Leu Glu Pro Trp Asn His Pro Gly Ser
1               5                   10                  15

Gln Pro Lys Thr Ala Cys Asn Asn Cys Tyr Cys Lys His Cys Ala Lys
            20                  25                  30

Phe Val Ala Ala Trp Thr Leu Lys Ala Ala Ala Ser Tyr His Cys Leu
        35                  40                  45

Val Cys Phe Gln Thr Lys Gly Leu Gly Ile Ser Tyr Gly Arg Lys Lys
    50                  55                  60

Arg Arg Gln Arg Arg Ser Ala Pro Pro Ser Ser Glu Asp His Gln Asn
65                  70                  75                  80

Leu Ile Ser Lys Gln Pro Leu Pro Arg Thr Gln Gly Asp Pro Thr Gly
                85                  90                  95

Ser Glu Glu Ser Lys Lys Lys Val Glu Ser Lys Thr Glu Thr Asp Pro
            100                 105                 110

Phe Asp

<210> SEQ ID NO 17
<211> LENGTH: 116
<212> TYPE: PRT
<213> ORGANISM: Artificial Sequence
<220> FEATURE:
<223> OTHER INFORMATION: Viral Tat DNA-POL-CRD
<220> FEATURE:
<221> NAME/KEY: PEPTIDE
<222> LOCATION: (1)..(116)

<400> SEQUENCE: 17

Met Glu Pro Val Asp Pro Asn Leu Glu Pro Trp Asn His Pro Gly Ser
1               5                   10                  15

Gln Pro Lys Thr Ala Cys Asn Asn Cys Tyr Cys Lys His Cys Glu Lys
            20                  25                  30

Val Tyr Leu Ala Trp Val Pro Ala His Lys Gly Ile Gly Ser Tyr His
        35                  40                  45

Cys Leu Val Cys Phe Gln Thr Lys Gly Leu Gly Ile Ser Tyr Gly Arg
    50                  55                  60

Lys Lys Arg Arg Gln Arg Arg Ser Ala Pro Pro Ser Ser Glu Asp His
65                  70                  75                  80

Gln Asn Leu Ile Ser Lys Gln Pro Leu Pro Arg Thr Gln Gly Asp Pro
                85                  90                  95

Thr Gly Ser Glu Glu Ser Lys Lys Lys Val Glu Ser Lys Thr Glu Thr
            100                 105                 110

Asp Pro Phe Asp
            115

<210> SEQ ID NO 18
<211> LENGTH: 114
<212> TYPE: PRT

<213> ORGANISM: Artificial Sequence
<220> FEATURE:
<223> OTHER INFORMATION: Viral Tat DNA-PADRE-BD
<220> FEATURE:
<221> NAME/KEY: PEPTIDE
<222> LOCATION: (1)..(114)

<400> SEQUENCE: 18

Met Glu Pro Val Asp Pro Asn Leu Glu Pro Trp Asn His Pro Gly Ser
1               5                   10                  15

Gln Pro Lys Thr Ala Cys Asn Asn Cys Tyr Cys Lys His Cys Ser Tyr
            20                  25                  30

His Cys Leu Val Cys Phe Gln Thr Lys Gly Leu Gly Ile Ser Tyr Gly
        35                  40                  45

Arg Lys Lys Ala Lys Phe Val Ala Ala Trp Thr Leu Lys Ala Ala Ala
    50                  55                  60

Arg Arg Gln Arg Arg Ser Ala Pro Pro Ser Ser Glu Asp His Gln Asn
65                  70                  75                  80

Leu Ile Ser Lys Gln Pro Leu Pro Arg Thr Gln Gly Asp Pro Thr Gly
                85                  90                  95

Ser Glu Glu Ser Lys Lys Lys Val Glu Ser Lys Thr Glu Thr Asp Pro
            100                 105                 110

Phe Asp

<210> SEQ ID NO 19
<211> LENGTH: 116
<212> TYPE: PRT
<213> ORGANISM: Artificial Sequence
<220> FEATURE:
<223> OTHER INFORMATION: Viral Tat DNA-POL-BD
<220> FEATURE:
<221> NAME/KEY: PEPTIDE
<222> LOCATION: (1)..(116)

<400> SEQUENCE: 19

Met Glu Pro Val Asp Pro Asn Leu Glu Pro Trp Asn His Pro Gly Ser
1               5                   10                  15

Gln Pro Lys Thr Ala Cys Asn Asn Cys Tyr Cys Lys His Cys Ser Tyr
            20                  25                  30

His Cys Leu Val Cys Phe Gln Thr Lys Gly Leu Gly Ile Ser Tyr Gly
        35                  40                  45

Arg Lys Lys Glu Lys Val Tyr Leu Ala Trp Val Pro Ala His Lys Gly
    50                  55                  60

Ile Gly Arg Arg Gln Arg Arg Ser Ala Pro Pro Ser Ser Glu Asp His
65                  70                  75                  80

Gln Asn Leu Ile Ser Lys Gln Pro Leu Pro Arg Thr Gln Gly Asp Pro
                85                  90                  95

Thr Gly Ser Glu Glu Ser Lys Lys Lys Val Glu Ser Lys Thr Glu Thr
            100                 105                 110

Asp Pro Phe Asp
    115

<210> SEQ ID NO 20
<211> LENGTH: 129
<212> TYPE: PRT
<213> ORGANISM: Artificial Sequence
<220> FEATURE:
<223> OTHER INFORMATION: Viral Tat DNA-PADRE-CRD-POL-BD
<220> FEATURE:
<221> NAME/KEY: PEPTIDE
<222> LOCATION: (1)..(129)

```
<400> SEQUENCE: 20

Met Glu Pro Val Asp Pro Asn Leu Glu Pro Trp Asn His Pro Gly Ser
1               5                   10                  15

Gln Pro Lys Thr Ala Cys Asn Asn Cys Tyr Cys Lys His Cys Ala Lys
            20                  25                  30

Phe Val Ala Ala Trp Thr Leu Lys Ala Ala Ser Tyr His Cys Leu
        35                  40                  45

Val Cys Phe Gln Thr Lys Gly Leu Gly Ile Ser Tyr Gly Arg Lys Lys
    50                  55                  60

Glu Lys Val Tyr Leu Ala Trp Val Pro Ala His Lys Gly Ile Gly Arg
65                  70                  75                  80

Arg Gln Arg Arg Ser Ala Pro Pro Ser Ser Glu Asp His Gln Asn Leu
                85                  90                  95

Ile Ser Lys Gln Pro Leu Pro Arg Thr Gln Gly Asp Pro Thr Gly Ser
            100                 105                 110

Glu Glu Ser Lys Lys Lys Val Glu Ser Lys Thr Glu Thr Asp Pro Phe
            115                 120                 125

Asp

<210> SEQ ID NO 21
<211> LENGTH: 129
<212> TYPE: PRT
<213> ORGANISM: Artificial Sequence
<220> FEATURE:
<223> OTHER INFORMATION: Viral Tat DNA-POL-CRD-PADRE-BD
<220> FEATURE:
<221> NAME/KEY: PEPTIDE
<222> LOCATION: (1)..(129)

<400> SEQUENCE: 21

Met Glu Pro Val Asp Pro Asn Leu Glu Pro Trp Asn His Pro Gly Ser
1               5                   10                  15

Gln Pro Lys Thr Ala Cys Asn Asn Cys Tyr Cys Lys His Cys Glu Lys
            20                  25                  30

Val Tyr Leu Ala Trp Val Pro Ala His Lys Gly Ile Gly Ser Tyr His
        35                  40                  45

Cys Leu Val Cys Phe Gln Thr Lys Gly Leu Gly Ile Ser Tyr Gly Arg
    50                  55                  60

Lys Lys Ala Lys Phe Val Ala Ala Trp Thr Leu Lys Ala Ala Ala Arg
65                  70                  75                  80

Arg Gln Arg Arg Ser Ala Pro Pro Ser Ser Glu Asp His Gln Asn Leu
                85                  90                  95

Ile Ser Lys Gln Pro Leu Pro Arg Thr Gln Gly Asp Pro Thr Gly Ser
            100                 105                 110

Glu Glu Ser Lys Lys Lys Val Glu Ser Lys Thr Glu Thr Asp Pro Phe
            115                 120                 125

Asp

<210> SEQ ID NO 22
<211> LENGTH: 101
<212> TYPE: PRT
<213> ORGANISM: Artificial Sequence
<220> FEATURE:
<223> OTHER INFORMATION: Viral Tat DNA-inserted INTRON
<220> FEATURE:
<221> NAME/KEY: PEPTIDE
<222> LOCATION: (1)..(101)
```

<400> SEQUENCE: 22

Met Glu Pro Val Asp Pro Asn Leu Glu Pro Trp Asn His Pro Gly Ser
1               5                  10                  15

Gln Pro Lys Thr Ala Cys Asn Asn Cys Tyr Cys Lys His Cys Ser Tyr
            20                  25                  30

His Cys Leu Val Cys Phe Gln Thr Lys Gly Leu Gly Ile Ser Tyr Gly
        35                  40                  45

Arg Lys Lys Arg Arg Gln Arg Arg Ser Ala Pro Pro Ser Ser Glu Asp
    50                  55                  60

His Gln Asn Leu Ile Ser Lys Gln Pro Leu Pro Arg Thr Gln Gly Asp
65                  70                  75                  80

Pro Thr Gly Ser Glu Glu Ser Lys Lys Val Glu Ser Lys Thr Glu
                85                  90                  95

Thr Asp Pro Phe Asp
            100

<210> SEQ ID NO 23
<211> LENGTH: 41
<212> TYPE: DNA
<213> ORGANISM: Human immunodeficiency virus
<220> FEATURE:
<221> NAME/KEY: primer_bind
<222> LOCATION: (1)..(41)

<400> SEQUENCE: 23
tagaattcgc cgccgccatg gagccagtag atcctaacct a                    41

<210> SEQ ID NO 24
<211> LENGTH: 44
<212> TYPE: DNA
<213> ORGANISM: Human immunodeficiency virus
<220> FEATURE:
<221> NAME/KEY: primer_bind
<222> LOCATION: (1)..(44)

<400> SEQUENCE: 24
gtcgccctgg gtcctaggca ggggctgctt tgatataaga tttt                 44

<210> SEQ ID NO 25
<211> LENGTH: 87
<212> TYPE: DNA
<213> ORGANISM: Human immunodeficiency virus
<220> FEATURE:
<221> NAME/KEY: primer_bind
<222> LOCATION: (1)..(87)

<400> SEQUENCE: 25
cccctgccta ggacccaggg cgaccccaca ggcagcgagg agagcaagaa gaaggtggag    60
agcaagacag agacagaccc cttcgac                                       87

<210> SEQ ID NO 26
<211> LENGTH: 37
<212> TYPE: DNA
<213> ORGANISM: Human immunodeficiency virus
<220> FEATURE:
<221> NAME/KEY: primer_bind
<222> LOCATION: (1)..(37)

<400> SEQUENCE: 26
agagtctaga ctagtcgaag gggtctgtct ctgtctt                          37

<210> SEQ ID NO 27

```
<211> LENGTH: 43
<212> TYPE: DNA
<213> ORGANISM: Human immunodeficiency virus
<220> FEATURE:
<221> NAME/KEY: primer_bind
<222> LOCATION: (1)..(43)

<400> SEQUENCE: 27
gaccaccaaa atcttatatc aaagcaggtg agtactccct ctc                         43

<210> SEQ ID NO 28
<211> LENGTH: 38
<212> TYPE: DNA
<213> ORGANISM: Human immunodeficiency virus
<220> FEATURE:
<221> NAME/KEY: primer_bind
<222> LOCATION: (1)..(38)

<400> SEQUENCE: 28
tcgcccgggt cctaggcagg ggctgtggag agaaaggc                               38

<210> SEQ ID NO 29
<211> LENGTH: 13
<212> TYPE: PRT
<213> ORGANISM: Artificial Sequence
<220> FEATURE:
<223> OTHER INFORMATION: Pan DR helper T-cell epitope
<220> FEATURE:
<221> NAME/KEY: PEPTIDE
<222> LOCATION: (1)..(13)

<400> SEQUENCE: 29

Ala Lys Phe Val Ala Ala Trp Thr Leu Lys Ala Ala Ala
1               5                   10

<210> SEQ ID NO 30
<211> LENGTH: 15
<212> TYPE: PRT
<213> ORGANISM: Artificial Sequence
<220> FEATURE:
<223> OTHER INFORMATION: pol 711 epitope
<220> FEATURE:
<221> NAME/KEY: PEPTIDE
<222> LOCATION: (1)..(15)

<400> SEQUENCE: 30

Glu Lys Val Tyr Leu Ala Trp Val Pro Ala His Lys Gly Ile Gly
1               5                   10                  15

<210> SEQ ID NO 31
<211> LENGTH: 37
<212> TYPE: DNA
<213> ORGANISM: Human immunodeficiency virus
<220> FEATURE:
<221> NAME/KEY: primer_bind
<222> LOCATION: (1)..(37)

<400> SEQUENCE: 31
atagacgcgt gtgaggctca ggtcgccgtc agtgggc                                37

<210> SEQ ID NO 32
<211> LENGTH: 21
<212> TYPE: DNA
<213> ORGANISM: Human immunodeficiency virus
<220> FEATURE:
<221> NAME/KEY: primer_bind
<222> LOCATION: (1)..(21)

<400> SEQUENCE: 32
```

```
gggcttaagc gcaaggcgtc g                                              21

<210> SEQ ID NO 33
<211> LENGTH: 17
<212> TYPE: DNA
<213> ORGANISM: Human immunodeficiency virus
<220> FEATURE:
<221> NAME/KEY: primer_bind
<222> LOCATION: (1)..(17)

<400> SEQUENCE: 33
ggccaaaccc cgttctg                                                   17

<210> SEQ ID NO 34
<211> LENGTH: 22
<212> TYPE: DNA
<213> ORGANISM: Human immunodeficiency virus
<220> FEATURE:
<221> NAME/KEY: primer_bind
<222> LOCATION: (1)..(22)

<400> SEQUENCE: 34
acttaacagg tttgggcttg ga                                             22

<210> SEQ ID NO 35
<211> LENGTH: 21
<212> TYPE: DNA
<213> ORGANISM: Human immunodeficiency virus
<220> FEATURE:
<221> NAME/KEY: primer_bind
<222> LOCATION: (1)..(21)

<400> SEQUENCE: 35
gagctgaacg ggaagctcac t                                              21

<210> SEQ ID NO 36
<211> LENGTH: 27
<212> TYPE: DNA
<213> ORGANISM: Human immunodeficiency virus
<220> FEATURE:
<221> NAME/KEY: primer_bind
<222> LOCATION: (1)..(27)

<400> SEQUENCE: 36
cacgtcagat ccacgacgga cacattg                                        27
```